(12) United States Patent
Rehan et al.

(10) Patent No.: US 9,173,875 B2
(45) Date of Patent: Nov. 3, 2015

(54) TREATMENT FOR NICOTINE-INDUCED LUNG DISEASE USING PEROXISOME PROLIFERATOR-ACTIVATED RECEPTOR GAMMA AGONISTS

(75) Inventors: Virender K. Rehan, Torrance, CA (US); John S. Torday, Redondo Beach, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 1017 days.

(21) Appl. No.: 12/296,656

(22) PCT Filed: Apr. 10, 2007

(86) PCT No.: PCT/US2007/008751
§ 371 (c)(1),
(2), (4) Date: May 4, 2009

(87) PCT Pub. No.: WO2007/120605
PCT Pub. Date: Oct. 25, 2007

(65) Prior Publication Data
US 2010/0010056 A1    Jan. 14, 2010

Related U.S. Application Data

(60) Provisional application No. 60/791,612, filed on Apr. 11, 2006, provisional application No. 60/813,430, filed on Jun. 13, 2006.

(51) Int. Cl.
*A61K 31/44* (2006.01)
*A61K 31/4439* (2006.01)

(52) U.S. Cl.
CPC ............... *A61K 31/4439* (2013.01)

(58) Field of Classification Search
CPC ............................... A61K 31/4439
USPC ............................... 514/369
See application file for complete search history.

(56) References Cited

U.S. PATENT DOCUMENTS

| 2001/0036955 A1* | 11/2001 | Gerritsen et al. ............. 514/369 |
| 2004/0122059 A1* | 6/2004 | Cantorna et al. ............. 514/342 |
| 2004/0157885 A1 | 8/2004 | Bagley et al. |
| 2004/0248934 A1 | 12/2004 | Chang et al. |
| 2005/0020654 A1 | 1/2005 | Pershadsingh et al. |

(Continued)

FOREIGN PATENT DOCUMENTS

| EP | 1057896 | 6/2000 |
| WO | WO/2007/120605 | 10/2007 |

OTHER PUBLICATIONS

Aljada et al., The Journal of Clinical Endocrinology and Metabolism, 2001;86(7):3250-3256.*

(Continued)

*Primary Examiner* — San-Ming Hui
(74) *Attorney, Agent, or Firm* — Tom Hunter; Weaver Austin Villeneuve & Sampson LLP

(57) ABSTRACT

This invention provides pertains to the discovery that that nicotine interrupts molecular signaling between endodermal and mesodermal cells of the lung alveolus. Treatment of the lung with specific molecular agents (e.g., PPAR gamma agonists) can prevent and/or reverse the injury caused by nicotine.

15 Claims, 27 Drawing Sheets

(56) References Cited

U.S. PATENT DOCUMENTS

2007/0191429 A1    8/2007    Bagley et al.
2011/0195993 A1    8/2011    Masson et al.

OTHER PUBLICATIONS

Tsubouchi et al., Biochemical and Biophysical Research Communications, 2000;270:400-405.*
Patel et al., Journal of Immunology, 2003;170:2663-2669.*
International Search Report and Written Opinion dated Aug. 12, 2008 issued in PCT/US2007/08751 (WO/2007/120605).
PCT International Preliminary Report on Patentability dated Oct. 14, 2008 issued in PCT/US2007/08751 (WO/2007/120605).
Bassi et al. (1984) "Fetal growth retardation due to maternal tobacco smoke exposure in the rat." *Pediatr. Res.* 18: 127-130.
Chen et al. (1987) "Human fetal lung changes associated with maternal smoking during pregnancy" *Pediatr Pulmonol* 3: 51-58.
Chen et al. (2005) "Effects of maternal nicotine exposure on lung surfactant system in rats" *Pediatr. Pulmonol*. 39: 97-102.
Cnattingius et al. (1996) "Maternal smoking and feto-infant mortality: biological pathways and public health significance" *Acta Paediatr* 85: 1400-1402.
Collins et al. (1985) "Fetal lung hypoplasia associated with maternal smoking: a morphometric analysis." *Pediatr. Res*. 19: 408-412.
Cunningham et al. (1994) "Maternal Smoking during Pregnancy as a Predictor of Lung Function in Children" *Am J Epidemiol* 139: 1139-1152.
Curet et al. (1983) "Maternal smoking and respiratory distress syndrome." *Am. J. Obstet. Gynecol*. 147: 446-450.
Dubey et al. (1993) "Pioglitazone attenuates hypertension and inhibits growth of renal arteriolar smooth muscle in rats" *Am. J. Physiol. Regul. Integr. Comp. Physiol*. 265: R726-R732.
Gilliland et al. (2003) "Effects of Early Onset Asthma and In Utero Exposure to Maternal Smoking on Childhood Lung Function" *Am J Respir Crit Care Med* 167: 917-924.
Gluck et al. (1973) "Lecithin-sphingomyelin ratios in amniotic fluid in normal and abnormal pregnancy." *Am J Obstet Gynecol* 115: 539-546.
Hamilton et al. (2004) "Births: preliminary data for 2003." *Natl. Vital Stat. Rep*. 53: 1-17.
Hanrahan et al. (1992) "The effect of maternal smoking during pregnancy on early infant lung function." *Am Rev Respir Dis* 145: 1129-1135.
Hermans et al. (2001) "Maternal tobacco smoking and lung epithelium-specific proteins in amniotic fluid." *Pediatr. Res*. 50: 487-494.
Higgins (2002) "Smoking in pregnancy" *Curr Opin Obstet Gynecol* 14: 145-151.
Hofhuis et al. (2003) "Adverse health effects of prenatal and postnatal tobacco smoke exposure on children" *Arch Dis Child* 88: 1086-1090.
Klerman et al. (2000) "Smoking reduction activities in a federal program to reduce infant mortality among high risk women" *Tob Control* 9, Suppl 3: III51-III55.
Kordom et al. (2003) "Maternal nicotine exposure during pregnancy and lactation: I. Effect on glycolysis in the lungs of the offspring." *Exp. Lung Res*. 29: 79-89.
Boros et al. (2002) "Oxygen-induced metabolic changes and transdifferentiation in immature fetal rat lung lipofibroblasts." *Mol Genet Metab* 77: 230-236.
Law et al. (2000) "Expression and Function of PPARg in Rat and Human Vascular Smooth Muscle Cells" *Circulation* 101: 1311-1318.
Leslie et al. (1990) "Alpha smooth muscle actin expression in developing and adult human lung." *Differentiation* 44: 143-149.
Lieberman et al. (1992) "Association of intrauterine cigarette smoke exposure with indices of fetal lung maturation." *Obstet. Gynecol*. 79: 564-570.
Luck et al. (1985) "Extent of nicotine and cotinine transfer to the human fetus, placenta and amniotic fluid of smoking mothers." *Dev. Pharmacol. Ther*. 8: 384-395.
Maritz (1988) "Effect of Maternal Nicotine Exposure on Growth in vivo of Lung Tissue of Neonatal Rats" *Biol Neonate* 53: 163-170.
Maritz et al. (1998) "Maternal nicotine exposure during gestation and lactation interferes with alveolar development in the neonatal lung." *Reprod. Fertil. Dev*. 10: 255-261.
Maritz et al. (1995) "Maternal nicotine exposure: response of type II pneumocytes of neonatal rat pups." *Cell. Biol. Int*. 19: 323-331.
Maritz et al. (1992) "Effect of maternal nicotine exposure on neonatal lung elastic tissue and possible consequences." *S. Afr. Med. J*. 81: 517-519.
Pache et al. (1998) "Myofibroblasts in diffuse alveolar damage of the lung." *Mod Pathol* 11: 1064-1070.
Pastrakuljic et al. (1998) "Transplacental transfer and biotransformation studies of nicotine in the human placental cotyledon perfused in vitro." *Life Sci*. 63: 2333-2342.
Pierce et al. (2002) "Prenatal Nicotine Exposure and Abnormal Lung Function" *Am. J. Respir. Cell Mol. Biol*. 26: 10-13.
Proskocil et al. (2005) "Vitamin C Prevents the Effects of Prenatal Nicotine on Pulmonary Function in Newborn Monkeys" *Am. J. Respir. Crit. Care Med*. 171: 1032-1039.
Rehan et al. (2003) "Hyperoxia augments pulmonary lipofibroblast-to-myofibroblast transdifferentiation." *Cell Biochem Biophys* 38: 239-250.
Rehan et al. (2005) "Mechanism of nicotine-induced pulmonary fibroblast transdifferentiation." *Am. J. Physiol. Lung Cell Mol. Physiol*. 289: L667-L676.
Rehan et al. (2006) "Evidence for the presence of lipofibroblasts in human lung." *Exp. Lung Res*. 32: 379-393.
Rubin et al. (2000) "Parathyroid hormone-related protein (PTHrP) biology in fetal lung development." *In: Mendelson CR, editor. Endocrinology of the lung: development and surfactant synthesis. Totowa, NJ: Humana*, p. 269-297.
Rubin et al. (1994) "Parathyroid hormone (PTH) and PTH-related protein stimulate surfactant phospholipid synthesis in rat fetal lung, apparently by a mesenchymal-epithelial mechanism." *Biochim Biophys Acta* 1223: 91-100.
Rubin et al. (2004) "Arrested pulmonary alveolar cytodifferentiation and defective surfactant synthesis in mice missing the gene for parathyroid hormone-related protein." *Dev. Dyn*. 230: 278-289.
Sandberg et al. (2004) "Altered lung development after prenatal nicotine exposure in young lambs." *Pediatr. Res*. 56: 432-439.
Schultz et al. (2002) "Role of adipocyte differentiation-related protein in surfactant phospholipid synthesis by type II cells" *Am. J. Physiol. Lung Cell Mol. Physiol*. 283: L288-L296.
Scott (2004) "The Pulmonary Surfactant: Impact of Tobacco Smoke and Related Compounds on Surfactant and Lung Development" *Tobacco Induced Diseases* 2: 3-25.
Sekhon et al. (1999) "Prenatal nicotine increases pulmonary $\alpha 7$ nicotinic receptor expression and alters fetal lung development in monkeys" *J Clin Invest* 103: 637-647.
Sekhon et al. (2001) "Prenatal Nicotine Exposure Alters Pulmonary Function in Newborn Rhesus Monkeys" *Am J Respir Crit Care Med* 164: 989-994.
Sekhon et al. (2002) "Maternal Nicotine Exposure Upregulates Collagen Gene Expression in Fetal Monkey Lung" *Am. J. Respir. Cell Mol. Biol*. 26: 31-41.
Szuts et al. (1978) "Long-term fate of [14C]nicotine in the mouse: Retention in the bronchi, melanin-containing tissues and urinary bladder wall" *Toxicology* 10: 207-220.
Torday et al. (2003) "Mechanotransduction determines the structure and function of lung and bone: a theoretical model for the pathophysiology of chronic disease." *Cell Biochem Biophys* 37: 235-246.
Torday et al. (2002) "Stretch-stimulated surfactant synthesis is coordinated by the paracrine actions of PTHrP and leptin" *Am. J. Physiol. Lung Cell Mol. Physiol*. 283: L130-L135.
Torday et al. (1995) "Metabolism and fate of neutral lipids of fetal lung fibroblast origin." *Biochim Biophys Acta* 1254: 198-206.
Torday et al. (1998) "Paracrine mediators of mechanotransduction in lung development." *Am J Med Sci* 316: 205-208.
Torday et al. (2001) "Biologic role of fetal lung fibroblast triglycerides as antioxidants." *Pediatr Res* 49: 843-849.
Torday et al. (2002) "Pre- and Postnatal Lung Development, Maturation, and Plasticity Leptin mediates the parathyroid hormone-re

(56) References Cited

OTHER PUBLICATIONS

*lated protein paracrine stimulation of fetal lung maturation" Am. J. Physiol. Lung Cell Mol. Physiol.* 282: L405-L410, *erratum in Am. J. Physiol. Lung Cell Mol. Physiol.* (2002) 282(4) Section L.

Torday et al. (2003) "The role of fibroblast transdifferentiation in lung epithelial cell proliferation, differentiation, and repair in vitro." *Pediatr. Pathol. Mol. Med.* 22: 189-207.

Toti et al. (1997) "Bronchopulmonary dysplasia of the premature baby" *Pediatr Pulmonol* 24: 22-28.

Wakino et al. (2000) "Peroxisome Proliferator-activated Receptor g Ligands Inhibit Retinoblastoma Phosphorylation and Gl-S Transition in Vascular Smooth Muscle Cells" *J. Biol. Chem.* 275: 22435-22441.

Walsh (1994) "Effects of maternal smoking on adverse pregnancy outcomes: examination of the criteria of causation." *Hum. Biol.* 66: 1059-1092.

Wuenschell et al. (1998) "Nicotine stimulates branching and expression of SP-A and SP-C mRNAs in embryonic mouse lung culture" *Am. J. Physiol Lung Cell Mol Physiol* 274: L165-L170.

\* cited by examiner

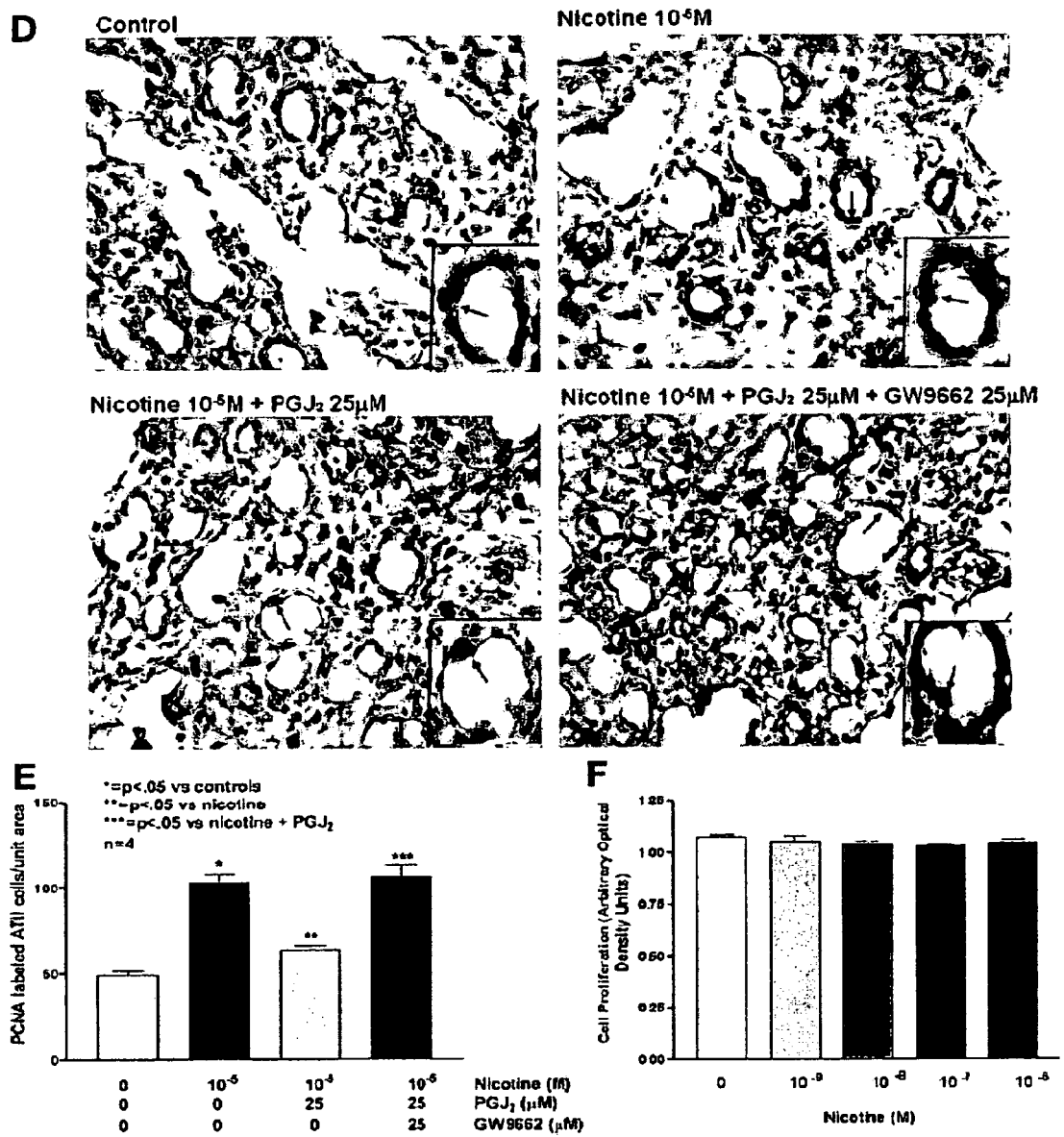
Fig. 18, cont'd.

TREATMENT FOR NICOTINE-INDUCED LUNG DISEASE USING PEROXISOME PROLIFERATOR-ACTIVATED RECEPTOR GAMMA AGONISTS

CROSS-REFERENCE TO RELATED APPLICATIONS

This application is a 371 National Phase of PCT/US2007/008751, filed on Apr. 10, 2007, which claims benefit of and priority to USSN 60/791,612, filed on Apr. 11, 2006, and USSN 60/813,430, filed on Jun. 13, 2006, all of which are incorporated herein by reference in their entirety for all purposes.

STATEMENT AS TO RIGHTS TO INVENTIONS MADE UNDER FEDERALLY SPONSORED RESEARCH AND DEVELOPMENT

Not Applicable

FIELD OF THE INVENTION

This invention pertains to the area of lung diseases. In certain embodiments, this invention provides methods and compositions to treat or prevent nicotine-induced lung damage.

BACKGROUND OF THE INVENTION

Maternal smoking during pregnancy has diverse adverse effects on fetal outcome, including increased risk of spontaneous abortion, stillbirth, premature delivery, low birth weight, early neonatal mortality, sudden infant death syndrome, and poor pulmonary outcome (Cunningham et al. (1994) Am. J. Epidemiol. 139: 1139-1152; Gilliland et al. (2003) Am. J. Respir. Crit. Care Med 167: 917-924.; Hanrahan et al. (1992) Am. Rev. Respir. Dis. 145: 1129-1135; Higgins (2002) Curr Opin Obstet Gynecol 14: 145-151; Hofhuis et al. (2003) Arch. Dis. Child 88: 1086-1090.). Maternal smoking during pregnancy adversely affects fetal lung growth that may result in adverse long-term consequences such as increased occurrence of lower respiratory illnesses and altered pulmonary mechanics on pulmonary function testing (Chen et al. (1987) Pediatr. Pulmonol., 3: 51-58; Collins et al. (1985) Pediair. Res. 19: 408-412; Gilliland et al. (2003) Am. J. Respir. Crit. Care Med 167: 917-924; Hofhuis et al. (2003) Arch. Dis. Child, 88: 1086-1090; Maritz (1988) Biol. Neonate, 53: 163-170; Scott (2004) Tobacco Induced Diseases 2: 3-25; Walsh (1994) Hum. Biol., 66: 1059-1092). The mechanisms underlying the general effects of maternal smoking on fetal viability and growth are generally thought to be due to fetal hypoxia (Cnattingius and Nordstrom (1996) Acta Paediair. 85: 1400-1402). The mechanisms underlying pulmonary outcomes, however, appear to be more complex and are poorly understood Scott (2004) Tobacco Induced Diseases 2: 3-25). On the one hand, there is evidence of increased surfactant production at birth, possibly contributing to a decrease in the incidence of respiratory distress syndrome (Curet et al. (1983) Am. J. Obstet. Gynecol. 147: 446-450; Gluck and Kulovich (1973) Am J Obstet Gynecol. 115: 539-546; Lieberman et al. (1992) Obstet. Gynecol. 79: 564570; 39. Wuenschell et al. (1998) Am. J. Physiol. Lung Cell Mol. Physiol. 274: L165-L170). On the other hand, there is strong evidence for deleterious effects on pre- and postnatal lung growth and development following in utero exposure to maternal smoking (Chen et al. (1987) Pediatr Pulmonol 3: 51-58; Cnattingius and Nordstrom (1996) Acta Paediatr 85: 1400-1402; Collins et al. (1985) Pediatr. Res., 19: 408-412; Cunningham et al. (1994) Am J Epidemiol 139: 1139-1152; Gilliland et al. (2003) Am. J. Respir. Crit. Care Med., 167: 9.17-924; Hanrahan et al. (1992) Am. Rev. Respir. Dis., 145: 1129-1135; Higgins (2002) Curr. Opin. Obstet. Gynecol., 14: 145-151; Hofhuis et al. (2003) Arch Dis Child 88: 1086-1090; Maritz (1988) Biol Neonate 53: 163-170; Scott (2004) Tobacco Induced Diseases 2: 3-25; Sekhon et al. (1999) J Clin Invest 103: 637647; Sekhon et al. (2001) Am. J. Respir. Crit. Care Med., 164: 989-994; Walsh (1994) Hum. Biol., 66: 1059-1092). The mechanisms underlying these seemingly paradoxical effects remain largely unknown.

There is, consequently, currently no specific treatment for the deleterious effects of smoking on the lung. Such patients are typically treated with steroids and P blockers, which alleviate the symptoms caused by smoking, but do not address the actual etiology of the smoke-induced effects.

SUMMARY OF THE INVENTION

This invention pertains to the elucidation of a mechanism of altered prenatal and postnatal lung development and function and provides a molecular approach to its prevention.

Both normal lung development and injury/repair utilize common mesenchymal-epithelial signaling pathways to maintain homeostasis. Epithelially-derived parathyroid hormone-related protein (PTHrP) induces the differentiation of mesodermal alveolar interstitial fibroblasts to lipid-containing interstitial lipofibroblasts (LIF) via a PTHrP receptor-mediated, cAMP-dependent PKA pathway. Other important key proteins in this pathway include peroxisome proliferator-activated receptor (PPAR) and adipocyte differentiation-related protein (ADRP). The lipid-containing LIFs produce factors that induce the growth and differentiation of the adjoining type II cells, culminating in alveolar homeostasis. Factors that disrupt this cellular homeostatic mechanism by causing the transdifferentiation of LIFs to myofibroblasts (MYFS) lead to abnormal lung development and function. Using embryonic WI38 human lung fibroblasts as a model, we tested the hypothesis that in vitro nicotine exposure specifically disrupts PTHrP-mediated alveolar epithelial-mesenchymal paracrine signaling that results in alveolar LIF-to-MYF transdifferentiation, resulting in altered pulmonary growth and differentiation. Furthermore, demonstrate that by targeting the specific molecular elements that maintain the LIF phenotype, nicotine-induced LIF-to-MYF such transdifferentiation could be prevented.

Thus, in certain embodiments, this invention provides methods of reducing, eliminating, and/or reversing nicotine damage in a mammal. The methods typically involve contacting pulmonary tissue in the mammal with a PTHrP signaling agonist. The PTHrP signaling agonist is typically provided as sufficient dosage to reduce, eliminate, and/or revserse nicotine damage in the mammal. In certain embodiments the PTHrP signaling agonist comprises a PPAR gamma (PPARγ) agonist. In certain embodiments the mammal is a pregnant mammal and the pulmonary tissue is in a developing fetus. In certain embodiments the mammal is a pregnant mammal and said pulmonary tissue comprises pulmonary tissue of said pregnant mammal. In certain embodiments the mammal is a human smoker. In certain embodiments the mammal is a non-human mammal or a human, exposed to second-hand smoke. In certain embodiments the human is a human diagnosed as having asthma, chronic obstructive pulmonary disease, lung cancer, or emphysema. In certain embodiments the human is a human that is formerly a smoker. In various embodiments the PPAR gamma agonist is a thiozolidinedione. In certain embodiments PPAR gamma agonist includes one or more agents independently selected from the group consisting of rosiglitazone, troglitazone (Resulin), farglitazar, phenylacetic acid, GW590735, GW677954, Avandia, Avandamet (avandia+metformin), ciglitazone, 15 deoxy prostaglandin J2 (15PGJ2), pioglitazone (Actos), 15-deoxydelta-12,14 PGJ2, MCC-555, and triterpenoids (e.g., 2-Cyano-3,12-dioxoolean-1,9-dien-28-oic acid (CDDO), CDDO-Me, and CDDOIm (see, e.g., Chintharlapalli, et al. (2005) Mol. Pharmacol., 68: 119-128), and the like). In certain embodiments the PTHrP signaling agonist (e.g., PPAR gamma agonist) is administered via an inhalation route. In certain embodiments the PTHrP signaling agonist (e.g., PPAR gamma agonist) is administered via a nasal spray. In certain embodiments the PTHrP signaling agonist (e.g., PPAR gamma agonist) is administered via an oral inhaler. In certain embodiments the PTHrP signaling agonist (e.g., PPAR gamma agonist) is administered orally. In certain embodiments the PTHrP signaling agonist (e.g., PPAR gamma agonist) is administered systemically.

Also provided are methods for inhibiting or repairing deleterious effects of smoking on the lung. The methods typically involve method comprising administering to a subject in need thereof a sufficient amount of a PTHrP signaling agonist (e.g., PPAR gamma agonist) to inhibit or repair smoking-induced damage to the lung.

Methods are provided for screening for an agent that inhibits or repairs a deleterious effect of smoking on the lung. The methods typically involve screening the test agent for PTHrP signaling agonistic activity (e.g., PPAR gamma agonist activity), where the PTHrP signaling activity is an indicator that the test agent is a candidate agent for the treatment or prevention of smoking-induced lung damage.

Methods are also provided for screening for an agent that mitigates one or more symptoms of nicotine-induced pulmonary damage. The methods typically involve exposing a test agent to a test mammal or to a mammalian cell; and determining the expression or activity of a PTHrP signaling pathway component (e.g., PPAR gamma and/or a PPAR gamma receptor), where an increase in the component expression or activity in the test mammal indicates that the test agent is a good candidate agent for mitigating, stopping, or reversing one or more symptoms of nicotine-induced pulmonary damage in a mammal. In certain embodiments the determining the expression comprises measuring the level of nucleic acid encoding PPAR gamma and/or a PPAR gamma receptor. In certain embodiments the measuring comprises measuring the level of expressed PPAR gamma and/or PPAR gamma receptor protein. In various embodiments the measuring is via a method selected from the group consisting of capillary electrophoresis, a Western blot, mass spectroscopy, ELISA, immunochromatography, and immunohistochemistry. In various embodiments the determining the expression comprises measuring the level of mRNA encoding PPAR gamma and/or a PPAR gamma receptor. In certain embodiments the level of PPAR gamma mRNA or PPAR gamma receptor mRNA is measured by hybridizing the mRNA to a probe that specifically hybridizes to a PPAR gamma or PPAR gamma receptor nucleic acid (e.g., via a method selected from the group consisting of a Northern-blot, a Southern blot using DNA derived from the PPAR gamma RNA and/or PPAR gamma receptor RNA, an array hybridization, an affinity chromatography, and an in situ hybridization). In certain embodiments the level of PPAR gamma and/or PPAR gamma receptor mRNA is measured using a nucleic acid amplification reaction.

In various embodiments kits are provided for mitigating or reversing nicotine-induce pulmonary damage. The kits typically comprises a container containing one or more PTHrP pathway signaling agonists (e.g., PPAR gamma agonists) and instructional materials teaching the use of PPAR gamma agonists in the treatment of nicotine-induced pulmonary damage.

Also provided is the use of a PTHrP signaling agonist (e.g., PPAR gamma agonist) in the treatment of nicotine-induced pulmonary damage.

In certain embodiments, use of a PTHrP signaling agonist (e.g., PPAR gamma agonist) in the manufacture of a medicament for the treatment of nicotine-induced pulmonary damage is also provided.

In certain embodiments of the methods and treatments described herein, the mammal is not a human or non-human mammal diagnosed with and/or being treated for asthma, chronic obstructive pulmonary disease, lung cancer, or emphysema and/or is not being treated for diabetes, and/or obesity or anexoria, and/or an eating or appetite disorder.

DEFINITIONS

The terms "PPAR gamma ligand" and "PPAR gamma agonist" are used interchangeably and refers to an agent that upregulates directly or indirectly activity of a pathway mediated by a PPAR gamma receptor. PPAR-γ agonists include agents that, when interacting directly or indirectly with PPAR-Y, increase the biological activity of PPAR-γ (e.g., the ability of PPAR-γ to inhibit Egr-1 expression).

The term "a PTHrP receptor" is used to mean a receptor that binds to PTHrP, and examples include a PTHrP type I receptor (described, e.g., in Japanese Patent Application Laying-Open (Kohyo) No. 6-506598).

The term "second-hand smoke" refers to smoke, typically smoke produced by burning tobacco or a burning tobacco product that is inhaled or otherwise contacted by a person other than the person who is utilizing the burning tobacco or burning tobacco product (e.g., the smoker).

The term "administering" when used herein with respect to a PPARγ agonist includes, but is not limited to giving, providing, feeding, dispensing, inserting, injecting, infusing, perfusing, prescribing, furnishing, treating with, taking, spraying, inhaling, swallowing, eating, or applying a pharmaceutically acceptable PPARγ agonist-containing composition.

Figure 19:
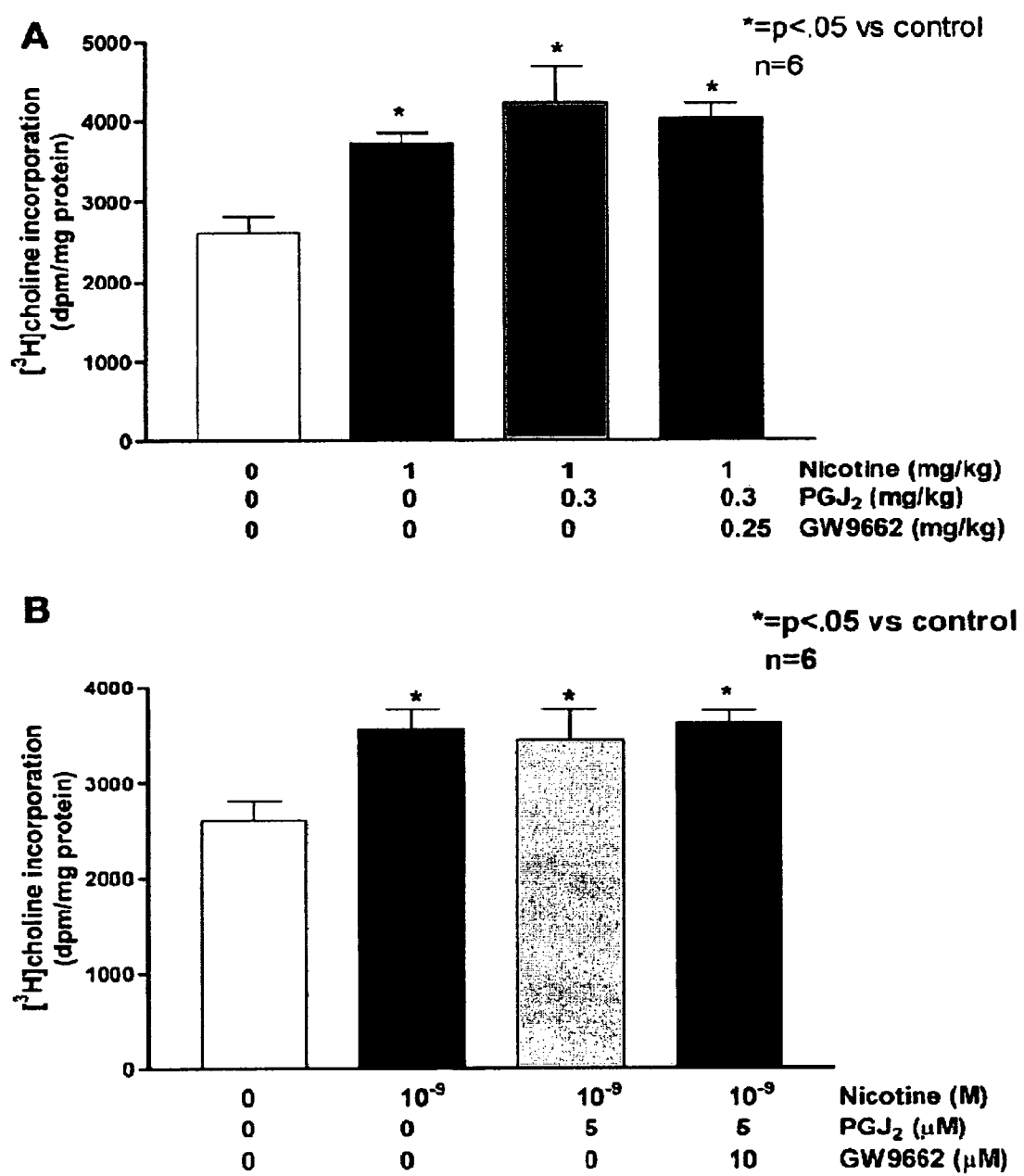

FIG. 19, panels A and B show the effect of nicotine on surfactant phosphatidylcholine synthesis in vivo and in vitro. Surfactant phospholipid synthesis measured by [$^3$H]choline incorporation [disintegrations/min (dpm) per mg protein] into saturated phosphatidylcholine by cultured ATII cells after in utero (1 mg/kg ip administered once daily pregnant dam from embryonic day 6 to 20; Panel A) or in vitro ($1 \times 10^{-9}$ M for 24 h; Panel B) nicotine treatment was significantly increased in the nicotine-exposed group vs. the control group. Concomitant treatment with the PPAR-γ agonist $PGJ_2$ or antagonist GW9662 had no effect on the nicotine-induced increase in phospholipid synthesis in utero or in vitro.

Figure 20:
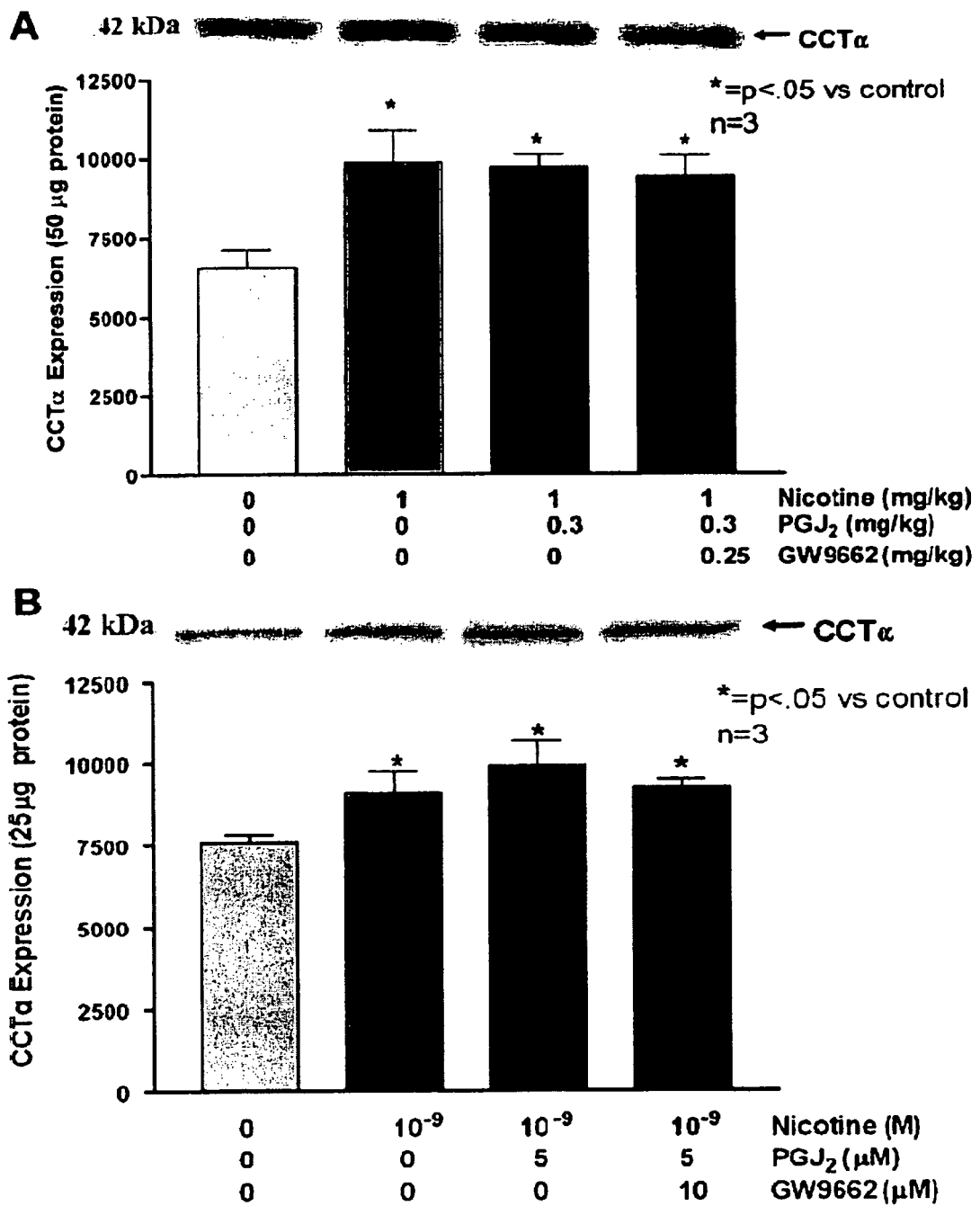

FIG. 20, panels A and B show the effect of nicotine on CTP:choline phosphate cytidylyl-transferase-α (CCT-α) protein expression in ATII cells. CCT-α protein expression by ATII cells increased significantly after in utero (1 mg/kg ip administered to pregnant dam once daily from embryonic day 6 to 20 (Panel A), or in vitro ($1 \times 10^{-9}$ M for 24 h; Panel B) nicotine treatment. Concomitant treatment with $PGJ_2$ or GW9662 had no effect on the nicotine-induced increase in CCT-a protein expression in utero or in vitro. Representative Western blot and density histograms are shown.

Figure 21:
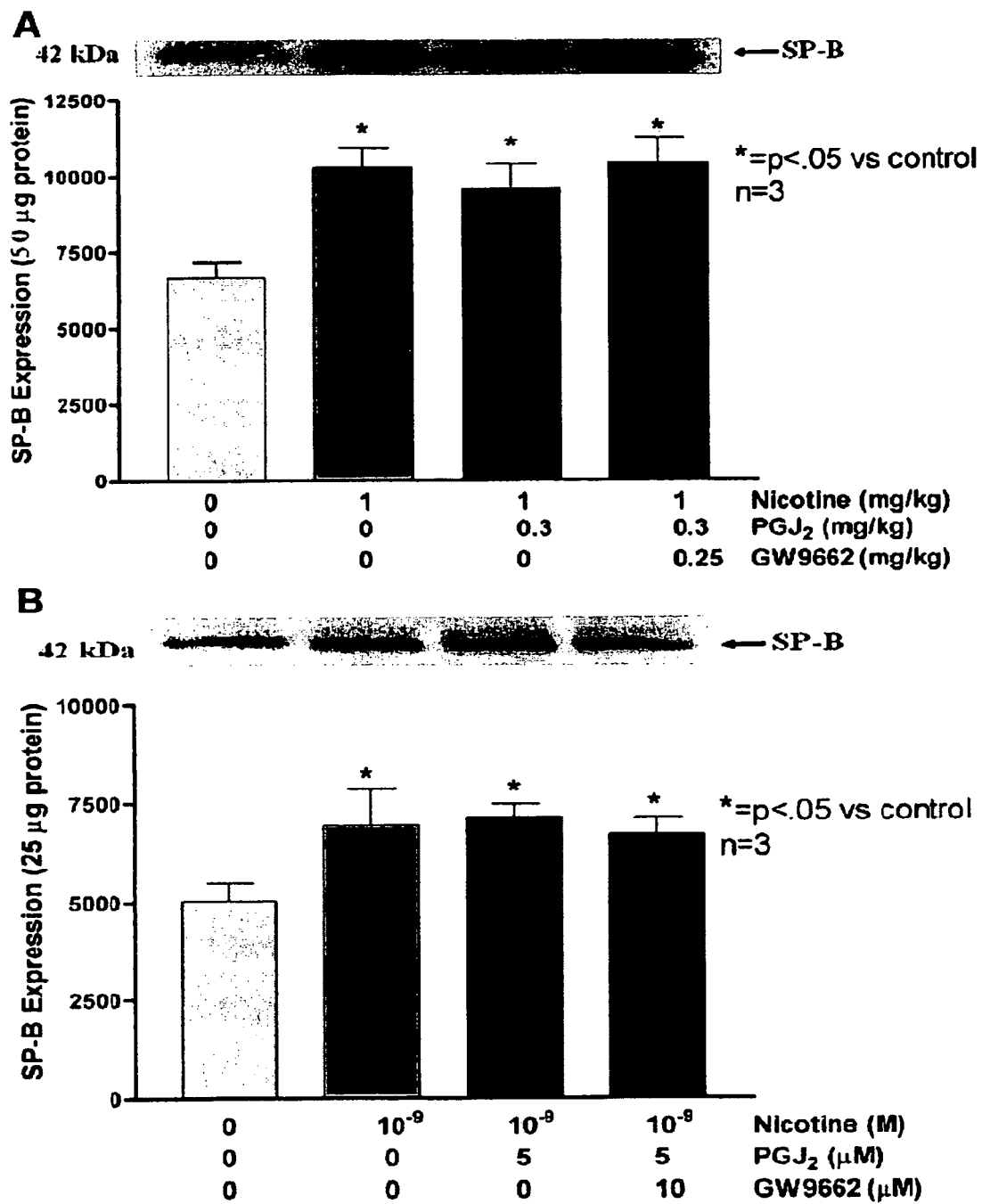

FIG. 21, panels A and B show the effect of nicotine on SP-B expression in ATII cells. SP-B protein expression increased significantly after in utero (1 mg/kg ip administered to pregnant dam once daily from embryonic day 6 to 20; Panel A) or in vitro ($1 \times 10^{-9}$ M for 24 h; Panel B) nicotine treatment. Concomitant treatment with PGJ2 or GW9662 had no effect on the nicotine-induced increase in SP-B protein expression in utero or in vitro. Representative Western blot and density histograms are shown.

Figure 22:
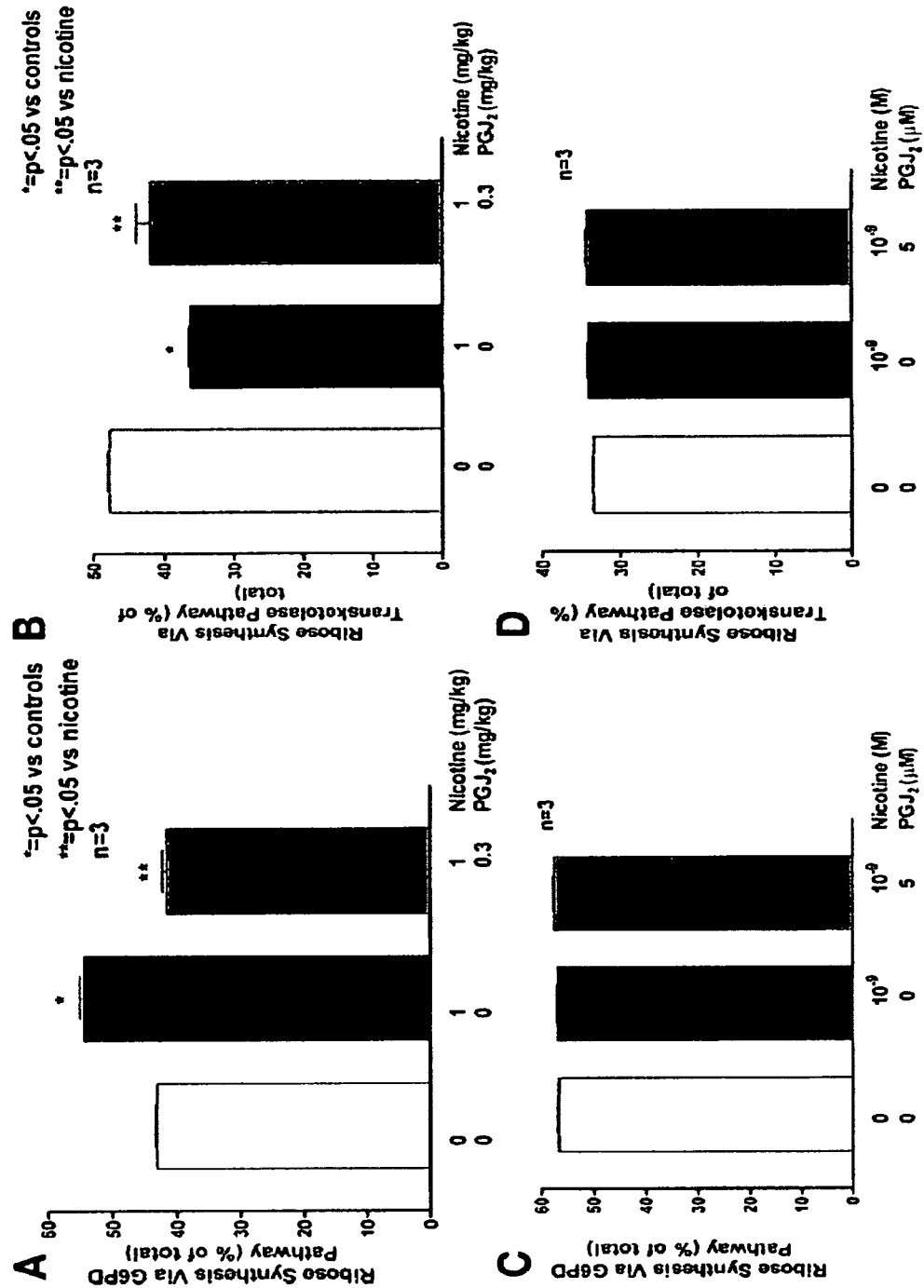

FIG. 22, panels A-D, show the effect of in utero nicotine exposure on ATII cell metabolism. After in utero nicotine exposure (1 mg/kg ip administered to pregnant dam once daily from embryonic day 6 to 20), ribose synthesis, as measured by [$^{13}$C]glucose labeling, increased significantly via the oxidative glucose-6-phosphate dehydrogenase (G6PD) pathway (Panel A) and decreased significantly via the nonoxidative transketolase pathway (Panel B). Concomitant administration of the PPAR-γ agonist $PGJ_2$ completely blocked these changes. Direct in vitro treatment of cultured ATII cells with nicotine did not alter ribose synthesis via the oxidative or nonoxidative pathway with or without PGJ2 (Panels C and D).

Figure 23:
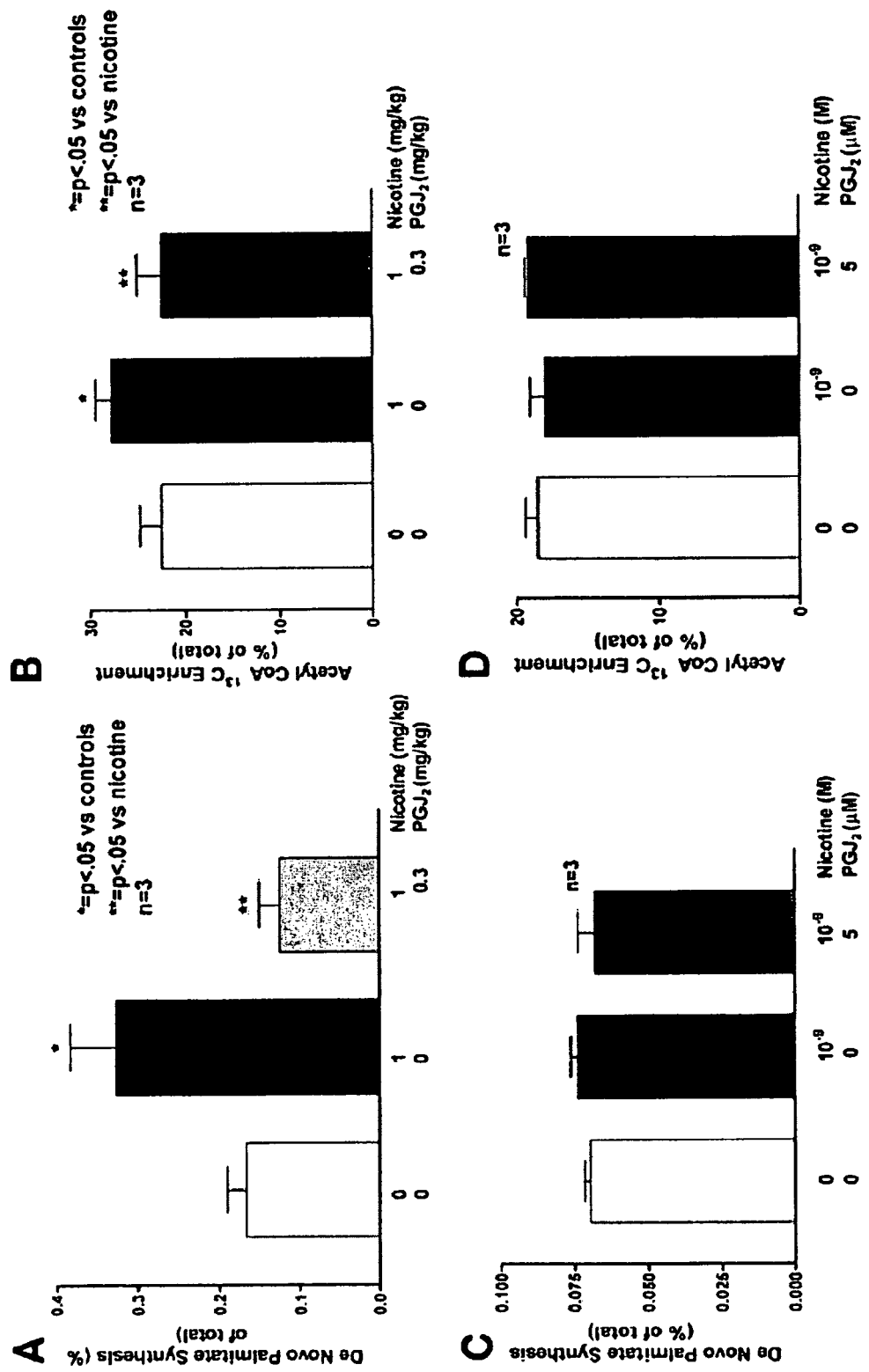

FIG. 23, panels A-D show the effect of nicotine on ATII cell de novo palmitate synthesis. After in utero nicotine exposure (1 mg/kg ip administered to pregnant dam once daily from embryonic day 6 to 20), de novo palmitate synthesis, as a function of total palmitate in ATII cells (Panel A) and [$^{13}$C] glucose labeling of acetyl-CoA pool (Panel B), increased significantly. Concomitant administration of the PPAR-γ agonist $PGJ_2$ completely blocked these changes. Direct in vitro treatment of cultured ATII cells with nicotine did not alter de novo palmitate synthesis or [$^{13}$C]glucose labeling of the acetyl-CoA pool with or without PGJ2 (Panels C and D).

Figure 24:
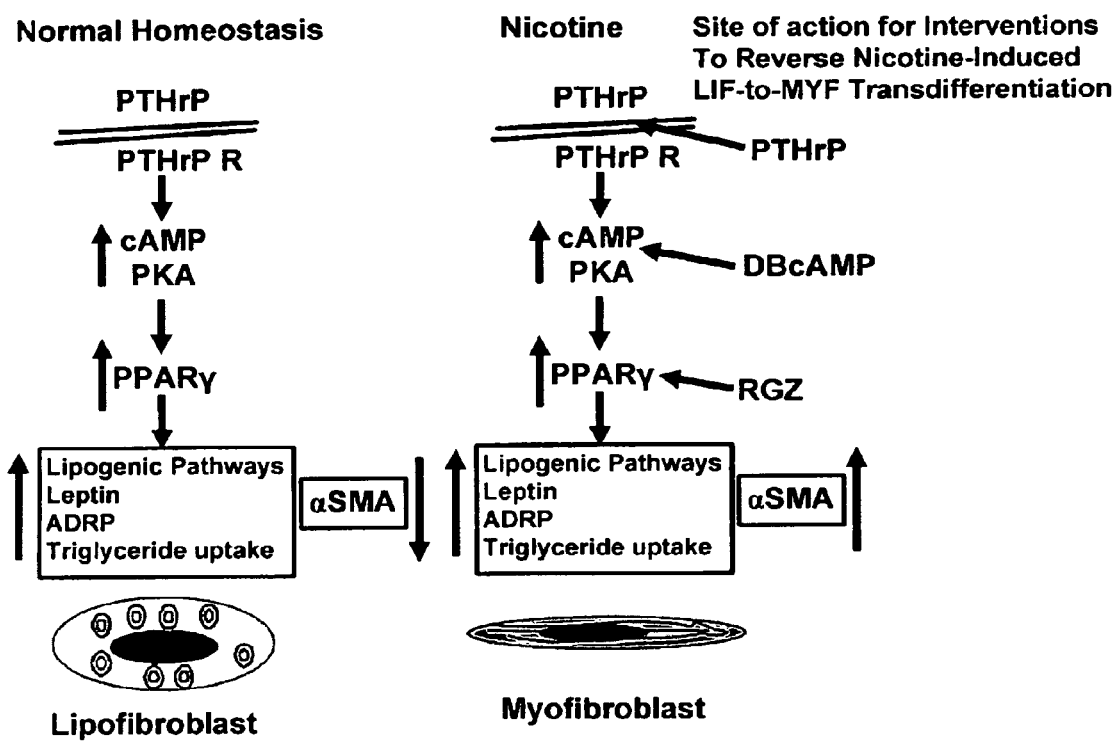
Figure 25:
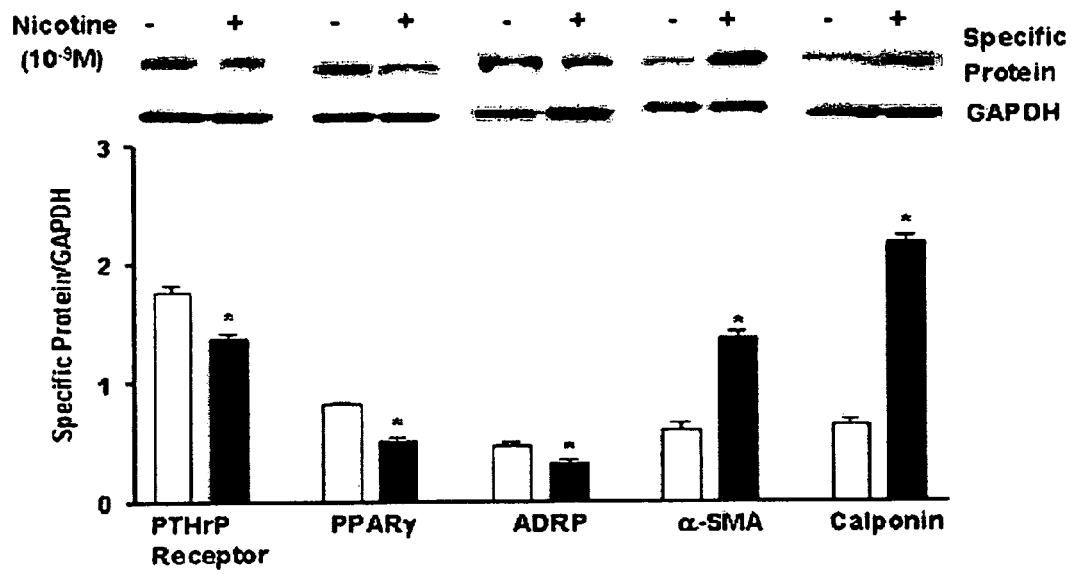

FIG. 24 shows that parathyroid hormone-related protein, secreted by the alveolar type II (ATII) cell, binds to its receptor on the lipofibroblast, activating the cAMP-dependent PKA-mediated lipogenic pathway, upregulating PPARγ and its downstream target, ADRP, which facilitates triglyceride uptake by the lipofibroblast and leptin, which stimulates surfactant phospholipid and protein synthesis by the alveolar type II cell. The triglycerides taken up by the lipofibroblast are then trafficked to the ATII cell as substrate for surfactant phospholipid synthesis. Nicotine exposure downregulates the PTHrP signaling pathway, resulting in LIF-to-MYF transdifferentiation. However, PTHrP signaling pathway agonists [PTHrP, dibutryl cAMP (DBcAMP), and rosiglitazone (RGZ)] can almost completely prevent nicotine-induced LIF-to-MYF transdifferentiation FIG. 25 shows that nicotine treatment of cultured lung fibroblasts for 7 days results in significant decreases in parathyroid hormone-related protein receptor (*$p<0.001$ vs. control; n=3), peroxisome proliferator-activated receptorγ (*$p<0.001$ vs. control; n=3), and adipocyte differentiation-related protein (*$p<0.05$ vs. control; n=3), and significant increases in α smooth muscle actin (*$p<0.001$ vs. control; n=3) and calponin (*$p<0.001$ vs. control; n=3) protein expressions. The values are mean±SD. Representative Western blots and densitometric histograms are shown FIG. 26: Embryonic human lung fibroblasts were initially exposed to nicotine ($10^{-9}$ M) for 7 days and then treated with PPARγ agonists [rosiglitazone (RGZ) ($1 \times 10^{-5}$ M), PTHrP ($5 \times 10^{-7}$ M), or DBcAMP ($1 \times 10^{-5}$ M)] for the following 7 days. Even after nicotine treatment was stopped, PTHrP receptor (a), PPARγ (b), and ADRP (c) expression continued to be significantly lower in the 7d nicotine-only treatment group compared to untreated controls. Treatment with RGZ, PTHrP, or cAMP reversed nicotine-induced decrease in PTHrP receptor expression (a: $<0.05$ vs. control and #$<0.001$ vs. nicotine; n=3), PPARγ (b: *$<0.01$ vs. control and #$<0.05$ vs. nicotine; n=3), and ADRP expression (c: *$<0.01$ vs. control and #$<0.001$ vs. nicotine; n=3). The values are mean±SD and n=3. Representative Western blots and densitometric histograms are shown.

FIG. 27: Embryonic human lung fibroblasts were initially exposed to nicotine ($10^{-9}$M) for 7 days and then treated with PPARγ agonists [rosiglitazone (RGZ) ($1 \times 10^{-5}$ M), PTHrP ($5 \times 10^{-7}$ M), or DBcAMP ($1 \times 10^{-5}$ M)] for the following 7 days. Even after nicotine treatment was stopped, SMA (a) and calponin (b) expression continued to be significantly higher in the 7d nicotine-only treatment group compared to untreated controls. Treatment with RGZ, PTHrP, or DBcAMP reversed nicotine-induced increase in SMA (a: *$p<0.01$ vs. control and #$p<0.001$ vs. nicotine; n=3) and calponin expression (b: *$p<0.001$ vs. control and #$p<0.001$ vs. nicotine; n=3). The values are mean±SD and n=3. Representative Western blots and densitometric histograms are shown.

Figure 28:
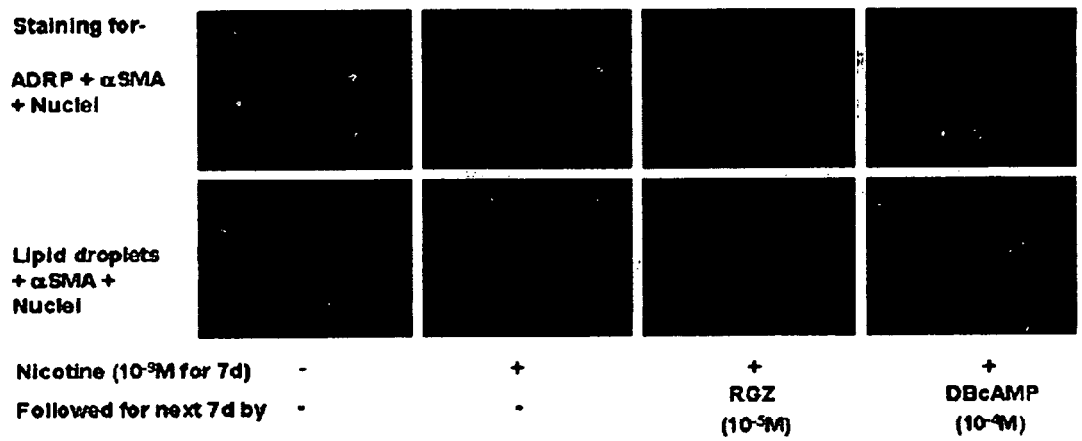

FIG. 28 shows representative immunofluorescence staining for ADRP or lipid droplets (red staining) and SMA (green staining) in cultured WI38 cells under different experimental conditions. Embryonic human lung fibroblasts were maintained in culture in two-well slides either with or without nicotine ($10^{-9}$ M) treatment for 7 days and then treated with PPARγ agonists [rosiglitazone (RGZ) ($1 \times 10^{-5}$ M) or DBcAMP ($1 \times 10^{-5}$ M)] for the following 7 days. The 7d nicotine-only treatment group showed a marked decrease in ADRP and lipid droplet staining and a marked increase in SMA staining compared to untreated controls. Both RGZ and DBcAMP treatments reversed the nicotine-induced decrease in ADRP and lipid droplet staining and an increase in SMA staining.

Figure 29:
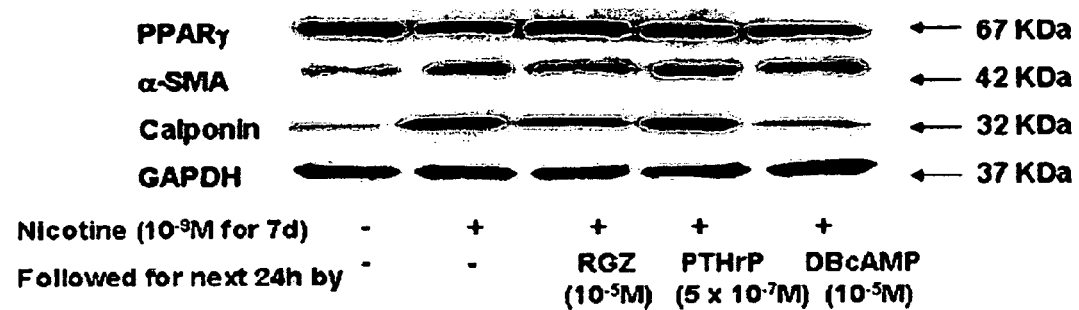
Figure 30:
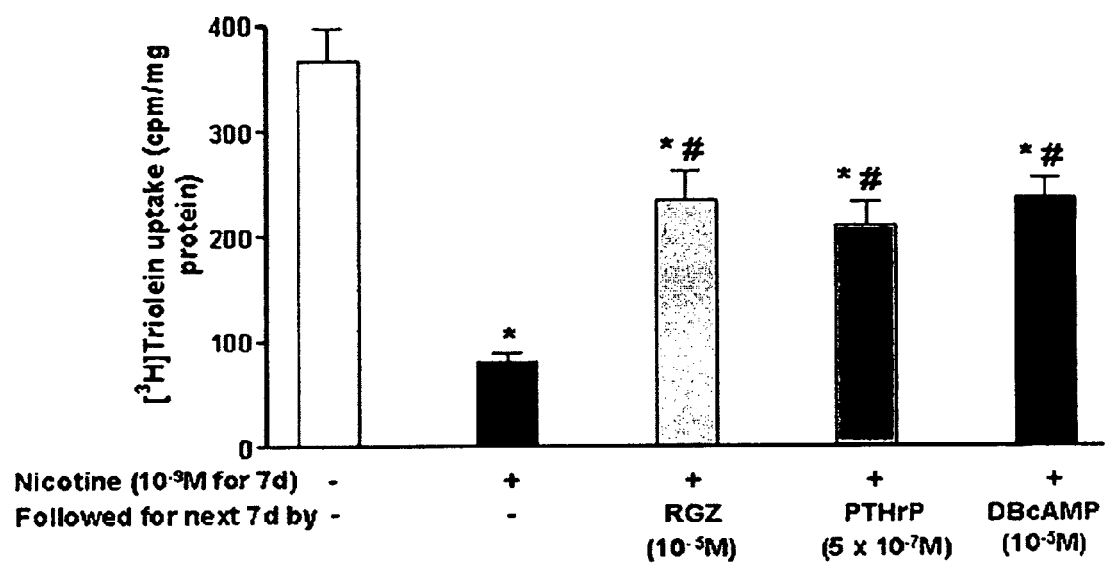

FIG. 29: Embryonic human lung fibroblasts were initially exposed to nicotine ($10^{-9}$ M) for 7 days and then treated with PPARγ agonists [rosiglitazone (RGZ) ($1 \times 10^{-5}$ M), PTHrP ($5 \times 10^{-7}$ M), or DBcAMP ($1 \times 10^{-5}$ M)] for the following 24 h. At the end of 24 h the expression of PPARγ, the key lipogenic nuclear transcription factor, continued to be significantly lower and the expression of SMA and calponin continued to be significantly higher in the 7d nicotine-only treatment group compared to untreated controls. Similar to the 7-day data, there was clear evidence of reversal of nicotine-induced lipofibroblast-to-myofibroblast transdifferentiation even after only 24 h of treatment with PTHrP signaling agonists. Representative Western blots are shown FIG. 30 shows that nicotine treatment of WI38 cells for 7 days resulted in a significant decrease in triolein uptake, which was at least partially blocked by treatment with rosiglitazone (RGZ) (1 only $10^{-5}$ M), PTHrP ($5 \times 10^{-7}$ M), or DBcAMP ($1 \times 10^{-5}$ M), all stimulants of PTHrP signaling pathway, for 7 days (*$p<0.05$ vs. control and *$p<0.05$ vs. nicotine groups for all markers). The values are mean±SD and n=3.

Figure 31:
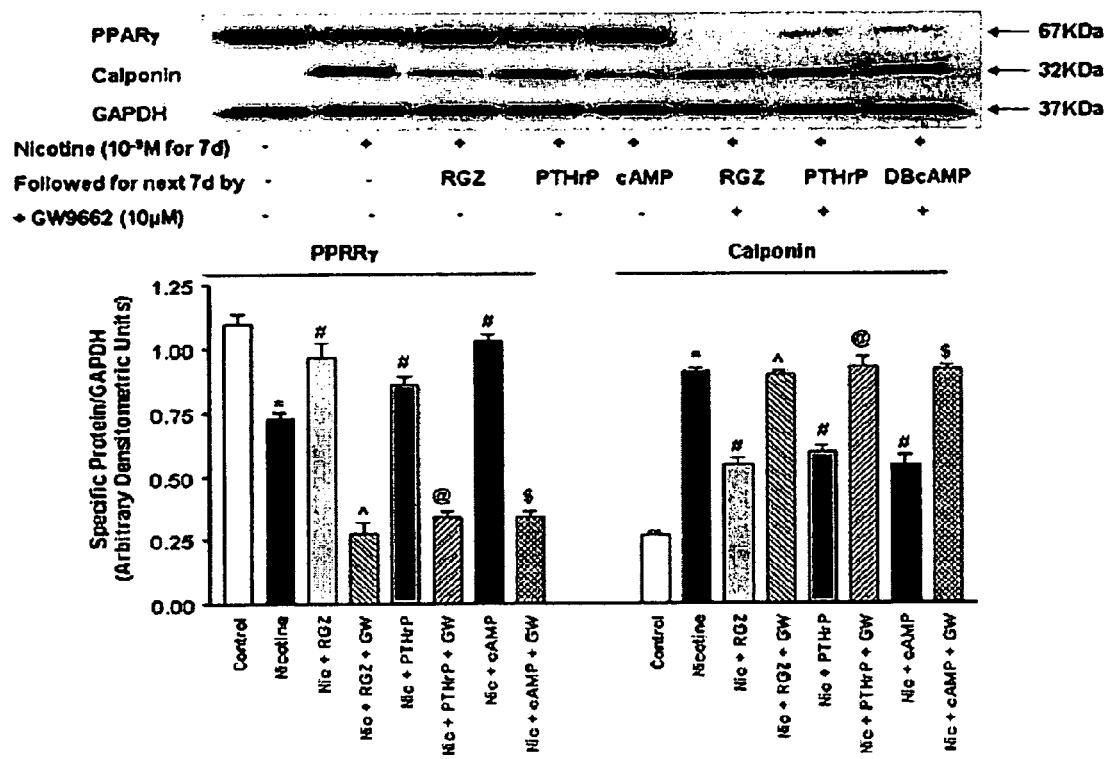

FIG. 31 shows that pretreatment with a specific PPARγy antagonist, GW9662 ($1 \times 10^{-5}$ M), completely blocked the molecular protection (increase in PPARγ and a decrease in calponin expression) against nicotine ($1 \times 10^{-9}$ M for 7 days)-induced lipofibroblast-to-myofibroblast transdifferentiation by all three PTHrP signaling agonists [rosiglitazone (RGZ) ($1 \times 10^{-5}$ M), PTHrP ($5 \times 10^{7}$ M), or DBcAMP ($1 \times 10^{-5}$ M), (*$p<0.001$ vs. control; #$p<0.01$ vs. nicotine; ^$p<0.001$ vs. nicotine+RGZ; @$p<0.001$ vs. nicotine+PTHrP; and $$p<0.001$ vs. nicotine+DBcAMP groups]. The values are mean±SD and n=3.

DETAILED DESCRIPTION

This invention pertains to the discovery of novel methods of treating the effects of nicotine exposure (e.g., smoking) on the mammalian respiratory system. The data presented herein indicate that exposure to nicotine changes the lung interstitium from a predominantly lipogenic phenotype to a myogenic phenotype. The data indicate that down-regulation of Peroxisoine Proliferator-Activated Receptor (PPAR)γ expression in the lung mesenchyme follows in utero nicotine exposure. As PPARγ expression is the key to maintaining the lipogenic phenotype of the mesenchyme, we believe that up-regulating PPARγ nicotine exposure may completely block nicotine-induced pulmonary lipo-to-myofibroblast transdifferentiation.

The understanding of this mechanism provides a variety of targets for specific preventive and therapeutic strategies. In this regard, it is noted that, the decrease in triolein uptake, the functional hallmark of the alveolar interstitial lipofibroblast by nicotine was completely blocked by either tubocurarine or α-bungarotoxin, but not by mecamylamine, suggesting the specific involvement of the $α_7$ nACh receptor subtype in nicotine-induced lipo-to-myofibroblast transdifferentiation.

It is also demonstrated herein that nicotine-induced LIF-to-MYF transdifferentiation can be completely prevented by concomitant treatment with PTHrP, DBcAMP, RGZ, and by transiently overexpressing PPAR. Our data suggest nicotine induces alveolar LIF-to-MYF transdifferentiation through a mechanism involving downregulation of lipogenic PTHrP-mediated, cAMP-dependent PKA signaling pathway, which can be prevented using specific molecular targets.

Thus, for example, in certain embodiments, agents that are PTHrP signaling pathway agonists, e.g., PTHrP and variants or mimetics thereof, dibutryl cAMP and variants or mimetics thereof, and various PPARγ antagonists (e.g., rosiglitazone (RGZ)) can partially or fully block and in some cases reverse, nicotine-induced pulmonary lipo- to myo-fibroblast transdifferentiation. PTHrP signaling agonists agonists thus provide useful agents for treating or preventing nicotine-induced pulmonary damage.

Thus, for example, smokers or non-smokers exposed to smoke can be treated with PPARγ agonists, e.g., $PGJ_2$, thiazolidinedione, and the like (e.g., orally, parenterally, or preferably via aerosolized route) to reduce, prevent and/or reverse nicotine-induced lung disease. It is believed the use of PTHrP signaling agonists agonists will heal the alveoli and increase lung function.

It is also noted that deleterious effect of nicotine on the lung parenchyma may also be mimicked by pulmonary infection as well as exposure to other cyclic hydrocarbons and toxic agents in the environment. Therefore, it is believed that administration of PTHrP signaling agonists can be used to reduce, prevent, or reverse lung damage in these conditions as well.

In addition, it is believed that PTHrP signaling agonists can also be used for prevention of fibrotic injury to pulmonary tissue. Thus, the PTHrP signaling agonists can be used to protect high risk patients, e.g. those who are placed for the first time on mechanical ventilation and/or who are otherwise subjected to hyperoxia.

I. PTHrP Signaling Agonists.

A wide variety of PTHrP signaling agonists are known. Such agents include but are not limited to PTHrP itself along with variants and mimetics (e.g., parathyroid hormone-related protein (1-36), PTHrP-(7-34)$NH_2$, PTHrP singularly substituted with a photoreactive L-p-benzoylphenylalanine (Bpa) at the first N-terminal positions ($Bpa^1$-PTHrP), see, e.g., Behar et al. (2000) *J. Biol. Chem.*, 275(1): 9-17, PTHrP in which residues 5 and/or 23 are switched with the corresponding residues of PTH (see, e.g., U.S. Pat. No. 6,362,163, which is incorporated herein by reference), and the like). Certain PTHrP signaling agonists include, but are not limited to conformationally constrained parathyroid hormone (PTH) analogs and derivatives of those analogs containing PTH polypeptide derivatives containing at least one Glu or Lys substitution at position 6 and/or 10, with, optionally installed, lactam bridges between the side chains of Lys and Glu. Such derivatives include derivatives of PTH (1-34), PTH(1-33), PTH(1-32), PTH(1-31), PTH(1-30), PTH(1-29), PTH(1-28), PTH(1-27), PTH(1-26), PTH(1-25), PTH(1-24), PTH(1-23), PTH(1-22), PTH (1-21), PTH(1-20), PTH(1-19), PTH(1-18), PTH(1-17), PTH(1-16), PTH(1-15), PTH(1-14), PTH(1-13), PTH(1-12), PTH(1-11), PTH(1-10) and PTH(1-9) polypeptide as described in U.S. Patent Publication No: 20060229240, which is incorporated herein by reference.

In certain embodiments the PTHrP signaling agonists comprise one or more PPARγ agonists. A large number of PPARγ agonists are known to those of skill in the art many are clinically approved for certain conditions. In certain embodiments the PPAR gamma agonist is a thiozolidinedione (TZD). In certain embodiments, the PPAR gamma agonist is a glitazone (e.g., troglitazone, (Resulin), rosiglitazone, pioglitazone, ciglitazone, englitazone, darglitazone, and the like), farglitazar, phenylacetic acid, GW590735, GW677954, Avandia, Avandamet (avandia+metformin), 15 deoxy prostaglandin J2 (15PGJ2), 15-deoxy-delta12,14 PGJ2, GW-9662, MCC-555, Muraglitzazr (Bristol-Myers/Merck), Galida tesaglitzazr (AstraZeneca), 677954 (GlaxoSmithKline), MBX-102 (Metabolex), T131 (Tularik), LY818 (Eli Lilly/Ligand Pharmaceutical), LY929 (Eli Lilly/Ligand Pharmaceutical), PLX204 (Plexxikon), and the like. Certain preferred PPAR gamma agonists include, but are not limited to, rosiglitazone or an analogue thereof.

Other suitable PPARγ agonists include, but are not limited to N-(substituted)carbamoylaryl- and heteroaryl substituted aminopropanoic and butanoic acid compounds (see, e.g., U.S. Pat. No. 6,713,514 which is incorporated herein by reference) as well as others (see, e.g., WO 91/07107; WO 92/02520; WO 94/01433; WO 89/08651; JP Kokai 69383/92; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; 5,260,445; 5,814,647, 6,200,998, and U.S. Patent Publications 20030109570, and 2005/0014833, which are all incorporated herein by reference).

In various embodiments the PPAR-gamma agonists can be obtained commercially. Alternatively, they are synthesized from commercially available precursors, and/or purified or isolated from naturally occurring sources by known biochemical means. (see, e.g., U.S. Pat. No. 6,200,998). Synthetic or semi-synthetic versions or derivatives of PPARγ agonists are also useful in the inventive method, as are pharmaceutically acceptable salts of PPARγ agonist compounds associated with various anions and cations, including, for example, succinate, glutamate, maleate, fumarate, sodium, magnesium, calcium, hydrochloride, chloride, sulfate, carbonate, or bicarbonate.

It will be appreciated that in certain instances two or more different PPARγ agonists can be used in the methods described herein. The PPARγ agonists described above are intended to be illustrative and not limiting. Utilizing the teachings provided herein, other PPARγ agonists can be used to inhibit, prevent, or reverse pulmonary damage.

II. Administration of PTHrP Signaling Agonists Prevent, Inhibit, or Reverse Pulmonary Damage.

In certain embodiments, this invention provides methods for the inhibition, prevention, and/or reversal of pulmonary damage, e.g. from smoking, other forms of nicotine exposure, chronic inflammation, and the like.

In certain embodiments, one or more of the conditions described herein are treated increasing the activity of PPARγ (e.g., by upregulating PPARγ and/or PPARγ receptors, etc.). In certain embodiments, this is accomplished simply by administration of one or more PPARγ agonists.

A) Formulations

In certain embodiments in order to carry out the methods of the invention, the PTHrP signaling agonists (e.g., PPARγ agonists) are administered, e.g. to a smoker, to a person exposed to second hand smoke, etc. The agent can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more pathological conditions described herein and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, aerosols, inhalers, nasal sprays, injectibles, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient at risk for or suffering from one or more symptoms of nicotine-induced and/or pollutant induced pulmonary disease." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively prevent, ameliorate, or reverse one or more symptoms of pulmonary damage and/or dysfunction.

In certain preferred embodiments, the active agents of this invention are administered via inhalation (e.g., as an aerosol), parenterally, orally (e.g. via a lozenge, tablet, capsule, etc.) or as an injectable in accordance with standard methods well known to those of skill in the art. In certain embodiments the PPARγ agonists can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch can contain a single reservoir, or it can contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In another embodiment, one or more components of the solution can be provided as a "concentrate", e.g., in a storage container (e.g., in a premeasured volume) ready for dilution, or in a soluble capsule ready for addition to a volume of water.

The pharmaceutically acceptable compositions in accordance with the method of the present invention can be formulated and manufactured at more than one concentration of PPARγ agonist, such that modular increments of PPARγ agonist can be easily administered within the preferred dose range for the particular mammal. In general, the preferred effective dose range of PPARγ agonists, in accordance with the preferred method, is well below toxic levels.

The foregoing formulations and administration methods are intended to be illustrative and not limiting. It will be appreciated that, using the teaching provided herein, other suitable formulations and modes of administration can be readily devised.

B) Effective Dosages.

The PTHrP signaling agonists (e.g., PPARγ agonists) will generally be used in an amount effective to achieve the intended purpose (e.g., to prevent, reduce, or reverse nicotine-induced pulmonary damage and the like). In certain embodiments the agent(s) utilized in the methods of this invention are administered at a dose that is effective to partially or fully prevent, inhibit, or reverse nicotine-induced lung damage. In certain instances, such a dosage is comparable to the dosage that partially or fully inhibits the transdifferentiation of lipofibroblasts to myofibroblasts in an otherwise normal mammal subject to hyperoxic conditions (e.g., a statistically significant decrease at the 90%, more preferably at the 95%, and most preferably at the 98% or 99% confidence level). The compounds can also be used prophalactically at the same dose levels.

Typically, the PTHrP signaling agonists (e.g., PPARγ agonists) are administered or applied in a therapeutically effective amount. A therapeutically effective amount is an amount effective to reduce or prevent one or more symptoms characteristic of nicotine-induced pulmonary damage. Determination of a therapeutically effective amount is well within the capabilities of those skilled in the art, especially in light of the detailed disclosure provided herein. Thus, for example, in certain embodiments, a therapeutically effective amount of a PPAR gamma ligand (e.g., rosiglitazone) varies from about 0.1 mg/kg to about 100 mg/kg, preferably from about 1 mg/kg to about 25 or 50 mg/kg, most preferably from about 3 mg/kg to about 20 mg/kg.

In certain embodiments, an initial dosage of about 1 mg/kg daily, preferably from about 1 mg to about 1000 mg per kilogram daily will be effective. Daily dose ranges can include about 3 mg/kg to about 100 mg/kg is preferred, preferably about 3 mg/kg to about 50 mg/kg, and more preferably about 3 mg/kg to about 25 or 10 mg/kg. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One skilled in the art could readily optimize administration to humans based on animal data.

Dosage amount and interval may be adjusted individually to provide plasma levels of the inhibitors which are sufficient to maintain therapeutic effect.

Dosages for typical therapeutics, particularly for PPARγ agonists, are known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In cases of local administration or selective uptake, the effective local concentration of the inhibitors may not be related to plasma concentration. One skilled in the art will be able to optimize therapeutically effective local dosages without undue experimentation. The amount of inhibitor administered will, of course, be dependent on the subject being treated, on the subject's weight, the severity of the affliction, the manner of administration and the judgment of the prescribing physician.

The therapy may be repeated intermittently. The therapy may be provided alone or in combination with other drugs and/or procedures.

C) Toxicity.

Preferably, a therapeutically effective dose of the PTHrP signaling agonists (e.g., PPARγ agonists) described herein will provide therapeutic benefit without causing substantial toxicity.

Toxicity of the PPARγ agonists described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). It is noted that toxicity of numerous PPARγ agonists ligands is well characterized. The dose ratio between toxic and therapeutic effect is the therapeutic index. Inhibitors which exhibit high therapeutic indices are preferred. The data obtained from these cell culture assays and animal studies can be used in formulating a dosage range that is not toxic for use in human. The dosage of the inhibitors described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al. (1975) In: *The Pharmacological Basis of Therapeutics*, Ch. 1, p. 1).

III. Screening for Agents that Inhibit, Prevent, or Reverse Nicotine-induced Pulmonary Damage.

As indicated above, in one aspect, this invention pertains to the discovery of a mechanism of nicotine-induced pulmonary damage and that PTHrP signaling agonists (e.g., PPARγ agonists) can inhibit, prevent, and/or reverse such damage. Thus methods of screening for PPARγ agonists provide good methods for screening for agents that can inhibit, prevent, and/or reverse nicotine-induced pulmonary damage.

When screening for PPARγ agonists, a positive assay result need not indicate that a particular test agent is a good pharmaceutical. Rather a positive test result can simply an indicator that the tested compound is a good potential agent and/or can serve as a lead compound in the development of other clinically relevant agonists.

Using known activities, and/or nucleic acid sequences, and/or amino acid sequences of PTHrP, PPARγ and/or the PPARγ receptor, expression level(s) and/or activity of a test compound can readily be determined according to a number of different methods, e.g., as described below. In particular, expression levels of PPARγ and/or PPARγ receptors can be altered by changes in the copy number of the gene(s) encoding those components, and/or by changes in the transcription of the gene product (i.e. transcription of mRNA), and/or by changes in translation of the gene product (i.e. translation of the protein), and/or by post-translational modification(s) (e.g. protein folding, glycosylation, etc.). Thus useful assays of this invention include assaying for copy number, level of transcribed mRNA, level of translated protein, activity of translated protein, etc.

A) Nucleic-acid Based Assays.

1) Target Molecules.

Changes in expression level(s) of PTHrP signaling pathway components, e.g., PPARγ and/or the PPARγ receptor can be detected by measuring changes in mRNA encoding such component(s) and/or a nucleic acid derived from the mRNA (e.g. reverse-transcribed cDNA, etc.). In order to measure the expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism, or from cells in culture. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) *Chapter 3 of Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using $(dT)_n$ magnetic beads (see, e.g., Sambrook et al., (1989) *Molecular Cloning: A Laboratory Manual* (2nd ed.), Vols. 1-3, Cold Spring Harbor Laboratory, or *Current Protocols in Molecular Biology*, F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g., Innis, et al., (1990) *PCR Protocols. A guide to Methods and Application. Academic Press*, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In certain embodiments, where it is desired to quantify the transcription level (and thereby expression) of PPAR gamma and/or the PPAR gamma receptor in a sample, the nucleic acid sample is one in which the concentration of the mRNA transcript(s), or the concentration of the nucleic acids derived from the mRNA transcript(s), is proportional to the transcription level (and therefore expression level) of the gene(s) of interest. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the nucleic acid sample is the total mRNA or a total cDNA isolated and/or otherwise derived from a biological sample (e.g. a neurological cell or tissue). The nucleic acid may be isolated from the sample according to any of a number of methods well known to those of skill in the art as indicated above.

2) Hybridization-based Assays.

Using the known sequences for PPAR gamma and/or the PPAR gamma receptor, detecting and/or quantifying the transcript(s) can be routinely accomplished using nucleic acid hybridization techniques (see, e.g., Sambrook et al. supra). For example, one method for evaluating the presence, absence, or quantity of reverse-transcribed cDNA involves a "Southern Blot". In a Southern Blot, the DNA (e.g., reverse-transcribed mRNA), typically fragmented and separated on an electrophoretic gel, is hybridized to a probe specific for subject nucleic acid(s) (or to a mutant thereof). Comparison of the intensity of the hybridization signal from the probe with a "control" probe (e.g. a probe for a "housekeeping gene) provides an estimate of the relative expression level of the target nucleic acid.

Alternatively, the mRNA of interest can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target PPAR gamma and/or the PPAR gamma receptor mRNA. Appropriate controls (e.g., probes to housekeeping genes) provide a reference for evaluating relative expression level.

An alternative means for determining the expression level(s) of PPAR gamma and/or the PPAR gamma receptor is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-based Assays.

In another embodiment, amplification-based assays can be used to measure expression (transcription) level of PTHrP signaling pathway components e.g., PPAR gamma and/or the PPAR gamma receptor. In such amplification-based assays, the target nucleic acid sequences (PPAR gamma and/or the PPAR gamma receptor nucleic acids) act as template(s) in amplification reaction(s) (e.g. Polymerase Chain Reaction (PCR) or reverse-transcription PCR(RT-PCR)). In a quantitative amplification, the amount of amplification product will be proportional to the amount of template in the original sample. Comparison to appropriate (e.g. tissue or cells unexposed to the test agent) controls provides a measure of the target transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One typical internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al. (1990) Academic Press, Inc. N.Y. The known nucleic acid sequence(s) for PPAR gamma and/or the PPAR gamma receptor are sufficient to enable one of skill to routinely select primers to amplify any portion of the gene(s).

4) Hybridization Formats and Optimization of Hybridization Conditions.

i) Array-based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high-density arrays is also described in U.S. Pat. Nos. 5,744,305, 5,800,992 and 5,445,934.

ii) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands that bind to labeled antibodies, fluorophores, chemi-luminescent agents, enzymes, and antibodies that can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

ii) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.).

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13: 105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy.

The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

iv) Labeling and Detection of Nucleic Acids

The probes used herein for detection of PPARγ and/or the PPARγ receptor expression levels can be full length or less than the full length of the target nucleic acid. Shorter probes are empirically tested for specificity. Preferred probes are sufficiently long so as to specifically hybridize with the target nucleic acid(s) under stringent conditions. The preferred size range is from about 10, 15, or 20 bases to the length of the target mRNA, more preferably from about 30 bases to the length of the target mRNA, and most preferably from about 40 bases to the length of the target mRNA. The probes are typically labeled, with a detectable label as described above.

B) Detection of Expressed Protein

1) Assay Formats.

In addition to, or in alternative to, the detection of PTHrP signaling pathway components, e.g., PPAR gamma and/or the PPAR gamma receptor nucleic acid(s), alterations in expression of PPAR gamma and/or the PPAR gamma receptor can be detected and/or quantified by detecting and/or quantifying the amount and/or activity of translated PPAR gamma protein and/or the PPAR gamma receptor protein(s).

The expression of PPAR gamma and/or the PPAR gamma receptor can be detected and quantified by any of a number of methods well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, the PPAR gamma and/or the PPAR gamma receptor are detected/quantified in an electrophoretic protein separation (e.g., a 1- or 2-dimensional electrophoresis). Means of detecting proteins using electrophoretic techniques are well known to those of skill in the art (see generally, R. Scopes (1982) Protein Purification, Springer-Verlag, N.Y.; Deutscher, (1990) Methods in Enzymology Vol. 182: Guide to Protein Purification, Academic Press, Inc., N.Y.).

In another embodiment, Western blot (immunoblot) analysis is used to detect and quantify the presence of PPAR gamma and/or the PPAR gamma receptor in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target member, e.g., polypeptide(s), and can be directly labeled or alternatively may be subsequently detected using labeled antibodies (e.g., labeled sheep anti-mouse antibodies) that specifically bind to a domain of the antibody.

In certain embodiments, the PPAR gamma and/or the PPAR gamma receptor are detected using an immunoassay. As used herein, an immunoassay is an assay that utilizes an antibody to specifically bind to the analyte (e.g., the target polypeptide(s), such as PPAR gamma and/or the PPAR gamma receptor). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) Methods in Cell Biology Volume 37: Antibodies in Cell Biology, Academic Press, Inc. New York; Stites & Terr (1991) Basic and Clinical Immunology 7th Edition.

Immunological binding assays (or immunoassays) typically utilize a "capture agent" to specifically bind to and often immobilize the analyte (e.g., PPAR gamma and/or the PPAR gamma receptor). In certain embodiments, the capture agent is an antibody.

Immunoassays also often utilize a labeling agent to specifically bind to and, label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542).

Typical immunoassays for detecting the target polypeptide(s), e.g., PPAR gamma and/or the PPAR gamma receptor, are either competitive or noncompetitive. Noncompetitive immunoassays are assays in which the amount of captured analyte is directly measured. In one "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (e.g., PPAR gamma and/or the PPAR gamma receptor) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one embodiment, the antibody is immobilized on a solid substrate. The amount of target polypeptide bound to the antibody may be determined either by measuring the amount of target polypeptide present in a polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind PPAR gamma and/or the PPAR gamma receptor, either alone or in combination. In the case where the antibody that binds a PPAR gamma and/or the PPAR gamma receptor is not labeled, a different detectable marker, for example, an enzyme-labeled antibody capable of binding to the monoclonal antibody which binds the PPAR gamma and/or the PPAR gamma receptor, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds PPAR gamma and/or the PPAR gamma receptor is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein can be routinely produced as described below.

2) Antibodies to PTHrP Signaling Pathway Components (e.g., PPAR Gamma and/or the PPAR Gamma Receptor.

Either polyclonal or monoclonal antibodies can be used in the immunoassays of the invention described herein. Polyclonal antibodies are typically raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for target polypeptides, such as PPAR gamma and/or the PPAR gamma receptor. If desired, the immunizing peptide can be coupled to a carrier protein by conjugation using techniques that are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are known in the art (see, e.g., *Methods of Enzymology,* "*Production of Antisera With Small Doses of Immunogen: Multiple Intradermal Injections*", Langone, et al. eds. (Acad. Press, 1981)). Polyclonal antibodies produced by the animals can be further purified, for example, by binding to and elution from a matrix to which the peptide to which the antibodies were raised is bound Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology,* Wiley Interscience).

In certain embodiments, however, the antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and F(ab')$^2$, and/or single-chain antibodies (e.g. scFv) which are capable of binding an epitopic determinant.

The general method used for production of hybridomas secreting mAbs is well known (Kohler and Milstein (1975) *Nature,* 256:495). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

Antibody fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature,* 348: 552-554; Hoogenboom et al. (1991) *Nucleic Acids Res.* 19: 4133-4137).

Since the antibody fragments on the surface of the phage are functional, phage bearing antigen binding antibody fragments can be separated from non-binding phage by antigen affinity chromatography (McCafferty et al. (1990) *Nature*, 348: 552-554). Depending on the affinity of the antibody fragment, enrichment factors of 20 fold –1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552-554). Thus even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581-597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581-597; Marks et al. (1993). *Bio/Technology*. 10: 779-783; Griffiths et al. (1993) *EMBO J.* 12: 725-734; Clackson et al. (1991) *Nature*. 352: 624-628). Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Assays for Activity

Another aspect of the invention is a method of assaying a compound that increases PTHrP signaling, e.g., activates/agonizes PPARγ, by for example, increasing PPARγ activity (e.g., by inhibition of Egr-1 expression, etc.). Methods of detecting PPARγ activity are known to those of skill in the art. For example, screening methods utilizing animal cells having introduced therein reporter plasmid(s) containing a reporter gene linked to a PPAR expression vector and a PPAR response element (PPRE), are described in PCT Publication WO 96/22884 and by Tontonoz et al. (1994) *Genes and Development*, 8: 1224-1234, which are incorporated herein by reference. Another approach utilizes animal cells having introduced therein a vector for expressing fused protein in which the DNA binding domain of GAL4 (a yeast transcription factor) and the ligand binding domain of PPAR linked together, along with an introduced reporter plasmid containing a reporter gene linked to the response element of GAL4 (GAL4 binding element), see, e.g., PCT Publication WO 96/33724; Lehmann et al. (1995) *J. Biol. Chem.*, 270: 12953-12956; Willson et al. (1996) *J. Med. Chem.*, 39: 665-668 which are incorporated herein by reference. Another method for directly detecting the binding between PPARγ and a ligand without using any animal cell or reporter gene examined binding and antagonism between a fused protein comprising the ligand binding domain of PPARγ and glutathione-S-transferase (GST) and a test compound labeled with a radioisotope (see, e.g., Willson et al. (1996) *J. Med. Chem.*, 39: 665-668; Buckle et al. (1996) *Bioorganic & Medical Chemistry Letters* 6: 2121-2126 which are incorporated herein by reference). Other suitable assays are described by Krey et al., (1997) *Mol. Endocrinol.*, 11: 779-791 and are shown in U.S. Patent Publication 2002/0119499, which are incorporated herein by reference These PPARγ activity assays described herein are intended to be illustrative and not limiting. Using the teachings provided herein, PPARγ activity assays to identify compounds useful to reduce, prevent, or reverse nicotine-induced pulmonary damage will be known to those of skill in the art.

D) Assay Optimization.

The assays described herein can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred isolation conditions), antibody conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration.

Routine selection and optimization of assay formats is well known to those of ordinary skill in the art.

E) Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control. In certain embodiments, the change is a statistically significant change, e.g. as determined using any statistical test suited for the data set provided (e.g. t-test, analysis of variance (ANOVA), semi-parametric techniques, non-parametric techniques (e.g. Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level). In certain embodiments, the change is at least a 10% change, preferably at least a 20% change, more preferably at least a 50% change and most preferably at least a 90% change.

IV. Agents for Screening: Combinatorial Libraries (e.g., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487-493, Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.,* 114: 9217-9218), analogous organic syntheses of small compound libraries (Chen et al. (1994) *J. Amer. Chem. Soc.,* 116: 2661), oligocarbamates (Cho, et al., (1993) *Science,* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539, 083) antibody libraries (see, e.g., Vaughn et al. (I 996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) *C&EN,* January 18, page 33, isoprenoids U.S. Pat. No. 5,569, 588, thiazolidinones and metathiazanones U.S. Pat. No. 5,549,974, pyrrolidines U.S. Pat. Nos. 5,525,735 and 5,519, 134, morpholino compounds U.S. Pat. Nos. 5,506,337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

XI. High Throughput Screening

Any of the assays described herein are amenable to high-throughput screening (HTS). Moreover, the cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for hybridization assays, immunoassays, and for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

XII. Candidate Agent Databases.

In certain embodiments, the agents that score positively in the assays described herein (e.g. act as PPARγ agonists) can be entered into a database of putative and/or actual agents to inhibit, prevent, or referse nicotine-induced pulmonary damage. The term database refers to a means for recording and retrieving information. In certain embodiments the database also provides means for sorting and/or searching the stored information. The database can comprise any convenient media including, but not limited to, paper systems, card systems, mechanical systems, electronic systems, optical systems, magnetic systems or combinations thereof. Typical databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

XIII. Kits.

In another embodiment, this invention provides kits for the screening procedures and/or diagnostic procedures and/or treatment procedures described herein. Screening/diagnostic kits typically comprise one or more reagents that specifically bind to the target that is to be screened (e.g. PPARγ and/or PPARγ receptor).

"Therapeutic" kits typically comprise a container containing one or more modulators of the PPARγ expression or activity and/or PPARγ receptor expression and/or activity.

In addition, the kits optionally include labeling and/or instructional materials providing directions (i.e., protocols) for the practice of the methods or use of the "therapeutics" or "prophylactics" of this invention. Preferred instructional materials describe the use of one or agents of this invention to inhibit, reverse, or prevent damage to pulmonary tissue (e.g. from smoking or other pathologies). The instructional materials can also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Mechanism of Nicotine-induced Pulmonary Fibroblast Transdifferentiation

In this example, we tested the hypothesis that in vitro nicotine exposure disrupts specific epithelial-mesenchymal paracrine signaling pathways and results in pulmonary interstitial lipofibroblast (LIF)-to-myofibroblast (MYF) transdifferentiation, resulting in altered pulmonary development and function. Studies were done to determine whether nicotine induces LIF-to-MYF transdifferentiation and to elucidate underlying molecular mechanism(s) involved and to determine whether nicotine-induced LIF-to-MYF transdifferentiation could be prevented by stimulating specific alveolar interstitial fibroblast lipogenic pathway. WI38 cells, a human embryonic pulmonary fibroblast cell line, were treated with nicotine with or without specific agonists of alveolar fibroblast lipogenic pathway, PTHrP, DBcAMP, or the potent PPAR stimulant rosiglitazone (RGZ) for 7 days. Expression of key lipogenic and myogenic markers was examined by RT-PCR, Western hybridization, and immunohistochemistry. The effect of nicotine on triglyceride uptake by WI38 cells and PTHrP binding to its receptor was also determined. Finally, the effect of transfecting WI38 cells with a PPAR expression vector on nicotine-induced LIF-to-MYF transdifferentiation was determined. Nicotine treatment resulted in significantly decreased expression of lipogenic and increased expression of myogenic markers in a dose-dependent manner, indicating nicotine-induced LIF-to-MYF transdifferentiation. This was accompanied by decreased PTHrP receptor binding to its receptor. The nicotine-induced LIF-to-MYF transdifferentiation was completely prevented by concomitant treatment with PTHrP, DBcAMP, RGZ, and by transiently overexpressing PPAR. Our data suggest nicotine induces alveolar LIF-to-MYF transdifferentiation through a mechanism involving downregulation of lipogenic PTHrP-mediated, cAMP-dependent PKA signaling pathway, which can be prevented using specific molecular targets.

Materials and Methods.

Reagents

Nicotinic acetylcholine (nACh) receptor antagonists (D-tubocurarine, a-bungarotoxin, and mecamylamine) and dibutyryl cAMP (DBcAMP) were acquired from Sigma (St. Louis, Mo.). PTHrP-(1-34) was obtained from Bachem (Torrance, Calif.), and rosiglitazone maleate (RGZ) was from SmithKline Beecham Pharmaceuticals. nACh receptors $\alpha_3$ and $\alpha_7$ antibodies were obtained from Santa Cruz Biotechnology (Santa Cruz, Calif.). The PPAR expression vector (pCMX-PPARγ) was kindly provided by Dr. P. Tontonoz (Univ. of California Los Angeles).

Cell Culture

The human embryonic cell line WI38 was obtained from American Type Culture Collection (Rockville, Md.). Cells were grown in MEM plus 10% FBS at 37° C. in six-well plates, four-well slides, and 60- and 100-mm culture dishes as needed. At 70-80% confluence, the cells were treated with nicotine ($1\times10^{-9}$ or $1\times10^{-6}$ M) with or without the specific agonists of the alveolar fibroblast lipogenic pathway: PTHrP ($1\times10^{-7}$ M or $5\times10^{-7}$ M), DBcAMP ($1\times10^{-5}$ M or $1\times10^{4}$ M), or the potent PPAR stimulant RGZ ($1\times10^{6}$ M or $1\times10^{-5}$ M). Medium containing fresh chemicals was added daily, and at the end of 7 days, the cells were processed as needed.

Triglyceride Uptake Assay

The method used to quantitate triglyceride uptake by fetal rat lung fibroblasts has been described previously (Torday et al. (1995) *Biochim Biophys Acta* 1254: 198-206). Briefly, culture medium was replaced with DMEM containing 20% adult rat serum mixed with [3H]triolein (5 µCi/ml). The cells were incubated at 37° C. in 5% $CO_2$+balance air for 4 h. At the termination of the incubation, the medium was decanted, the cells were rinsed twice with 1 ml of ice-cold MEM, and the cells were removed from the culture plate after a 5- to 10-min incubation with 2 ml of a 0.05% trypsin solution. An aliquot of the cell suspension was taken for protein assay (Bradford (1976) *Anal Biochem* 72: 248-254), and the remaining cell suspension was extracted for neutral lipid content.

PTHrP Receptor Binding Assay

The receptor binding assay was carried out as previously described (Torday and Rehan (2002) *Am. J. Physiol. Lung Cell Mol. Physiol.* 283: L130-L135; Torday and Rehan (2003) *Cell Biochem Biophys* 37: 235-246). The assay mixture, in a total volume of 0.1 ml, contained 50 mM Tris.HCl (pH 7.4), 2 mM dithiothreitol, 10 mM EDTA, 10 µg/ml each of protease inhibitors (leupeptin, pepstatin, antipain, and aprotinin), 0.5 mM phenylmethylsulfonyl fluoride, 10 mg/ml BSA, 5 mM $MgCl_2$, 10-500 µmol [1251]-Tyr34-PTHrP-(1-

34) (specific activity 1,064 Ci/mmol), 10-12 µg membrane protein, and $1\times10^{-10}$ to $1\times10^{-6}$ M PTHrP-(1-34). Triplicate samples were incubated for 30 min at 30° C. Reactions were stopped by the addition of 0.1 ml of homogenization buffer containing 20 mg/ml of BSA and placed in ice-cold water for 30 min, followed by centrifugation at 15,000 g for 1 min. The supernatant was aspirated, and the pellet was counted for radioactive content with a gamma counter (model 1470; Wallace, Gaithersburg, Md.). Nonspecific binding was determined in the presence of 1 µM nonradioactive PTHrP-(1-34). Specific binding of [$^{125}$I]-Tyr34-PTHrP-(1-34) was calculated as total binding minus nonspecific binding and expressed as femtomoles per milligrams of protein. Specificity of binding was determined in the presence of 1 µM PTHrP-(7-34) amide, a selective PTHrP receptor antagonist, showing that it inhibited the binding of the radioactive ligand. In preliminary studies, the binding was found to be linear with time for up to 60 min of incubation. The effect of nicotine ($1\times10^{-6}$ M) on PTHrP receptor binding was examined without and with the nACh receptor antagonists D-tubocurarine, α-bungarotoxin, or mecamylamine ($1\times10^{-9}$ to $1\times10^{-6}$ M).

Isolation of Total Cellular RNA

Total RNA was isolated by lysing the cells in 4 M guanidinium thiocyanate followed by extraction with 2 M sodium acetate (pH 4.0), phenol, and chloroform/isoamyl alcohol. RNA was precipitated with isopropanol, collected by centrifugation, vacuum dried, and then dissolved in diethylpyrocarbonate-treated water (Chomzynski and Sacchi (1987) *Anal Biochem* 162: 156-159). Integrity of RNA was assessed from the visual appearance of the ethidium bromide-stained ribosomal RNA bands following fractionation on a 1.2% (wt/vol) agarose-formaldehyde gel and quantitated by absorbance at 260 nm.

Semiquantitative RT-PCR

RT-PCR probes used included PTHrP receptor: 5'-ATG TGG ATG TAG TTG COC GTG CAG T-3' (SEQ ID NO:1) and 3'-GGG AAG CCC AGG AAA GAT AAG GCA T-5' (SEQ ID NO:2) (445 bp); PPAR: 5'-CCC TCA TGG CAA TTG AAT GTC GTG (SEQ ID NO:3) and 3'-TCG CAG GCT CTT TAG AAA CTC CCT-5' (SEQ ID NO:4) (757 bp); ADRP: 5'-GTT GCA GTT GAT CCA CAA CCG-3' (SEQ ID NO:5) and 3'-TGG TAG ACA GGG ATC CCA GTC-5' (SEQ ID NO:6) (666 bp); -smooth muscle actin (-SMA): 5'-CGC AAA TAT TCT GTC TGG ATC G-3' (SEQ ID NO:7) and 3'-TCA CAG TTG TGT GCT AGA GAC A-5' (SEQ ID NO:8) (167 bp); nACh receptor 3: 5'-AGG CTA CAA ACA CGA CAT CAA GTA-3' (SEQ ID NO:9) and 3'-TGG CTT CTT TGA TTT CTG GTG ACA-5' (SEQ ID NO:10) (694 bp); nACh receptor 7: 5'-GGC TTC CGC GGC CTG GAC GGC GTG CAC TGT-3' (SEQ ID NO: 11) and 3'-GGC TTC CGC GGC CTG GAC GGC GTG CAC TGT-5' (SEQ ID NO:12) (596 bp); and 18s: 5'-TTA AGC CAT GCA TGT CTA AGT AC-3' (SEQ ID NO: 13) and 3'-TGT TAT TTT TCG TCA CTA CCT CC-5' (SEQ ID NO:14) (489 bp). cDNA was synthesized from 1 µg of total RNA by RT using 100 units of SuperScript reverse transcriptase II (Invitrogen, Carlsbad, Calif.) and random primers (Invitrogen) in a 20-11 reaction mixture containing 1× SuperScript buffer (Invitrogen), 1 mM dNTP mix, 10 mM dithiothreitol, and 40 units of RNase inhibitor. Total RNA and random primers were incubated at 65° C. for 5 min followed by 42° C. for 50 min. A denaturing enzyme at 70° C. for 15 min terminated the reaction. For PCR amplification, 1 µl of cDNA was added to 25 µl of a reaction mix containing 0.2 µM of each primer, 0.2 mM dNTP mix, 0.5 units of AccuPrime Taq DNA polymerase (Invitrogen), and 1× reaction buffer. PCR was performed in a RoboCycler (Stratagene, La Jolla, Calif.). Initially, we obtained standard curves for the cycle number and the absorbance optical density for each of the markers examined by RT-PCR. The cycle number (30-38) for each PCR reaction was chosen so that the absorbance of the amplified product was in the linear range. The PCR products were visualized on 2% agarose gels by ethidium bromide staining, and gels were photographed under UV lights. Band densities were quantified using the Eagle Eye II System (Stratagene). The expression of different mRNAs was normalized to 18s mRNA levels.

Protein Determination and Western Blot Analysis

Protein determination was made using the Bradford dye-binding method (Bradford (1976) *Anal Biochem* 72: 248-254). Western blotting was performed with modifications of methods described previously (Ayad and Wong (1998) *Crit. Care Med* 26: 1277-1282). Briefly, cells were lysed using an extraction buffer [10 mM Tris (hydroxymethyl) aminomethane (Tris, pH 7.5), 0.25 M sucrose, 1 mM EDTA, 5 mM benzamidine, 2 mM phenylmethylsulfonyl fluoride, and 10 µg/ml each of pepstatin A, aprotinin, and leupeptin] and centrifuged at 140 g for 10 min (4° C.). Equal amounts of the protein (25 µg) from the supernatant were dissolved in electrophoresis sample buffer and were subjected to SDS-PAGE (4-12% gradient) followed by electrophoretic transfer to a nitrocellulose membrane. Nonspecific binding of antibody was blocked by washing with Tris-buffered saline (TBS) containing 5% milk for 1 h. The blot was then subjected to two brief washes with TBS plus 0.5% Tween 20, incubated in TBS plus 0.1% Tween 20 and the specific primary antibodies (PPAR 1:2,000, Alexis Biochemicals, San Diego, Calif.; -SMA 1:50,000, Sigma; ADRP 1:3,000, a kind gift from Dr. Constantine Londos, National Institute of Diabetes and Digestive and Kidney Diseases) overnight at 4° C. Blots were then washed in TBS plus 0.1% Tween 20 and then incubated for 1 h in secondary antibody, washed, and developed with a chemiluminescent substrate (ECL; Amersham, Arlington Heights, Ill.) following the manufacturer's protocol. The densities of the specific protein bands were quantified using a scanning densitometer (Eagle Eye II still video system, Stratagene). The blots were subsequently stripped and reprobed with anti-GAPDH (1:5,000; Chemicon, Temecula, Calif.) antibody to confirm equal loading of samples.

Transfection Protocol

For transient transfection, WI38 cells were transfected by using Lipofectamine Plus Reagent (Invitrogen). Cells were trypsinized 1 day before transfection and plated on 100-mm-diameter dishes so that they were 50-80% confluent on the day of transfection. Four or 8 µg of pCMX-PPAR cDNA were diluted in 800 µl of serum-free medium, and 20 µl of Lipofectamine Plus Reagent were added to the diluted DNA. The DNA solution was incubated at room temperature for 15 min to precomplex DNA with Plus Reagent. Another 30 µl of Lipofectamine Reagent diluted to 800 µl in serum-free medium were combined with precomplexed DNA, and then the mixture incubated for 15 min at room temperature. Cells were washed with serum-free medium twice, and then 6.4 ml of serum-free medium were added to each dish, followed by the addition of DNA-Lipofectamine Plus Reagent complexes. The complexes were mixed into the medium gently and further incubated at 37° C. at 5% CO2 for 3 h. After incubation, transfection medium was replaced by complete medium containing serum and antibiotics. After incubation overnight, DNA and protein were periodically extracted and analyzed for DNA fragment test and Western blot analysis. Once transfection was confirmed, the cells were treated with nicotine ($1\times10^{-9}$ M or $1\times10^{-6}$ M) for 7 days, and the cell extracts were analyzed for PPAR and -SMA proteins by Western blot analysis.

Immunofluorescence Double Staining

Lipogenic and myogenic status of cultured WI38 cells was assessed by simultaneous staining for lipid droplets and -SMA. Lipids were stained using oil red 0 staining, and -SMA expression was assessed by using anti-SMA (cat. no. A2547, 1:1,000, mouse monoclonal IgG2, Sigma) primary antibody. In brief, cells were cultured on Lab-Tek four-chamber slides under control and experimental conditions (nicotine treatment, $1\times10^{-9}$ M for 7 days). At the end of the experimental period, slides were fixed in freshly prepared 4% paraformaldehyde. Fixed slides were washed in PBS, blocked with 3% normal goat serum (Jackson Immunoresearch Lab) in PBS for 30 min at room temperature to block nonspecific binding, and then incubated in primary antibody overnight at 4° C. Secondary biotinylated anti-mouse IgG2 was used at 1:200 dilution for 30 min. The slides were then washed 3× with PBS and with double-distilled water 2× and were then incubated with oil red 0 (Sigma) for 15-30 min. Slides were rinsed 3× for 5 min and then mounted and coverslipped with Vestashield mounting medium with 4',6'-diamidino-2-phenylindole (Vector Laboratories) visualization under a fluorescence microscope.

Statistical Analysis

Analysis of variance for multiple comparisons with Newman-Keuls post hoc test and Student's t-test, as indicated, were used to analyze the experimental data. $P<0.05$ was considered to indicate significant differences in the expression of lipogenic and myogenic markers among the control, nicotine, and nicotine plus treatment groups.

Results.

nACh Receptor Expression by WI38 Cells

Figure 1A:
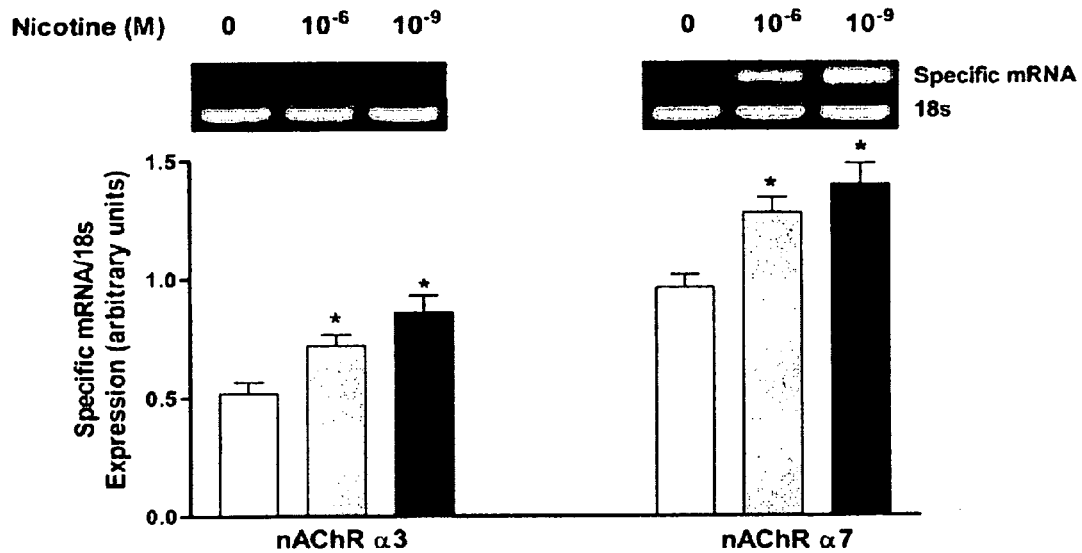
FIGS. 1A and 1B show the expression of nicotine acetylcholine (nACh) receptors 3 and 7 by control and nicotine-stimulated WI38 cells by RT-PCR (FIG. 1A) and Western blot analysis (FIG. 1B), respectively. On nicotine ($1 \times 10^{-9}$ or $1 \times 10^{-6}$ M) stimulation for 7 days, there were significant increases in the expressions of both nACh receptors $\alpha_3$ and $\alpha_7$ (*$P<0.05$ vs. control by ANOVA, n=3).
Figure 1B:
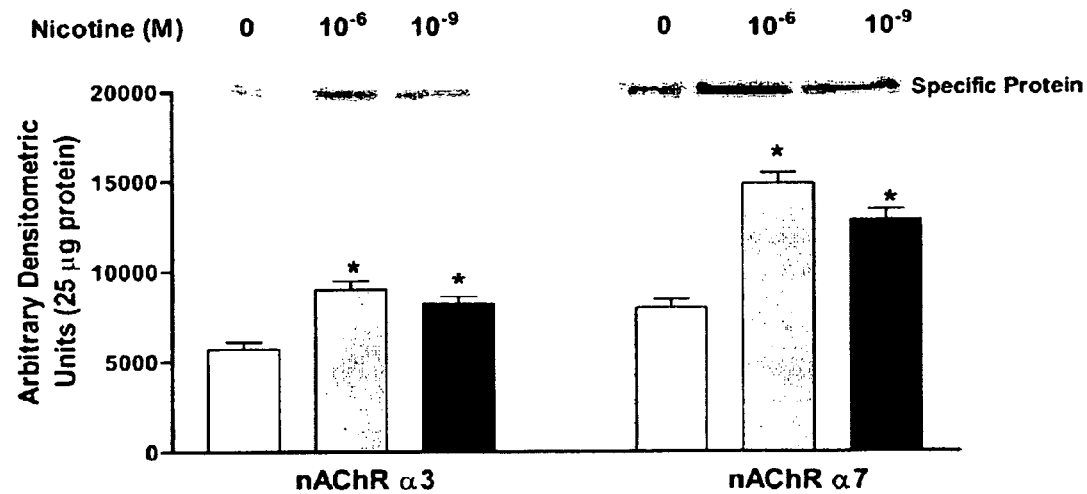

Initially, we examined the expression of nACh receptors $\alpha_3$ and $\alpha_7$ by WI38 cells. By RT-PCR (FIG. 1A) and Western blot analysis (FIG. 1B), we found that nACh receptors 3 and 7 were well expressed by WI38 cells. Upon nicotine stimulation (for 7 days), there were significant increases in the expressions of both nACh receptors $\alpha_3$ and $\alpha_7$ ($P<0.05$ vs. control).

Nicotine-Induced LIF-to-MYF Transdifferentiation

Our previous studies have demonstrated that cultured developing pulmonary alveolar interstitial LIFs, exposed to stimuli that disrupt fetal lung development, e.g., hyperoxia or volutrauma, transdifferentiate to MYFs via downregulation of PTHrP-mediated cAMP-dependent PKA signaling (Rehan and Torday (2003) *Cell Biochem Biophys* 38: 239-250; Rizzoli et al. (1983) *Endocrinology* 112: 1303-1312). In the present study, we examined whether cultured WI38 human embryonic lung fibroblasts exposed to nicotine demonstrate a similar effect. Furthermore, we determined whether stimulants of the PTHrP receptor-mediated cAMP-dependent PKA pathway would prevent nicotine-induced alveolar LIF-to-MYF transdifferentiation.

Effect of Nicotine on mRNA Expression of Markers for the Lung Fibroblast Phenotype (LIF vs. MYF).

Figure 2:
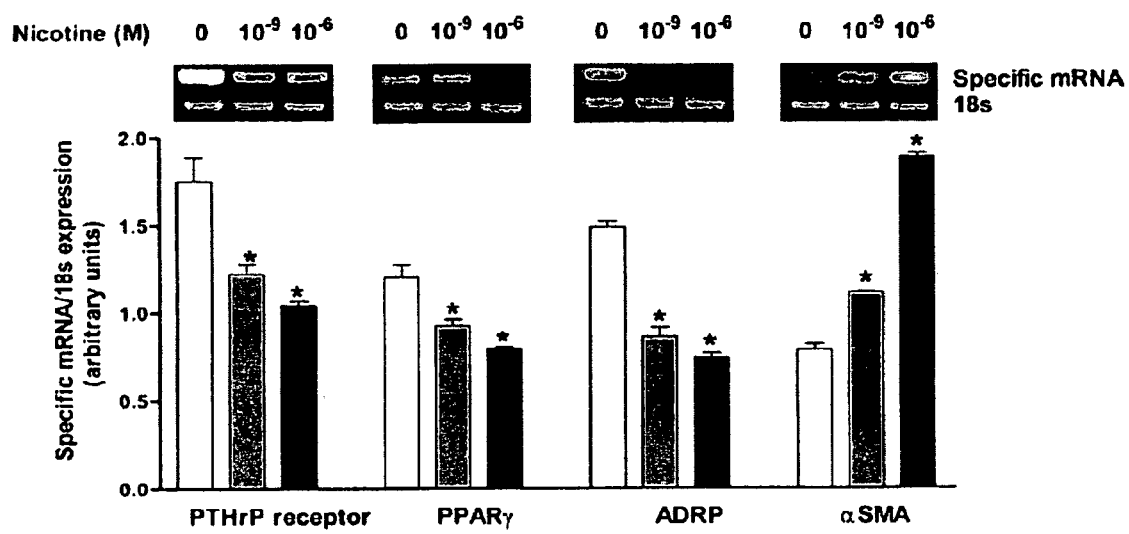
FIG. 2 shows that nicotine treatment of cultured WI38 cells for 7 days results in significant decreases in parathyroid hormone-related protein (PTHrP) receptor, peroxisome proliferator-activated receptor γ (PPARγ), and adipocyte differentiation-related protein (ADRP), and a significant increase in α-smooth muscle actin (α-SMA) mRNA expression (*$P<0.05$ vs. control by ANOVA, n=3). Representative RT-PCR blots (top) and densitometric histograms (bottom) for PTHrP receptor, PPAR, ADRP, and -SMA mRNA expression are shown.

Exposure to nicotine ($1\times10^{-9}$ or $1\times10^{6}$ M) for 7 days resulted in dose-dependent decreases in PTHrP receptor ($-33\pm8\%$ and $40\pm3\%$, respectively; means$\pm$SE), PPAR ($-26\pm7\%$ and $-37\pm3\%$), and ADRP ($-41\pm8\%$ and $-47\pm4\%$) mRNA expression, as determined by RT-PCR (*$P<0.05$ for all, nicotine vs. control; FIG. 2). This was accompanied by a concomitant dose-dependent increase in -SMA ($+38\pm4\%$ and $+140\pm5\%$) mRNA expression (*$P<0.05$, nicotine vs. control).

Effect of Nicotine on Protein Expression of Markers for Lung Fibroblast Phenotype (LIF vs. MYF).

Figure 3:
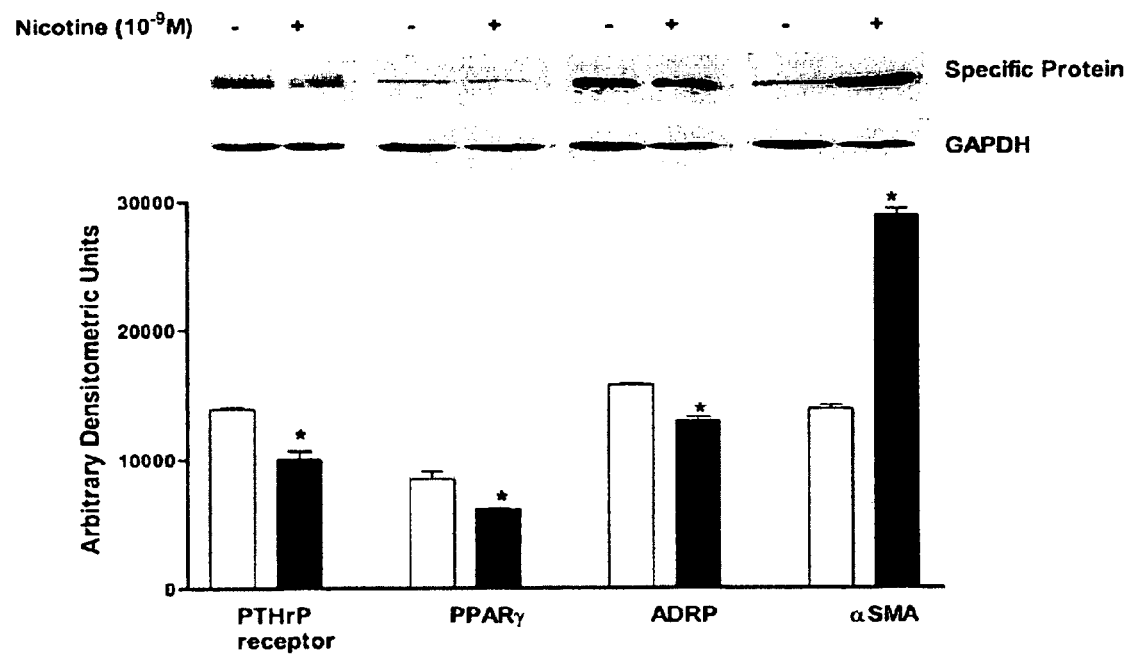
FIG. 3 shows that nicotine treatment of cultured WI38 cells for 7 days results in significant decreases in PTHrP receptor, PPAR, and ADRP, and a significant increase in -SMA protein expression (*P<0.05 vs. control by ANOVA, n=3). Representative Western blots (top) and densitometric histograms (bottom) for PTHrP receptor, PPAR, ADRP, and α-SMA mRNA expression are shown.
Figure 4:
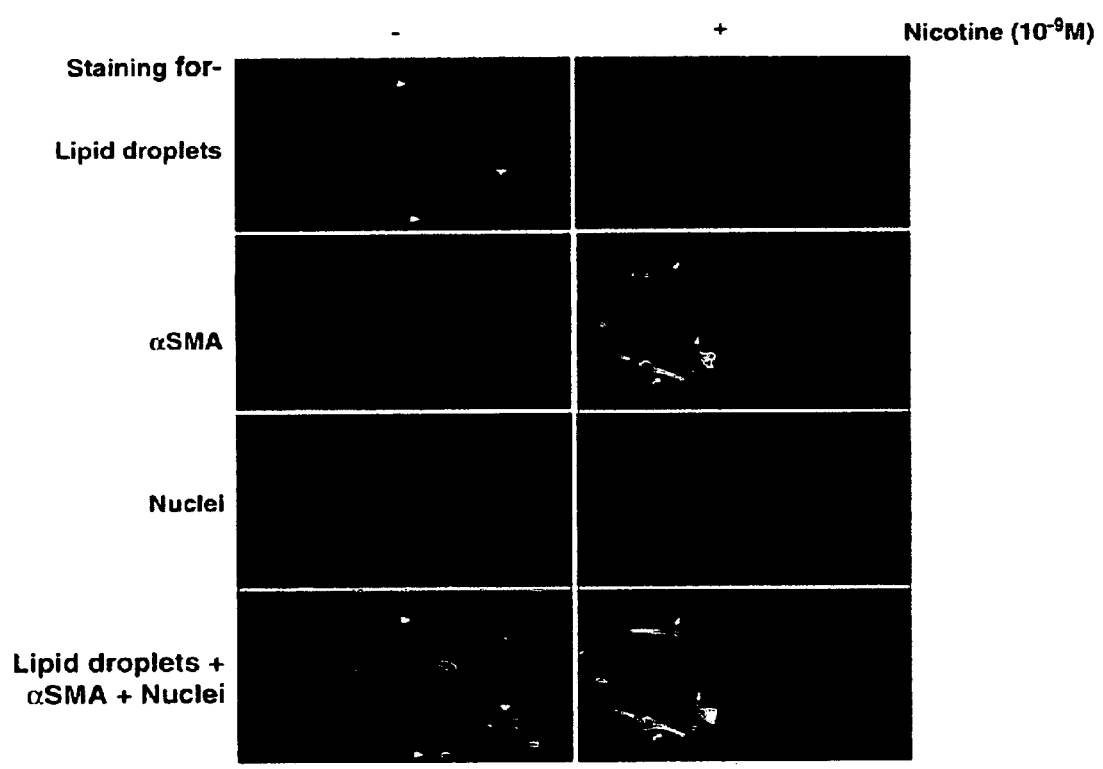
FIG. 4 shows representative immunofluorescence staining for lipid droplets (red staining) and α-SMA (green staining) in cultured WI38 cells with and without nicotine ($1\times10^{-9}$ M) treatment for 7 days is shown. Cultured WI38 cells were stained for lipid droplets alone using oil red O, α-SMA using specific monoclonal antibody, and nuclei using 4',6'-diamidino-2-phenylindole (DAPI). Bottom: shows triple staining using oil red O, α-SMA-specific antibody, and DAPI. Nicotine treatment markedly reduced staining for lipid droplets and markedly increased α-SMA expression. This can be clearly seen in the bottom panel that shows cytoplasmic colocalization of staining for lipid droplets and α-SMA.

As assessed by Western blot analysis, the protein levels of PTHrP receptor ($-31\pm7\%$), PPAR ($-24\pm2\%$), and ADRP ($-20\pm3\%$) decreased, and that of -SMA ($+100\pm5\%$) increased significantly on exposure to nicotine ($1\times10^{-9}$) for 7 days (FIG. 3), indicating nicotine-induced LIF-to-MYF transdifferentiation. This was corroborated by double-immunofluorescence staining of WI38 cells for lipid droplets and -SMA after 7 days of nicotine stimulation. Nicotine exposure clearly decreased lipid staining and increased -SMA staining, the hallmarks of LIF-to-MYF transdifferentiation (FIG. 4).

Effect of Nicotine on Triolein Uptake by WI38 Cells

To assess the effect of nicotine on LIF function, [$^3$H]triolein uptake by cultured WI38 cells under control and experimental conditions was measured. Nicotine treatment ($1\times10^{-9}$ M for 7 days) caused an almost 50% decrease in phenotypic triglyceride uptake (FIG. 5), which was effectively prevented by concomitant treatment of WI38 cells with RGZ ($1\times10^{-5}$ M), PTHrP ($5\times10^{-7}$ M), or DBcAMP ($1\times10^{-4}$ M).

Figure 5:
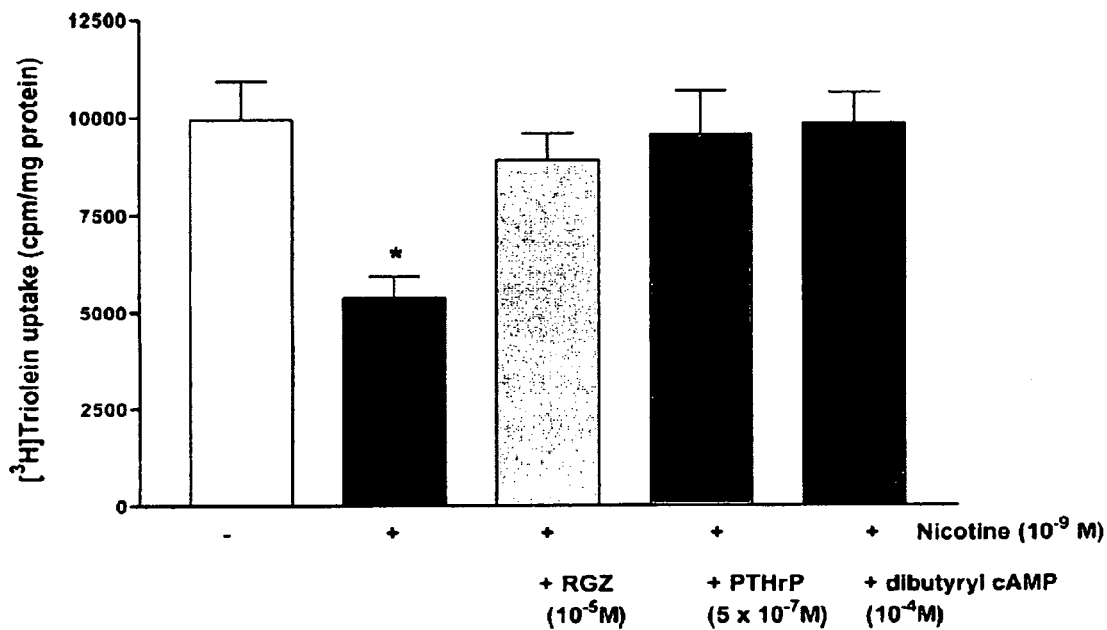
FIG. 5 shows that nicotine treatment ($1\times10^{-9}$ M for 7 days) caused an almost 50% decrease in triglyceride uptake (*P<0.05 vs. control by ANOVA, n=6), which was completely prevented by concomitant treatment of WI38 cells with rosiglitazone (RGZ; $1\times10^{-5}$ M), PTHrP ($5\times10^{-7}$ M), or dibutyryl cAMP (DBcAMP) ($1\times10^{-4}$ M).
Figure 6A:
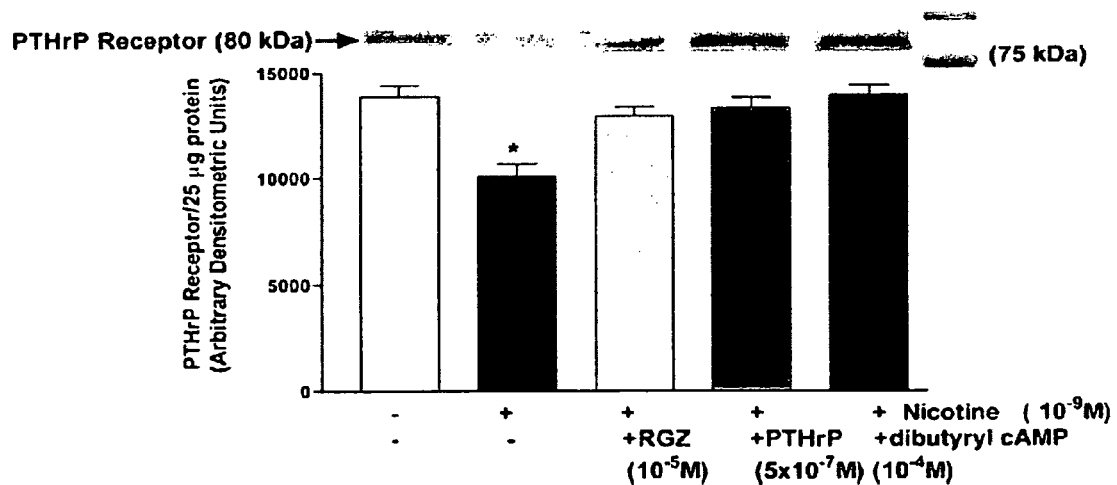
FIGS. 6A-6C show that concomitant treatment with specific stimulants of PTHrP-mediated, cAMP-dependent PKA lipogenic pathway, i.e., PTHrP ($5\times10^{-7}$ M), DBcAMP ($1\times10^{-4}$ M), or RGZ ($1\times10^{-5}$ M), completely prevents the nicotine-induced decreases in PTHrP receptor (FIG. 6A) and PPARγ (FIG. 6B) protein, and increase in α-SMA (FIG. 6C) protein expressions (*P<0.05 vs. control by ANOVA, n=3), indicating prevention of nicotine-induced lipofibroblast-to-myofibroblast transdifferentiation by these agents.
Figure 6B:
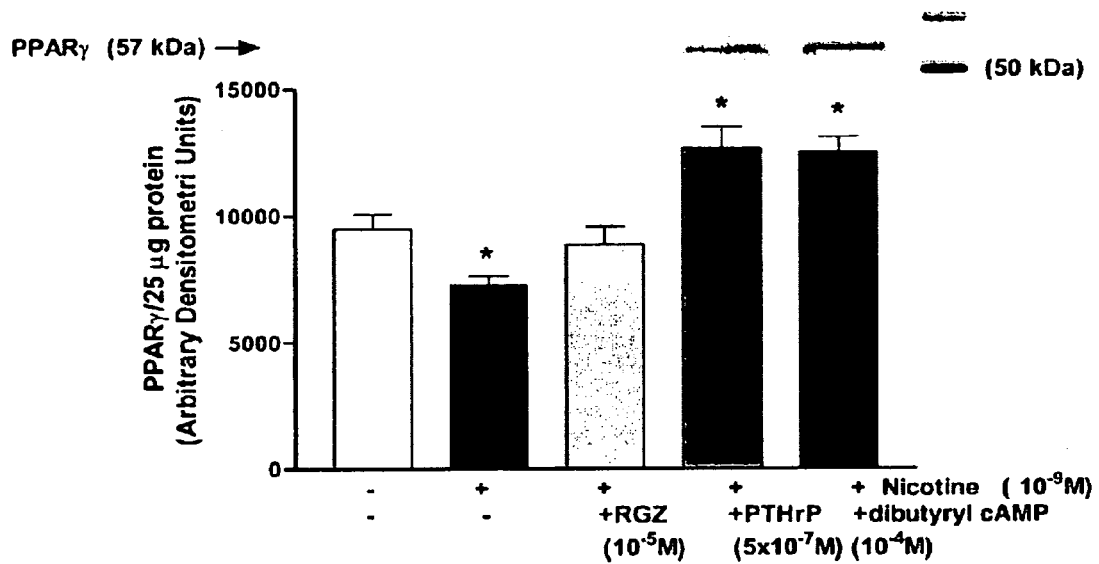
Figure 6C:
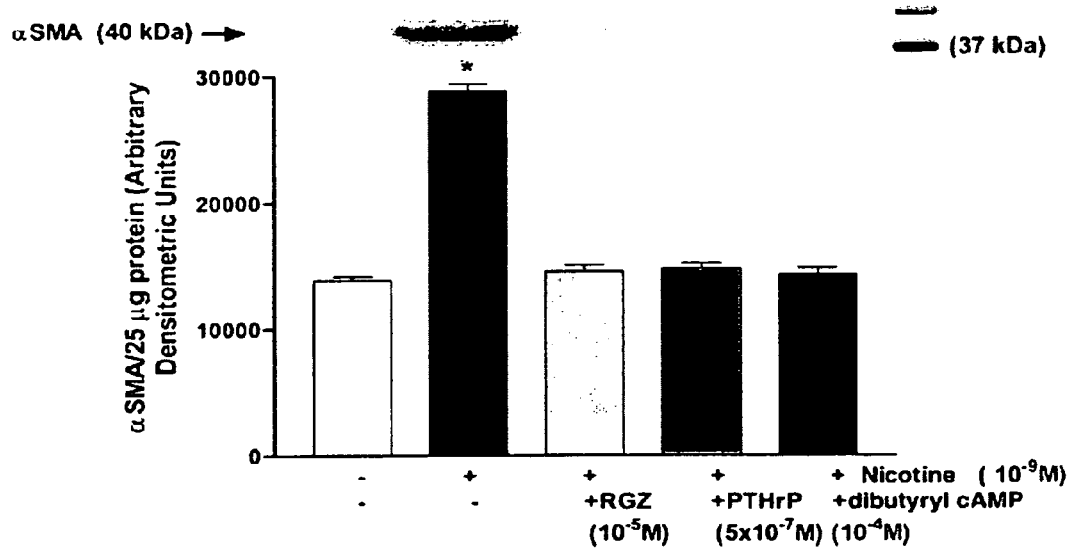
Figure 7:
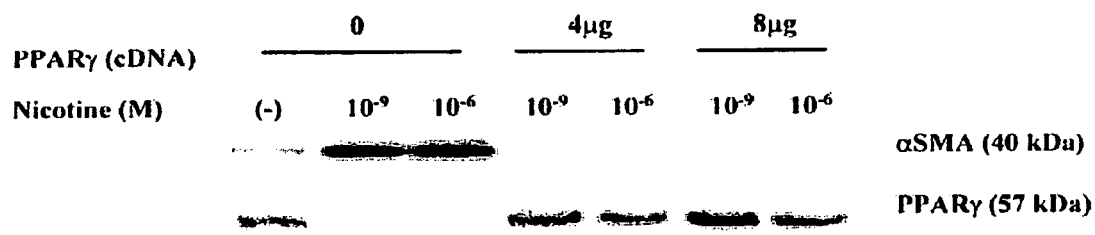
FIG. 7 shows that transfection of WI38 cells with PPAR expression vector completely prevented the nicotine-induced lipofibroblast-to-myofibroblast transdifferentiation. WI38 cells were transfected cells with either 4 or 8 µg of pCMX-PPAR cDNA. Then, the cells were treated with nicotine ($1\times10^{-9}$ or $1\times10^{-6}$ M) for 7 days, following which the expressions of PPARγ and -SMA were assessed by Western blot analyses. Under control conditions (without transfection), there was a significant decrease in PPAR and a significant increase in -SMA protein expression. However, after PPARγ transfection, these changes were completely prevented. Representative blots out of 2 independent experiments are shown.

Prevention of LIF-to-MYF Transdifferentiation by Stimulants of PTHrP-Mediated, cAMP-Dependent PKA Signaling Lipogenic Pathway The effect of specific stimulants of PTHrP-mediated, cAMP-dependent PKA lipogenic pathway on nicotine-induced LIF-to-MYF transdifferentiation was assessed by pretreating WI38 cells with PTHrP ($5\times10^{-7}$ M), DBcAMP ($1\times10^{-4}$ M), or the potent PPAR stimulant RGZ ($1\times10^{-5}$ M). Pretreatment with PTHrP, DBcAMP, or RGZ completely prevented the nicotine-induced decreases in PTHrP receptor (FIG. 6A) and PPAR (FIG. 6B) and an increase in -SMA (FIG. 6C) protein expression, indicating prevention of nicotine-induced LIF-to-MYF transdifferentiation. The prevention of nicotine-induced LIF-to-MYF transdifferentiation by stimulation of the PTHrP-driven lipogenic pathway is also supported by prevention of the nicotine-induced decrease in phenotypic triglyceride uptake by the stimulants of the PTHrP-driven PKA-mediated fibroblast lipogenic pathway (FIG. 5). As PPAR expression is central to the maintenance of fibroblast lipogenic phenotype, we next examined the effect of transfection of WI38 cells with PPAR expression vector on nicotine-induced LIF-to-MYF transdifferentiation (FIG. 7). Transfected cells were treated with nicotine ($1\times10^{-9}$ or $1\times10^{-6}$ M) for 7 days, and the expressions of PPAR and -SMA were assessed by Western blot analysis. As shown in FIG. 7, under control conditions (without transfection), there was a significant decrease in PPAR and a significant increase in -SMA protein expression. However, with PPAR transfection, these nicotine-induced changes were completely prevented.

Effect of Nicotine on PTHrP Binding to its Receptor

Figure 8:
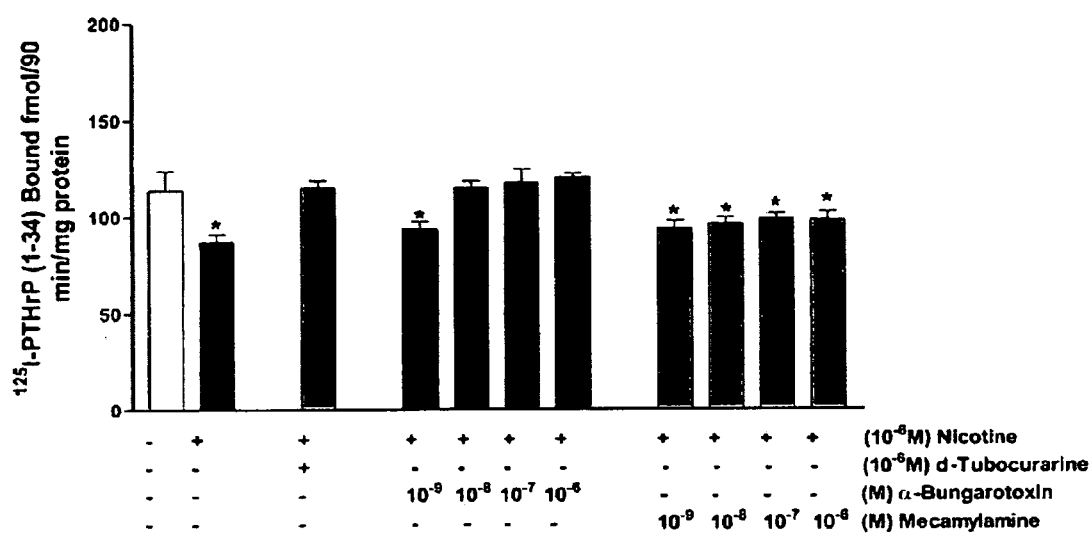
FIG. 8 shows that nicotine ($1\times10^{-6}$ M) treatment caused a 30% decrease in PTHrP binding to its receptor (fmol·90 min$^{-1}$·mg protein$^{-1}$; *P<0.05 vs. control by ANOVA, n=6), which was completely prevented by pretreatment with either D-tubocurarine ($1\times10^{-6}$ M), a nonspecific nACh receptor antagonist, or α-bungarotoxin ($1\times10^{-6}$ M), an α$_7$ nACh receptor antagonist, but not by mecamylamine ($1\times10^{-9}$ or $1\times10^{-6}$ M), an α$_3$ nACh receptor antagonist.
Figure 9:
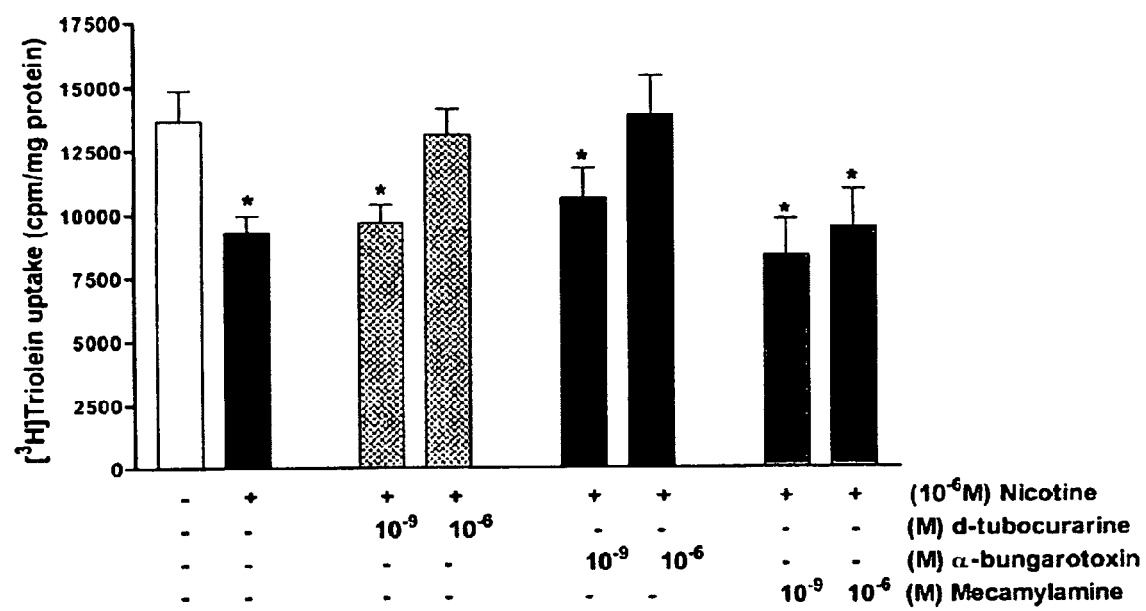
FIG. 9 shows that nicotine treatment ($1\times10^{-9}$ M for 24 h) caused an almost 30% decrease in triglyceride uptake (*P<0.05 vs. control by ANOVA, n=6), which was completely prevented by pretreatment with either D-tubocurarine ($1\times10^{-6}$ M), a nonspecific nACh receptor antagonist, or a-bungarotoxin ($1\times10^{-6}$ M), an α$_7$ nACh receptor antagonist, but not by mecamylamine ($1\times10^{-9}$ or $1\times10^{-6}$ M), an 3 nACh receptor antagonist.
Figure 10:
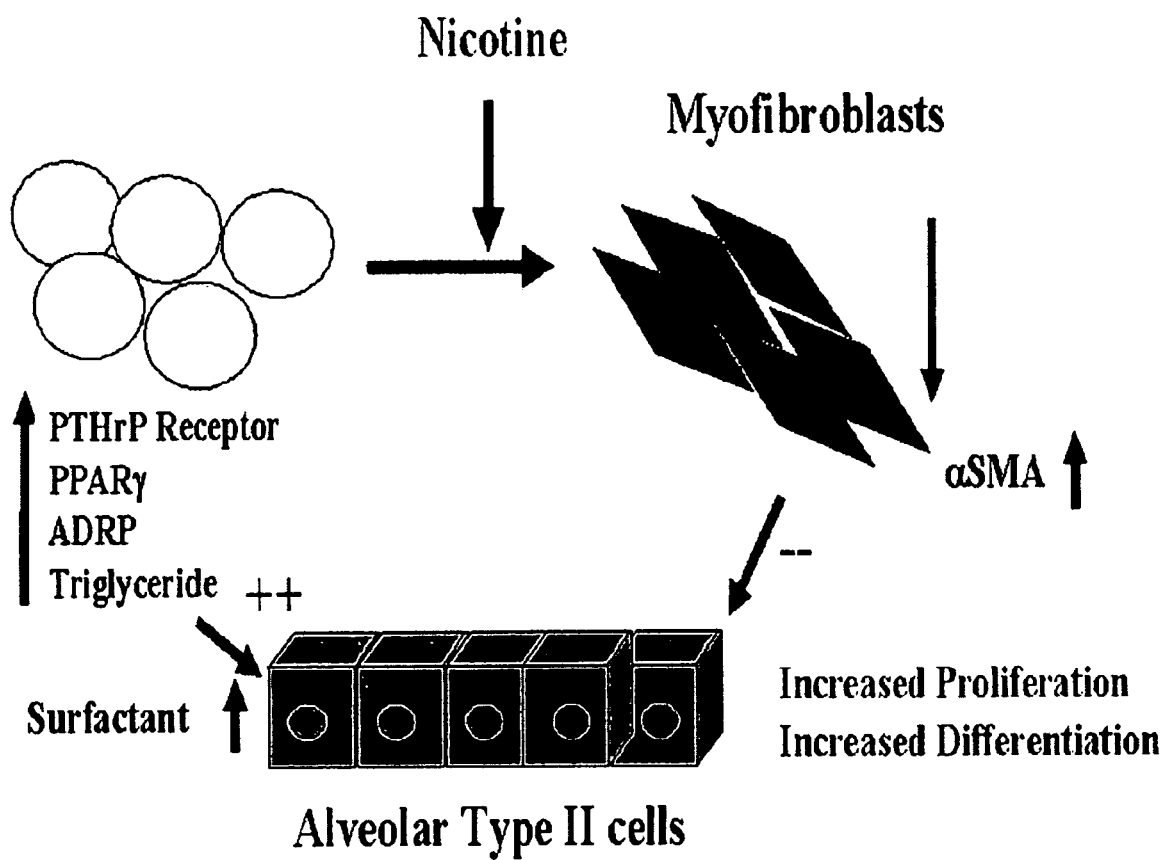
FIG. 10 schematically illustrates that nicotine adversely affects pulmonary alveolar epithelial-mesenchymal interactions, thereby inducing lipo-to-myofibroblast transdifferentiation.
Figure 11:
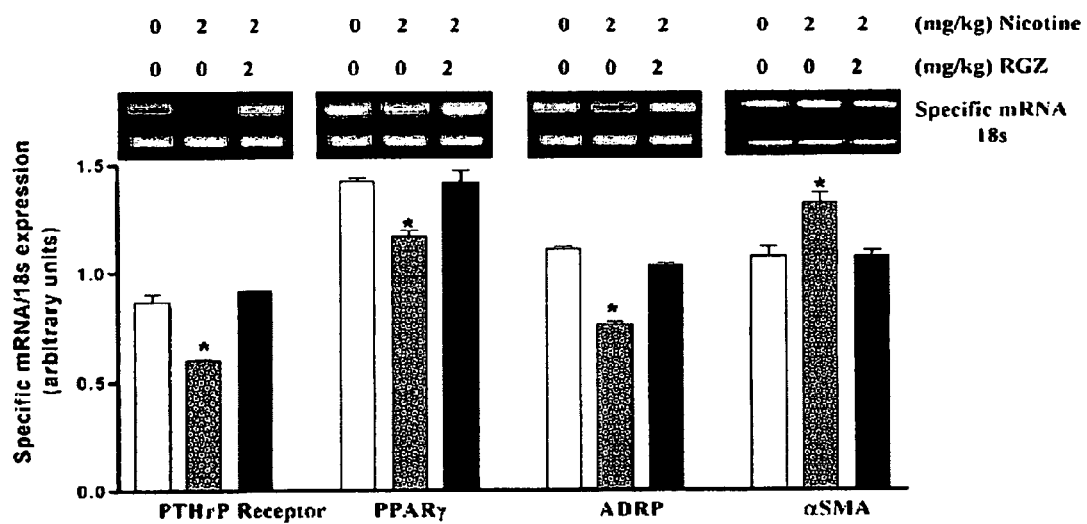
FIG. 11 shows the effect of nicotine on expression of markers for lipo-to-myofibroblast differentiation. Time-mated pregnant Sprague Dawley rat dams were treated with either placebo or nicotine (2 mg/kg) i. p. once daily from embryonic day (e) 6 of gestation until their sacrifice on e20, following which mRNA expression for the markers of lipo-to-myofibroblast transdifferentiation in the whole lung tissue was examined. There was a significant decrease in PTHrP receptor, PPARγ, and ADRP (*=p<0.05 vs controls) expression and a significant increase in αSMA mRNA expression
Figure 12:
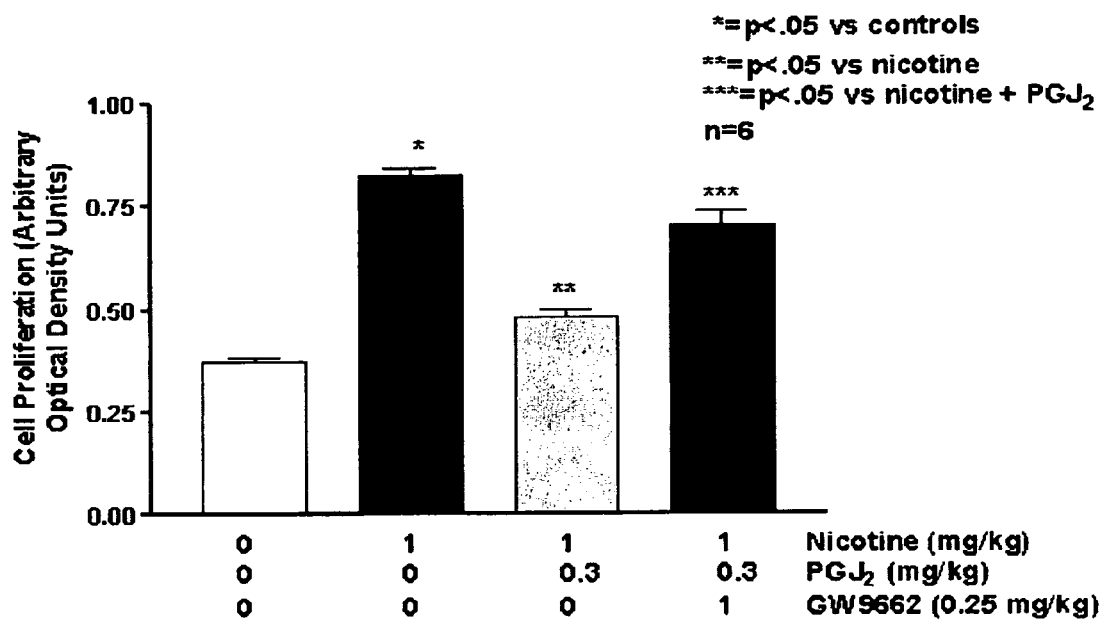
FIG. 12 shows the effect of PPARγ agonist on nicotine-induced alveolar type II cell proliferation. Following in utero nicotine administration to the dam (1 mg/kg i.p. once daily from e6 to e20 gestation), there was a 2-fold increase in alveolar type II cell proliferation vs. control group. This increase was completely blocked by the concomitant administration of a PPARγ agonist, PGJ$_2$ (p<0.05). A specific PPARγ antagonist, GW9662, largely blocked the PGJ$_2$ effect on the nicotine-induced increase in alveolar type II cell proliferation to a large extent (70%).
Figure 13:
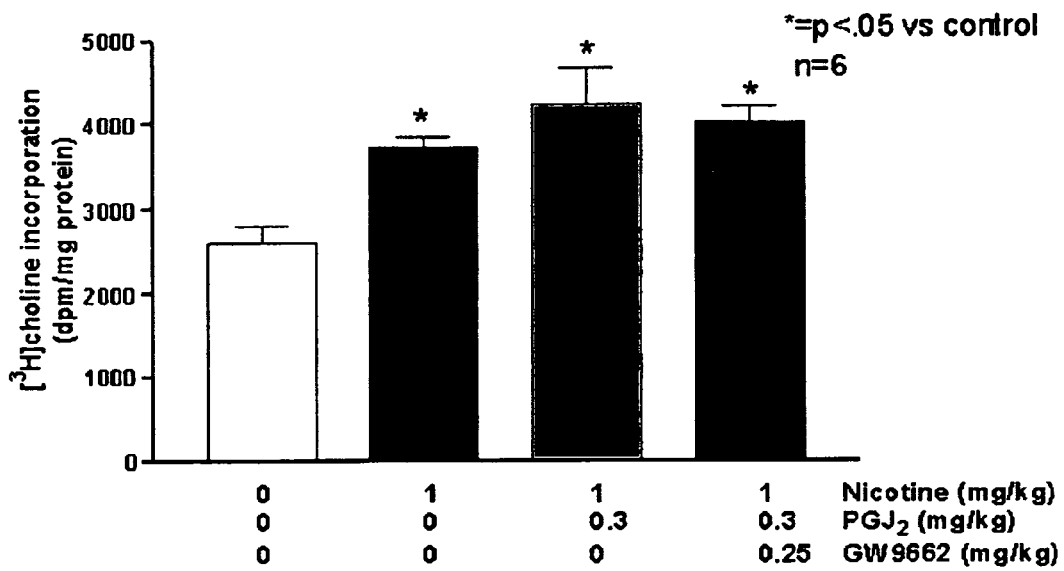
FIG. 13 shows surfactant phospholipid synthesis, as measured by [$^3$H]choline incorporation into saturated phosphatidylcholine, by cultured alveolar type II cells, following in utero nicotine (1 mg/kg administered i.p. once daily from e6 to e20 gestation to the pregnant mom) showed a significant increase in the nicotine-exposed group versus the control group (p<0.05). The concomitant treatment, with either the PPARγ agonist PGJ$_2$, or the antagonist GW9662, had no effect on the nicotine-induced increase in phospholipid synthesis under in utero conditions.
Figure 14:
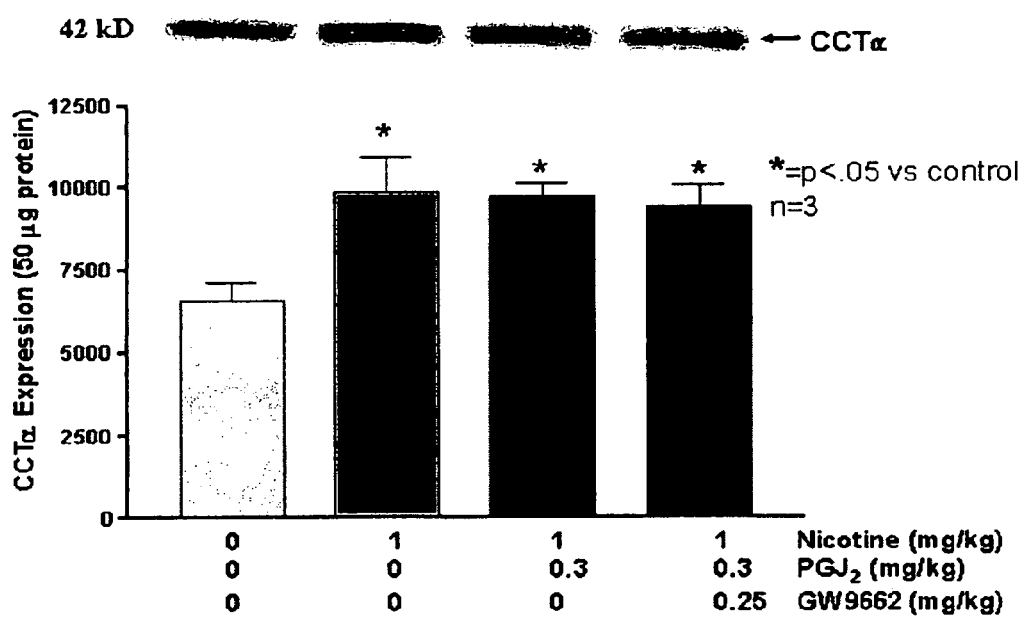
FIG. 14 shows that CTP: cholinephosphate cytidylyltransferase a (CCTα) protein expression by alveolar type II cells increased significantly following in utero (1 mg/kg administered i.p. once daily from e6 to e20 gestation to the pregnant mom) (FIG. 1A) nicotine treatment. The concomitant treatment with either PGJ$_2$ or GW9662 had no effect on the nicotine-induced increase in CCTα protein expression under in utero conditions
Figure 15:
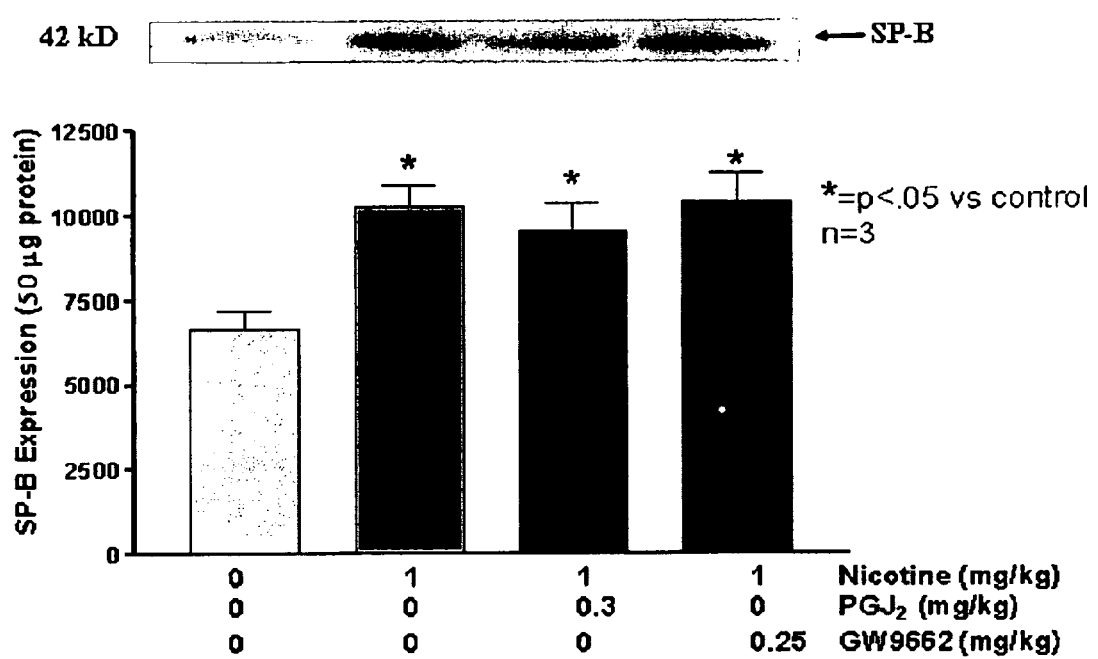
FIG. 15 shows that surfactant Protein-B expression increased significantly following both in utero (1 mg/kg administered i.p. once daily from e6 to e20 gestation to the pregnant mom) nicotine treatment. Concomitant treatment with either PGJ$_2$ or GW9662 had no effect on the nicotine-induced increase in SP-B protein expression under in utero conditions.
Figure 16A:
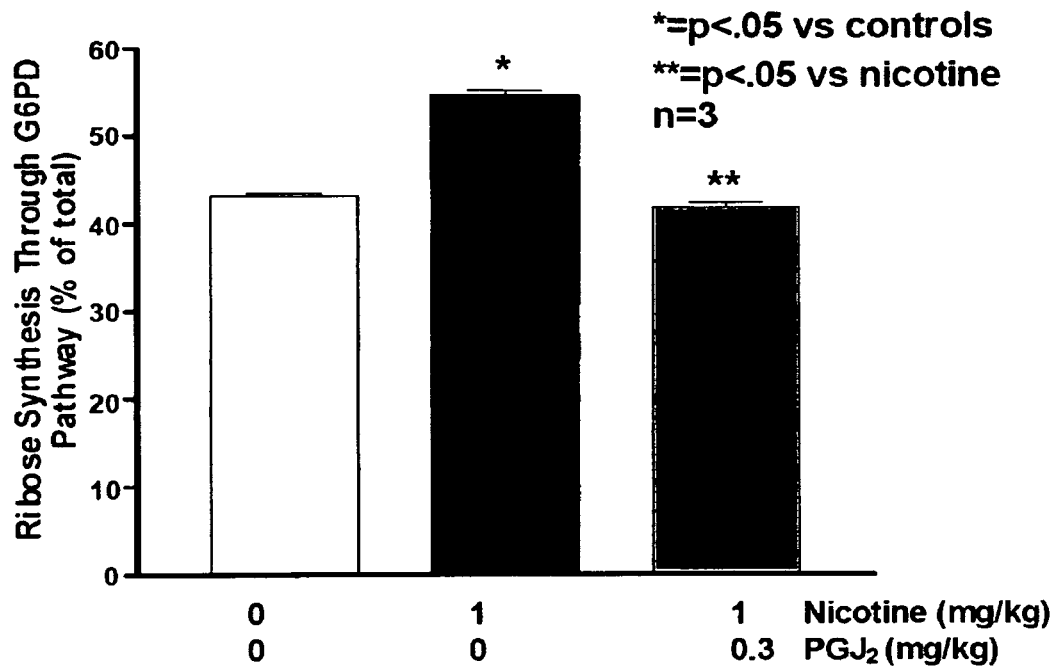
FIGS. 16A and 16B: Following in utero nicotine exposure (1 mg/kg i.p. administered once daily from e6 to e20 gestation to the pregnant mom), ribose synthesis, as measured by $^{13}$C glucose labeling, increased significantly via the oxidative glucose-6-phosphate dehydrogenase pathway, while it decreased significantly via the non-oxidative transketolase pathway (p<0.05; n=3 for both). The concomitant administration of the PPARγ agonist PGJ$_2$ completely blocked these changes
Figure 16B:
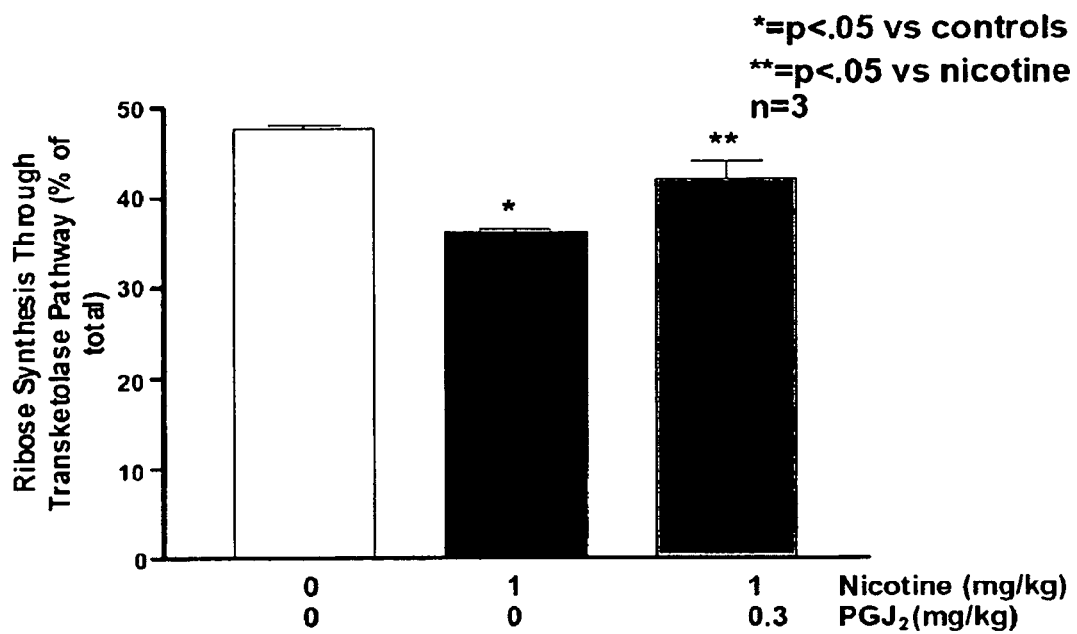
Figure 17A:
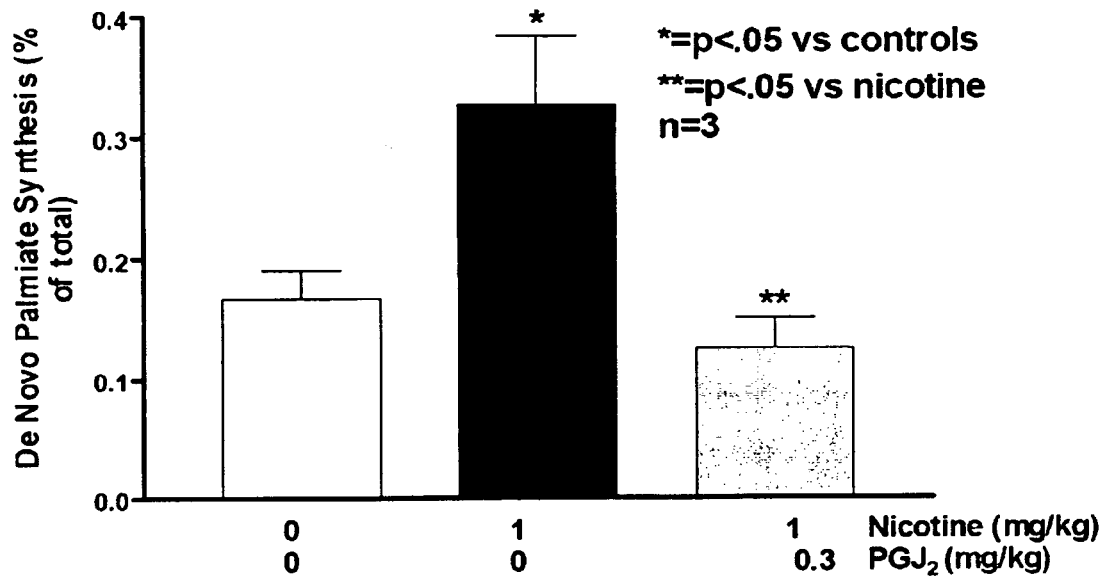
FIGS. 17A and 17B: Following in utero nicotine exposure (1 mg/kg i.p. administered once daily from e6 to e20 gestation to the pregnant mom), de novo palmitate synthesis, as a function of total palmitate in the alveolar type II cells and the $^{13}$C carbon glucose labeling of the acetyl-CoA pool, increased significantly (p<0.05 for both). The concomitant administration of the PPARγ agonist PGJ$_2$ completely blocked these changes.
Figure 17B:
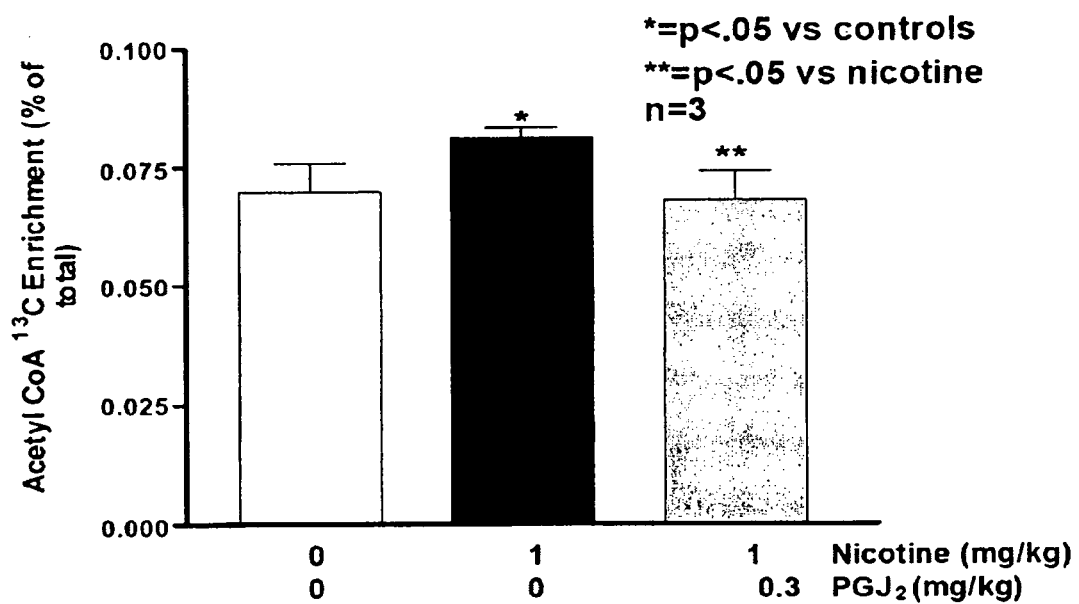

To elucidate the mechanism of nicotine-induced LIF-to-MYF transdifferentiation, the effect of nicotine on PTHrP binding to its receptor was examined. Nicotine ($1\times10^{-6}$ M) treatment caused a 30% decrease in PTHrP binding to its receptor (fmol·90 min$^{-1}$·mg protein$^{-1}$), and this effect was prevented by pretreatment with either D-tubocurarine ($1\times10^{-6}$ M), a nonspecific nicotine receptor antagonist, or $\alpha$-bungarotoxin, a specific $\alpha_7$ nACh receptor antagonist ($1\times10^{6}$ M), but not mecamylamine, an 3 nACh receptor antagonist (FIG. 8). To determine the functional significance of the differential effects of the $\alpha_7$ and $\alpha_3$ nACh receptor antagonists on PTHrP binding, the effect of nicotine ($1\times10^{-6}$ M) on triolein uptake by WI38 cells with and without D-tubocurarine ($1\times10^{-9}$ or $1\times10^{-6}$ M), -bungarotoxin ($1\times10^{-9}$ or $1\times10^{-6}$ M), or mecamylamine ($1\times10^{-9}$ or $1\times10^{-6}$ M) was examined. Similar to their differential effects on PTHrP receptor binding, the nicotine-induced decrease in triolein uptake was completely prevented by D-tubocurarine or $\alpha$-bungarotoxin, but not by mecamylamine (FIG. 9).

Discussion.

Using the WI38 human embryonic lung fibroblast cell line as a model, we tested the hypothesis that in vitro nicotine exposure disrupts the specific paracrine signaling pathway that results in pulmonary LIF-to-MYF transdifferentiation and through manipulation of specific molecular targets, this process could be prevented. First, we documented the expression of the specific nACh receptors $\alpha_3$ and $\alpha_7$ by WI38 cells, which, at least in part, have been implicated in mediating nicotine-induced effects on developing lung structure and function (Sekhon et al. (1999) *J Clin Invest* 103: 637-647; Sekhon et al. (2002) *Am J Respir Cell Mol Biol* 26: 31-41). We, for the first time, demonstrate the presence of $\alpha_3$ and $\alpha_7$ nACh receptors in the cultured lung mesenchymal cells of human embryonic origin. On nicotine stimulation, the expressions of both nACh receptors $\alpha_3$ and $\alpha_7$ increased significantly. Furthermore, the exposure of cultured WI38 cells to nicotine for 7 days resulted in significant decreases in the expression of the key fibroblast lipogenic markers PTHrP receptor and PPAR, along with their downstream targets ADRP and triglyceride uptake, and an increase in the expression of the key fibroblast myogenic marker, -SMA.

These molecular changes were accompanied by immunohistochemical changes that were also consistent with LIF-to-MYF transdifferentiation. More importantly, the nicotine-induced molecular and functional changes were completely prevented by concomitant treatment with PTHrP, cAMP, or a specific PPAR agonist, RGZ, all of which are stimulants for the fibroblast lipogenic pathway. Moreover, the nicotine effect was completely blocked in WI38 cells transfected with PPAR. Finally, the use of nonspecific (D-tubocurarine) and specific ($\alpha$-bungarotoxin and mecamylamine) antagonists of nACh receptors suggested the specific involvement of the $\alpha_7$ nACh receptor in the nicotine-induced decrease in triglyceride lipid uptake by the lung fibroblasts. To our knowledge, these data provide the first evidence of nicotine-induced pulmonary alveolar LIF-to-MYF transdifferentiation and its complete prevention by concomitant treatment with stimulants of the fibroblast lipogenic pathway. These data provide a molecular pathway for the nicotine-induced disruption of lung development and offer an opportunity to test targeted molecular strategies to prevent it.

Until now, there has been no specific intervention to prevent nicotine-induced morbidity in the developing fetus. This is mainly because of failure to eliminate maternal smoking during pregnancy coupled with a lack of understanding of the molecular mechanisms involved in nicotine-induced morbidity (Klerman et al. (2000) *Tob Control* 9, Suppl 3: III51-III55; Pierce and Nguyen (2002) *Am. J. Respir. Cell Mol. Biol.* 26: 10-13). We have recently proposed that specific disruption of pulmonary alveolar epithelial-mesenchymal interactions results in interstitial LIF-to-MYF transdifferentiation, which may be the final common pathway through which various noninflammatory and inflammatory triggers lead to chronic lung damage in the premature infant (Torday et al. (2003) *Pediatr Pathol Mol Med* 22: 189-207). Alveolar interstitial LIF-to-MYF transdifferentiation results in failed alveolarization in the developing lung, which leads to an arrest in pulmonary growth and development, the hallmarks of in utero nicotine-induced lung damage (Collins et al. (1985) *Pediatr Res* 19: 408-412; Maritz (1988) *Biol Neonate* 53: 163-170; Rubin et al. (2004) *Dev Dyn* 230: 278-289; Torday et al. (2003) *Pediatr Pathol Mol Med* 22: 189-207). Our data suggest that the likely molecular mechanisms involved include decreased PTHrP binding to its receptor with resultant down-regulation of the PTHrP-stimulated cAMP-dependent PKA pathway, which normally induces the LIF phenotype, characterized by expression of such lipogenic features as triglyceride accumulation and expression of PPAR and ADRP. Our data indicating LIF-to-MYF transdifferentiation are also supported by previous observation of lower cellular lipid content in the lung tissue of both 8- and 21-day-old rat pups following in utero nicotine exposure (Maritz (1988) *Biol Neonate* 53: 163-170).

PTHrP is a stretch-sensitive protein expressed by the developing lung epithelium and is upregulated during late fetal lung development (Rubin el al. (2004) *Dev Dyn* 230: 278-289; Rubin and Torday (2000) Totowa, N.J.: Humana, p. 269-297; Torday et al. (1998) *Am J Med Sci* 316: 205-208). It signals to the neighboring alveolar mesenchymal cells through its seven-transmembrane-spanning G protein-dependent receptor, stimulating their lipogenic phenotype (Rubin et al. (1994) *Biochim Biophys Acta* 1223: 91-100). The critical downstream target for PTHrP/PTHrP receptor signaling is PPAR, which in turn controls other lipogenic regulatory genes such as ADRP and leptin (Torday and Rehan (2002) *Am. J. Physiol. Lung Cell Mol. Physiol.* 283: L130-L135; Torday and Rehan (2003) *Cell Biochem Biophys* 37: 235-246). Therefore, stimulation of PPAR induces the lipogenic phenotype, which is necessary for maintaining alveolar homeostasis through its autocrine effect on interstitial fibroblasts and its paracrine effect on alveolar type II cells (Id.). Specifically, the interstitial LIF phenotype is of functional importance as it provides cytoprotection against oxygen free radicals (Torday et al. (2001) *Pediatr Res* 49: 843-849), traffics neutral lipid substrate to alveolar type II cells for surfactant phospholipid synthesis (Torday et al. (1995) *Biochim Biophys Acta* 1254: 198-206), and causes alveolar type II cell proliferation (Torday et al. (2003) *Pediatr Pathol Mol Med* 22: 189-207). Although MYFs also seem to be important for normal lung development, these cells are also the hallmark of chronic lung diseases in both the neonate and adult (Leslie et al. (1990) *Differentiation* 44: 143-149; Pache et al. (1998) *Mod Pathol* 11: 1064-1070; Toti et al. (1997) *Pediatr Pulmonol* 24: 22-28). In the developing lung, MYFs are fewer in number and are predominantly located at the periphery of the alveolar septa, where they very likely participate in the formation of new septa (Leslie et al. (1990) *Differentiation* 44: 143-149; Toti et al. (1997) *Pediatr Pulmonol* 24: 22-28). However, in chronic lung diseases, MYFs not only increase in number but also are located in the center of the alveolar septum in great abundance (Toti et al. (1997) *Pediatr Pulmonol* 24: 22-28). In line with these observations, using both molecular and metabolic profiling, we have previously observed that upon hyperoxic exposure, fetal rat lung LIFs transdifferentiate to MYFs (László et al. (2002) *Mol Genet Metab* 77: 230-236; Rehan and Torday (2003) *Cell Biochem Biophys* 38: 239-250). Our present data also imply LIF-to-MYF transdifferentiation as the potential underlying mechanism for the nicotine-induced lung damage in the developing fetus.

However, the effects of in utero nicotine exposure on the developing lung are extremely complex. On the one hand, there is evidence of enhanced functional pulmonary maturity at birth, possibly contributing to a decrease in the incidence of respiratory distress syndrome (Curet et al. (1983) *Am J Obstet Gynecol* 147: 446-450; Gluck and Kulovich (1973) *Am J Obstet Gynecol* 115: 539-546; Lieberman et al. (1992) *Obstet Gynecol* 79: 564-570; Wuenschell et al. (1998) *Am J Physiol Lung Cell Mol Physiol* 274: L165-L170). In contrast, clearly, reduction in both prenatal and postnatal lung growth occurs in children of women who smoke (Chen et al. (1987) *Pediatr Pulmonol* 3: 51-58; Cnattingius and Nordstrom (1996) *Acta Paediatr* 85: 1400-1402; Collins et al. (1985) *Pediatr Res* 19:

408-412; Cunningham et al. (1994) *Am J Epidemiol* 139: 1139-1152; Gilliland et al. (2003) *Am Respir Crit. Care Med* 167: 917-924; Hanrahan et al. (1992) *Am Rev Respir Dis* 145: 1129-1135; Higgins (2002) *Curr Opin Obstet Gynecol* 14: 145-151; Hofhuis et al (2003) *Arch Dis Child* 88: 10861090; Maritz (1988) *Biol Neonate* 53: 163-170; Scott (2004) *Tobacco Induced Diseases* 2: 3-25; Sekhon et al. (1999) *J Clin Invest* 103: 637-647; Sekhon et al. (2001) *Am J Respir Crit. Care Med* 164: 989-994; Walsh (1994) *Hum Biol* 66: 1059-1092). Significant suppression of lung alveolarization, functional residual capacity, and tidal flow volumes has been demonstrated in the offspring of women exposed to smoke during pregnancy. So far, the molecular mechanisms underlying these paradoxical effects remain largely unknown. Although acceleration of the lung developmental program, including surfactant phospholipid synthesis and an increase in surfactant protein expression (Curet et al. (1983) *Am J Obstet Gynecol* 147: 446-450' Gluck and Kulovich (1973) *Am J Obstet Gynecol* 115: 539-546; Lieberman et al. (1992) *Obstet Gynecol* 79: 564-570; Wuenschell et al. (1998) *Am J Physiol Lung Cell Mol Physiol* 274: L165-L170), have been observed to explain enhanced functional pulmonary maturity at birth, the mechanisms underlying suppression of lung alveolarization and its functional consequences remain far less clear. Our data provide a mechanism that explains not only failed alveolarization but also the functional pulmonary consequences following in utero nicotine exposure, including an increased predisposition to reactive airways disease. Our data complement and extend the extensive work done by Sekhon and colleagues (Sekhon et al. (1999) *J Clin Invest* 103: 637-647; Sekhon et al. (2001) *Am J Respir Crit. Care Med* 164: 989-994), who, using a rhesus monkey model, have reported that maternal nicotine exposure from day 26 to day 134 of gestation (term=165 days) alters fetal lung development, resulting in smaller lung volume and decreased alveolar surface area with an accompanying increase in the size of gas exchanging units. More importantly, concomitant with these changes, they reported a significant upregulation of the lung $\alpha_7$ nACh receptor and collagen I and III expression. In association with these changes, they also observed alterations in pulmonary function as measured by increased pulmonary resistance and decreased expiratory flows (Id.). These studies, for the first time, suggested that the observed alterations in lung mechanics in the infants of mothers who smoke during pregnancy could be linked to the passage of nicotine across the placenta, which causes increased collagen deposition and increased airway wall dimensions in the fetal lung.

We believe a shift in lung mesenchyme phenotype from a lipogenic to a myogenic type, as predicted by our findings, not only explains the increased collagen expression but also provides a molecular mechanism for the altered postnatal pulmonary mechanics observed by Sekhon and colleagues (Id.).

The complexity of the in utero effects of smoke exposure on the developing lung is further suggested by the fact that even though direct nicotine exposure might induce LIF-to-MYF transdifferentiation, in utero fetal smoke exposure is also accompanied by relative fetal hypoxia, which may prevent LIF-to-MYF transdifferentiation. As we have previously demonstrated that exposure to hyperoxia augments the spontaneously occurring pulmonary LIF-to-MYF transdifferentiation, it is tempting to speculate that the relative fetal hypoxia occurring with in utero smoke exposure may in fact have a protective effect on nicotine-induced LIF-to-MYF transdifferentiation. The exact mechanism(s) by which nicotine induces LIF-to-MYF transdifferentiation, in particular, the decrease in PTHrP receptor expression and PTHrP/PTHrP receptor binding, remains to be determined. The understanding of this mechanism is likely to be helpful designing certain specific preventive and therapeutic strategies. However, the decreases in both PTHrP/PTHrP receptor binding and its functional downstream effect, i.e., triolein uptake, were completely blocked by either tubocurarine or α-bungarotoxin, but not by mecamylamine, suggesting the specific involvement of the $\alpha_7$ nACh receptor subtype in this effect.

In summary, in addition to previously proposed mechanisms for in utero nicotine-induced lung effects, our data for the first time provide evidence for a mechanism for the direct effects of nicotine on the developing mesenchyme that could permanently alter the "developmental program" of the developing lung by disrupting critically important epithelial-mesenchymal interactions. More importantly, specific interventions that augment the pulmonary mesenchymal lipogenic pathway can at least partially ameliorate the very complex nicotine-induced in utero lung injury.

Example 2

In Utero Nicotine Exposure Alters Fetal Rat Lung Alveolar Type II cell Proliferation, Differentiation, and Metabolism We suggested that alveolar interstitial fibroblast-to-myofibroblast transdifferentiation may be a key mechanism underlying in utero nicotine-induced lung injury. However, the effects of in utero nicotine exposure on fetal alveolar type II (ATII) cells have not been fully determined. Placebo, nicotine (1 mg/kg), or nicotine (1 mg/kg)+the peroxisome proliferator-activated receptor (PPAR)-γ agonist prostaglandin $J_2$ ($PGJ_2$, 0.3 mg/kg) was administered intraperitoneally once daily to time-mated pregnant Sprague-Dawley rats from embryonic day 6 until their death on embryonic day 20. Fetal ATII cells were isolated, and ATII cell proliferation, differentiation (surfactant synthesis), and metabolism (metabolic profiling with the stable isotope $[1,2-^{13}C_2]$-D-glucose) were determined after nicotine exposure in utero or in vitro. In utero nicotine exposure significantly stimulated ATII cell proliferation, differentiation, and metabolism. Although the effects on ATII cell proliferation and metabolism were almost completely prevented by concomitant treatment with $PGJ_2$, the effects on surfactant synthesis were not. On the basis of in utero and in vitro data, we conclude that surfactant synthesis is stimulated by nicotine's direct effect on ATII cells, whereas cell proliferation and metabolism are affected via a paracrine mechanism(s) secondary to its effects on the adepithelial fibroblasts. These data provide evidence for direct and indirect effects of in utero nicotine exposure on fetal ATII cells that could permanently alter the "developmental program" of the developing lung. More importantly, concomitant administration of PPAR-γ agonists can effectively attenuate many of the effects of in utero exposure to nicotine on ATII cells.

There is compelling evidence to suggest that although maternal smoking during pregnancy causes accelerated alveolar type II (ATII) cell differentiation at birth, there are significant longterm deleterious effects on pulmonary outcome (Collins et al. 91985) *Pediatr. Res.* 19: 408-412; Cunningham et al. 91994) *Am. J. Epidemiol.* 139: 1139-1152, 1994; Curet et al. (1983) *Am. J. Obstet. Gynecol.* 147: 446-450; Gluck and Kulovich (1973) *Am. J. Obstet. Gynecol.* 115: 539-546; Hanrahan et al. (1992) *Am. Rev. Respir. Dis.* 145: 1129-1135; Lieberman et al. (1992) *Obstet. Gynecol.* 79: 564570; Wuenschell et al. (1998) *Am. J. Physiol Lung Cell Mol Physiol* 274: L165-L170). However, the mechanism(s) underlying these paradoxical pulmonary effects remain(s)

largely unknown (Pierce and Nguyen (2002) *Am. J. Respir. Cell Mol. Biol.* 26: 1013; Proskocil et al. (2005) *Am. J. Respir. Crit. Care Med.* 171: 1032-1039; Sekhonet al. (2992) *Am. J. Respir. Cell Mol. Biol.* 26: 31-41). ATII cell growth and differentiation and, hence, alveolar integrity are regulated by a number of autocrine, paracrine, and endocrine factors. In particular, mesenchymal-epithelial interactions are critically important for normal lung development and injury/repair (Shannon and Hyatt (2004) *Annu. Rev. Physiol.* 66: 625645; Smith and Post (1989) *Am. J. Physiol. Lung Cell Mol. Physiol.* 257: L174-L178; Torday et al. (2003) *Pediatr. Pathol. Mol. Med.,* 22: 189-207; Torday et al. (2002) *Am. J. Physiol. Lung Cell Mol. Physiol.* 282: L405-L410 [Corrigenda. *Am. J. Physiol Lung Cell Mol Physiol* 282: April 2002, following table of contents.]). We recently implicated the disruption of a specific epithelial-mesenchymal signaling pathway that specifically down-regulates peroxisome proliferatoractivated receptor (PPAR)-γ expression by alveolar interstitial fibroblasts (AIFs), resulting in AIF-to-myofibroblast (MYF) transdifferentiation in utero nicotine exposure-induced lung injury (Rehan et al. (2005) *Am. J. Physiol. Lung Cell Mol. Physiol.* 289: L667-L676). It was demonstrated that augmentation of PPAR-γ in AIFs can prevent nicotine-induced AIF-to-MYF transdifferentiation. We have suggested that this AIF-to-MYF transdifferentiation might be a key mechanism underlying the alterations in lung development following in utero nicotine exposure, explaining its long-term detrimental effects on pulmonary outcome (Id). However, the effects of in utero nicotine exposure on the pulmonary ATII cell, which secretes surfactant and is important to the maintenance of alveolar homeostasis, remain to be fully elucidated. We tested the hypothesis that in utero nicotine exposure significantly affects ATII cell proliferation and differentiation and that augmentation of PPAR-γ expression would reduce or prevent the nicotine-mediated alterations in ATII cell proliferation and differentiation. Here, we describe the effects of in utero nicotine exposure on ATII cell proliferation, differentiation, and metabolism. Our data, for the first time, help explain the mechanisms underlying the paradoxical short-term acceleration in pulmonary differentiation but a poor long-term pulmonary outcome in infants born to mothers who smoke during pregnancy. These data provide a rationale and a molecular intervention strategy that is believed to attenuate the in utero nicotine exposure-associated effects on pulmonary outcomes.

Materials and Methods

Animals

Pathogen-free timed (embryonic day 0=day of mating) pregnant Sprague-Dawley rats (200-250 g body wt) were obtained from Charles River (Hollister, Calif.) at embryonic day 3 and allowed to acclimatize until embryonic day 6. Dams were randomized into control (placebo), nicotine, and nicotine+PPAR-γ agonist groups. Dams received placebo (diluent, normal saline), nicotine tartrate (1 mg/kg) alone, or nicotine tartrate (1 mg/kg)+the PPAR-γ agonist prostaglandin $J_2$ ($PGJ_2$, 0.3 mg/kg) intraperitoneally in 100-µl volumes once daily from embryonic day 6 until they were killed with an overdose of pentobarbital sodium (200 mg/kg) on embryonic day 20. The fetuses were extracted by cesarean section, and the lungs were snap frozen for later analysis or processed for ATII cell or fibroblast culture. To determine whether nicotine-induced effects on fetal lung development specifically involved PPAR-γ-mediated mesenchymalepithelial paracrine pathways, some animals in the nicotine+$PGJ_2$ group were pretreated with a specific PPAR-γ antagonist, GW-9662 (Sigma, St. Louis, Mo.; 0.25 mg/kg). All studies were approved by the Los Angeles Biomedical Research Institute Institutional Review Board and were conducted in accordance with the National Institutes of Health *Guide for the Care and Use of Laboratory Animals.*

The dose (1 mg/kg) chosen for the nicotine treatment in this study has previously been shown in a number of studies to result in a specific lung phenotype characterized by changes in ATII cell proliferation and differentiation (Maritz and Thomas (1995) *Cell. Biol. Int.* 19: 323-331). This dose of nicotine (0.161.8 mg kg body wt$^{-1}$ day$^{-1}$) is comparable to the dose to which habitual smokers are exposed (Id.). Food and water were provided to the dams ad libitum, and a 12:12-h light-dark cycle was maintained. Three animals were used for each condition per experiment, and each experiment was repeated at least three times.

Isolation of Fetal Rat Lung ATII Cells

ATII cells were isolated using differential adherence in monolayer culture, as described previously (Battenburg et al. (1990) *Biochim. Biophys. Acta* 960: 441-456). Briefly, three to five darns were used per preparation. The fetuses were delivered via cesarean section, and fetal lungs were placed in Hanks' balanced salt solution without calcium and magnesium. The lungs were chopped into small pieces with sterile scissors, the Hanks' balanced salt solution was decanted, and 5 vol of 0.05% trypsin were added. A Teflon stirring bar was used to further dissociate the lungs by mechanical disruption of the tissue during incubation in a 37° C. water bath. After the tissue was dispersed into a unicellular suspension, the cells were pelleted at 500 g for 10 min at room temperature in a 50-ml polystyrene centrifuge tube. The supernatant was decanted, and the pellet was resuspended in DMEM containing 20% FBS to yield a mixed-cell suspension of ~3×10$^8$ cells, as determined by Coulter particle counter (Beckman-Coulter, Hialeah, Fla.). The cell suspension was then added to 75-cm$^2$ (T-75) culture flasks for 30-60 min to allow for differential adherence of lung fibroblasts. The unattached cells were then transferred to another T-75 culture flask for an additional 60 min. After this second culture period, the medium and nonadherent cells were removed from the flask and diluted with 1 vol of culture medium. This diluted suspension was cultured overnight in a T-75 culture flask at 37° C. in a $CO_2$ incubator to allow the ATII cells to adhere. The ATII cells were identified by their appearance in culture under phase contrast microscopy, lamellar body content, cytokeratin staining, and microvillar processes. All cell cultures contained >95% ATII cells.

Cell Culture

Isolated ATII cells were cultured in DMEM+10% FBS in 6- and 96-well plates, 100-mm dishes, and T-75 flasks, as needed, and maintained at 37° C. in a humidified incubator containing 5% $CO_2$-95% air. At 80-90% confluence, cells were processed for cell proliferation, differentiation, and metabolic studies (see below).

Lung Explant Culture

Explants derived from three to five litters of rats were used for each experiment during the course of the studies. Lungs were harvested from fetal rats under sterile conditions. The lung tissue was chopped into ~1-mm cubes and incubated in 0.5 ml of Waymouth's MB-252/1 medium containing penicillin (100 U/ml)-streptomycin (100 U/ml) and Fungizone (2.5 µg/ml) in six-well plates while rocking on an oscillating platform (3 cycles/min) in 5% $CO_2$-95% air at 37° C. The explants were allowed to attach for 1-2 h.

Cell Proliferation

In Vivo ATII Cell Proliferation Assay.

The EnVision double-stain system (DakoCytomation, Carpentaria, Calif.) was used for immunohistochemical determination of in vivo ATII cell proliferation by double labeling with a cell proliferation-specific marker, proliferating cell nuclear antigen (PCNA), and an ATII cell-specific marker, surfactant protein (SP)C(SP-C). Briefly, dams were killed by cesarean section, and fetal lung tissue was fixed in 4% paraformaldehyde for 4 h. After fixation, the tissue was suspended in 30% sucrose overnight, washed in PBS, and then embedded in tissue-embedding medium (OCT Tissue-Tek, Sakura). Sections (8 μm) were cut using a cryotome (Leica). Endogenous peroxidase was blocked, and the sections were processed with 10 mM citrate buffer (pH 6.0) in a microwave oven for 5 min at high power. Subsequently, sections were incubated with the first primary antibody, mouse monoclonal proliferating cell nuclear antigen (PCNA) antibody (1:1,000 dilution; Santa Cruz Biotechnology, Santa Cruz, Calif.) for 30 min at room temperature; then the secondary antibody conjugated to horseradish peroxidase was added to the sections for another 30 min at room temperature. Vector SG (Vector Laboratories, Burlingame, Calif.) was used as a chromogen, and blue-gray nuclear staining was considered positive. After the slides were washed, they were incubated with double-stain block, and the second primary rabbit polyclonal antibody SP-C (1:200 dilution; Chemicon, Temecula, Calif.) was applied to the sections at room temperature for 30 min and then the secondary antibody labeled with alkaline phosphatase was applied for another 30 min. The immunoreaction was visualized with Vector Red (Vector Laboratories), and red cytoplasmic staining was considered positive. After dehydration, the slides were mounted with permanent mounting medium (VectaMount, Vector Laboratories). As negative controls, sections were incubated with normal serum in the absence of primary antibody. The slides were examined at ×40 magnification, and ATII cells in 10 randomly selected areas (grid size 40,000 μm$^2$) per slide (2 slides/animal) were counted for the purposes of statistical analysis.

Ex Vivo ATII Cell Proliferation Assay.

After in utero nicotine treatment, ATII cells were isolated as described above, and 5,000 cells were plated per well in 96-well plates. According to the manufacturer's protocol, cell proliferation was determined by the tetrazolium dye assay, which is based on the conversion of a tetrazolium salt to a red formazan product by living cells (Cell Proliferation Assay, Promega).

In Vitro Cell Proliferation Assay.

Cultured ATII cells or explants were treated with nicotine under various experimental conditions (see below), and cell proliferation was determined by Cell Proliferation Assay (Promega) or dual PCNA and SP-C labeling, respectively (see above).

Measurement of Phospholipid Synthesis

Incorporation of [methyl-3H]choline chloride (NEN Dupont) into saturated phosphatidylcholine was determined in monolayers of cultured explants and ATII cells. Briefly, subconfluent monolayer cultures of ATII cells in DMEM+ 0.1% FBS that had been treated with nicotine or freshly isolated lung explant cultures in Waymouth's medium in six-well plates were incubated with [methyl-3H]choline chloride (1 μCi/ml) for 4 h. After incubation, explants and cells were washed three times with ice-cold PBS. The explants and the scraped cells were thoroughly homogenized, and the cellular lipids were extracted with chloroform-methanol (2:1) (Bligh and Dyer (1959) *Can. J. Biochem. Physiol.*, 37: 911-917). The organic phase was dried under a stream of nitrogen at 60° C., resuspended in 0.5 ml of carbon tetrachloride containing 3.5 mg of osmium tetroxide, and left at room temperature for 15 min. The reaction mixture was redried under nitrogen and resuspended in 70 μl of chloroform-methanol (9:1, vol/vol). The lipid extracts were transferred to silica gel plates (Kodak, Rochester, N.Y.) and developed in a chloroform-methanol:water (65:25:4) solvent system. Pure dipalmitoyl phosphatidylcholine was used as the chromatographic standard. The developed plates were stained with bromothymol blue, blotted, and vacuum dried for 5 min at 90° C. Chromatogram spots corresponding to the migration of saturated phosphatidylcholine were scraped from the plates and counted by liquid scintillation spectrometry. The amounts of [methyl$^3$H]choline chloride incorporated into saturated phosphatidylcholine were expressed as disintegrations per minute per milligram of protein.

Western Analysis

Protein extraction and Western blot analysis for SP-B and choline phosphate cytidylyltransferase-α (CCT-α) were performed using standard methods. Briefly, cells were homogenized in 10 mM Tris (pH 7.5), 0.25 M sucrose, 1 mM EDTA, 5 mM benzamidine, 2 mM phenylmethylsulfonyl fluoride, and 10 μg/ml each of pepstatin A, aprotinin, and leupeptin and centrifuged at 14,000 rpm for 10 min at 4° C. Equal amounts of the protein from the supernatant were dissolved in electrophoresis sample buffer and subjected to SDS-polyacrylamide (4-12% gradient) gel electrophoresis followed by electrophoretic transfer to a nitrocellulose membrane. The membrane was blocked with 5% milk in 1× Tris-buffered saline containing 0.1% Tween 20 for 1 h and then incubated with rabbit anti-human SP-B polyclonal antibody (1:1,000 dilution; Chemicon) overnight at 4° C. The antibody for CCT-α (1:2,000 dilution) was a kind gift from Dr. Mallampalli (University of Iowa, Iowa City, Iowa). Subsequently, the membrane was washed with 1× Tris-buffered saline+0.1% Tween 20 and incubated with a 1:3,000 dilution of anti-rabbit horseradish peroxidase-linked whole antibody immunoglobulin G (Amersham, Arlington Heights, Ill.) for 1 h at room temperature, washed again, and developed with a chemiluminescent substrate (ECL, Amersham) following the manufacturer's protocol. The density of the SP-B and CCT-α bands was quantified using a scanning densitometer (Eagle Eye, Stratagene).

Stable Isotope Labeling of Intracellular Glucose Metabolites

Stable isotope labeling of intracellular glucose metabolites was performed according to previously described methods (Lâszló et al. (2002) *Mol. Genet. Metab.* 77: 230-236). Briefly, [1,2-$^{13}$C$_2$]glucose was purchased with >99% enrichment for the specified carbon positions from Isotech (Miamisburg, Ohio). Lung ATII cells were isolated from embryonic day 20 pups from specified treatment groups and cultured in T-75 tissue culture flasks. At near confluence, cells were incubated in the presence of DMEM containing 180 mg/dl [1,2-$^{13}$C$_2$]glucose (50% isotope-enriched glucose) for 72 h to determine the changes in carbon flux under various treatment conditions. The [$^{13}$C]glucose label is readily incorporated into various metabolites in mammalian cells, including ribonucleic acid (through ribose synthesis), lactate (through glycolysis), glutamate (through the tricarboxylic acid cycle), and palmitate (through the formation of acetyl-CoA). As the molecular weight (atomic mass unit) of these molecules increases on incorporation of the heavier $^{13}$C atoms derived from [1,2,$^{13}$C$_2$]glucose, they can be separated and quantitatively analyzed by gas chromatography-mass spectrometry (MS) on the basis of changes in their mass-to-charge ratios (m/z). This method allows simultaneous estimation of the relative synthetic rates of macromolecules in response to various treatments using a common precursor.

Recovery of Glucose Metabolites From Lung ATII Cells

Media glucose and lactate levels were directly measured using a Cobas Mira chemical analyzer (Roche Diagnostics).

Glucose oxidation by fibroblasts was determined on the basis of the media 13C- to 12C ratios in released $CO_2$ by a Finnegan Delta-S isotope ratio mass spectroscope. The rate of $^{13}CO_2$ release was measured to estimate the rate of glucose carbon oxidation by the cells, expressed as the atom percent excess, which is the proportion of $^{13}C$ produced by the cultured cells above background in calibration standard samples.

RNA ribose was isolated by acid hydrolysis (2 N HCl for 2 h) of cellular RNA after TRIzol extraction of cell pellets. Hydroxylamine in pyridine and acetic anhydride was used to derivatize ribose isolated from RNA to its aldonitrile acetate form. We monitored the ion clusters around m/z 256 (carbons 1-5 of ribose, chemical ionization), m/z 217 (carbons 3-5 of ribose), and m/z 242 (carbons 1-4 of ribose, electron impact ionization) to detect the molar enrichment for, and the positional distribution of, the $^{13}C$ label in ribose.

Lactate in the cell culture medium (0.2 ml) was extracted with ethyl acetate after acidification with HCl. Lactate was derivatized to its propylamine-heptafluorobutyric anhydrate form, and the m/z 328 ion cluster (carbons 1-3 of lactate, chemical ionization) was monitored for the detection of M1 (recycled lactate through the pentose cycle) and M2 (lactate produced by the Embden-Meyerhof-Parnas pathway) to estimate pentose cycle activity.

Fatty acids in the cell culture medium were extracted by saponification of the TRIzol cell extract after removal of the RNA-containing supernatant. Cell debris was treated with 30% KOH and 100% ethanol overnight, and petroleum ether was used to extract lipid. Methanolic HCl (0.5 N) was used to convert fatty acids to their methylated derivatives. Palmitate was monitored at ion cluster m/z 270. The enrichment of acetyl units and the de novo synthesis of the lipid fraction were determined using mass isotopomer distribution analysis for different isotopomers of palmitate.

Gas Chromatograthy-MS

Mass spectral data were obtained on an HP5973 mass-selective detector connected to an HP6890 gas chromatograph (GC). The settings were as follows: GC inlet 230° C., transfer line 280° C., MS source 230° C., MS Quad 150° C. An HP-5 capillary column (30 m long, 250 μm diameter, 0.25 μm film thickness) was used for glucose, ribose, and lactate analyses. A Bpx70 column (25 m long, 220 μm diameter, 0.25 μm film thickness; SGE, Austin, Tex.) was used for fatty acid analysis, with specific temperature programming for each compound studied.

Data Analysis and Statistical Methods

In vitro experiments were carried out using three cultures for each treatment regimen, and the experiments were repeated one to three times. Mass spectral analyses were carried out by three independent, automated injections of a 1-μl sample and accepted only if the sample standard deviation was <1% of the normalized peak intensity. Statistical analyses were performed using ANOVA. P<0.05 was considered to indicate statistically significant differences among different treatment conditions.

Results

Effect of Nicotine on ATII Cell Proliferation

In Vivo Assessment.

Figure 18:
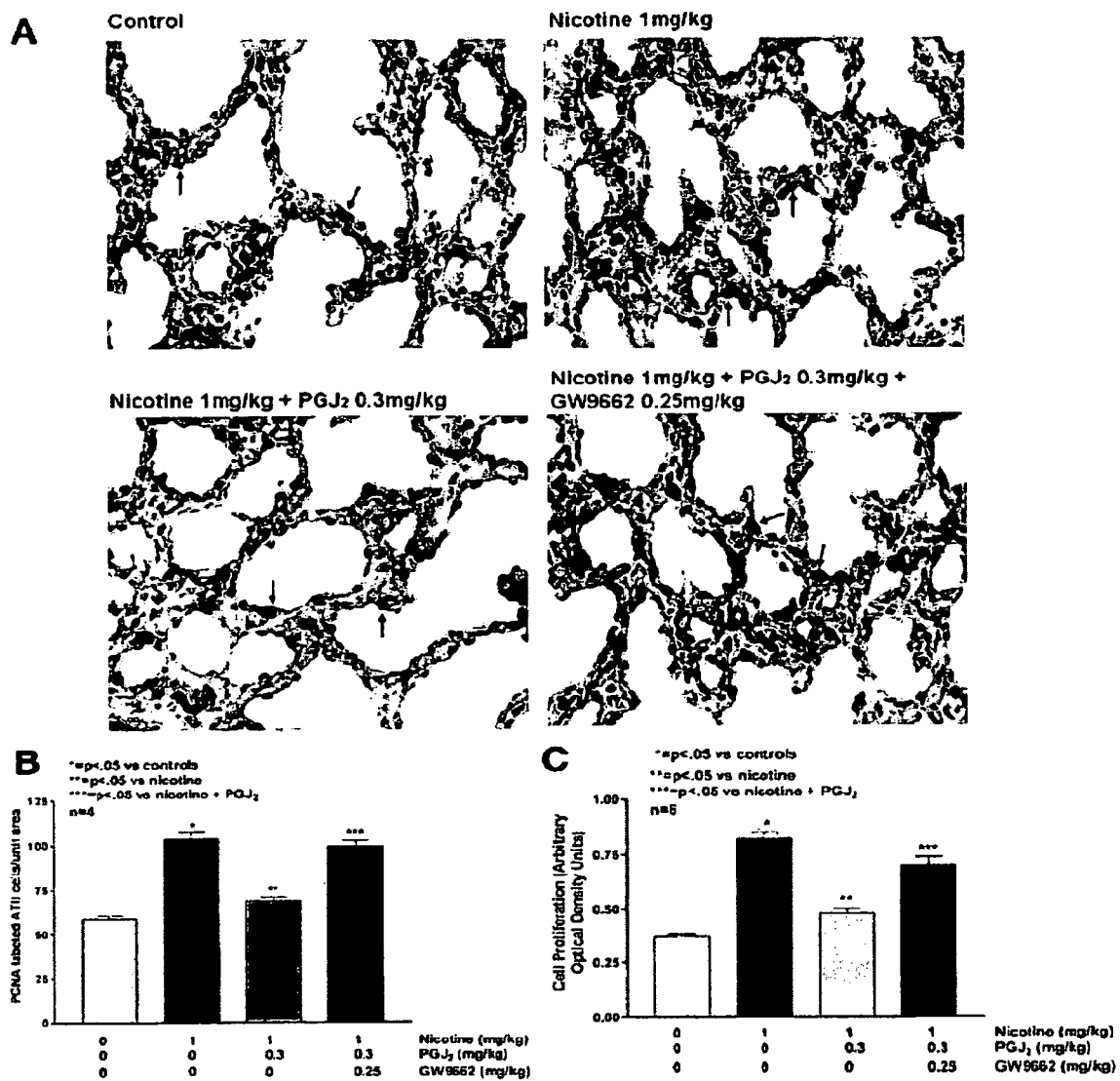
FIG. 18, panels A-F show the effect of nicotine on fetal alveolar type II (ATII) cell proliferation in vivo. In vivo fetal pulmonary ATII cell proliferation was determined immunohistochemically by double labeling with a cell proliferation-specific marker, proliferating cell nuclear antigen (PCNA), and an ATII cell-specific marker, surfactant protein (SP)-C (panels A and B) or assessed ex vivo by tetrazolium dye assay (panel C) after in utero nicotine administration to the dam (1 mg/kg ip) once daily from embryonic day 6 to 20. Cell proliferation was increased ~2-fold in the nicotine-exposed group vs. the control group. This increase was completely blocked by concomitant ad-ministration of a peroxisome proliferator-activated receptor (PPAR)-γ agonist, $PGJ_2$. A specific PPAR-γ antagonist, GW-9662, almost completely blocked the $PGJ_2$ effect on the nicotine-induced increase in ATII cell proliferation. In lung explants in culture treated with nicotine for 24 h, similar to the in vivo data, there was a significant increase in ATII cell proliferation, which was blocked by $PGJ_2$; again, GW-9662 blocked the $PGJ_2$ effect (panels D and E). Slides were examined at X40 magnification; black arrows in panels A and D show ATII cells labeled with PCNA (blue-gray nuclear stain) and SP-C (cytoplasmic stain). ATII cells in 10 randomly selected areas (grid size 40,000 $pm^2$) per slide (2 slides/animal) were counted. Panel F: no effect on cell proliferation in ATII cells directly stimulated in vitro with nicotine for 24 h.

Immunohistochemical analysis by double PCNA and SP-C staining demonstrated an almost twofold increase in ATII cell proliferation in the nicotine-exposed group (P<0.05, n=4; FIG. 18, panels A and B), which was completely blocked by the concomitant administration of the PPAR-γ agonist $PGJ_2$. A specific PPAR-γ antagonist, GW9662, almost completely blocked the $PGJ_2$ effect.

Ex Vivo Assessment.

Similar to the in vivo data, ex vivo assessment by the tetrazolium dye assay demonstrated an almost twofold increase in cell proliferation in the nicotine-exposed group (P<0.05, n=6) vs. the control group (FIG. 18, panel C). oncomitant treatment with $PGJ_2$ almost completely blocked the nicotine-induced increase in ATII proliferation. Similar to the in vivo data, GW-9662 blocked the $PGJ_2$ effect.

In Vitro Assessment.

Similar to the in vivo results, in lung explants in culture, 24 h of nicotine treatment significantly increased ATII cell proliferation (P<0.05, n=4), which was blocked by $PGJ_2$, and, again, GW-9662 blocked the $PGJ_2$ effect (FIG. 18, panels D and E). However, in contrast to the in vivo and ex vivo proliferation data, direct stimulation in vitro with nicotine for 24 h had no effect on ATII cell proliferation (FIG. 18, panel F).

Effect of Nicotine on Phospholipid Synthesis by ATII Cells

Effect of nicotine on [$^3H$]choline Incorporation into Disaturated Phosphatidylcholine: Ex Vivo Assessment.

Surfactant phospholipid synthesis, as measured by [$^3H$] choline incorporation into saturated phosphatidylcholine, by the cultured ATII cells from different experimental conditions was significantly increased in the nicotine-exposed group vs. the control group (P<0.05, n=6; FIG. 19, panel A). However, in contrast to the proliferation data, concomitant treatment with the PPAR-γ agonist $PGJ_2$, alone or in combination with the PPAR-γ antagonist GW-9662, had no effect on the nicotine-induced increase in phospholipid synthesis.

Effect of Nicotine on [$^3H$]choline Incorporation into Disaturated Phosphatidylcholine: In Vitro Assessment.

Direct stimulation of ATII cells in vitro with nicotine for 24 h also significantly increased choline incorporation (FIG. 19, panel B). Similar to the in vivo data, concomitant treatment with $PGJ_2$ alone or in combination with the PPAR-γ antagonist GW-9662 had no effect on the nicotine-induced increase in phospholipid synthesis.

Effect of Nicotine on CTP:CCT-a Expression.

We also determined the protein expression of CCT-α, the rate-limiting enzyme regulating surfactant phospholipid synthesis. Matching the increase in surfactant phospholipid synthesis, we observed a significant increase in CCT-α protein expression after in vivo and in vitro nicotine exposures (FIG. 20). Here again, similar to the choline incorporation data, treatment with $PGJ_2$, alone or in combination with GW-9662, had no effect on the nicotine-induced increase in phospholipid synthesis in vivo or in vitro.

Effect of Nicotine on SP-B Synthesis by ATII Cells

In vivo. Compared with the control group, in utero nicotine exposure significantly increased the steady-state SP-B protein level in the cultured ATII cells, as determined by Western analysis (P<0.05, n=3; FIG. 21, panel A). Neither PPAR-γ agonist ($PGJ_2$) nor antagonist (GW-9662) treatment had a significant effect on this nicotine-induced increase in SP-B expression.

In vitro.

Similar to the in vivo data, direct treatment of cultured ATII cells with nicotine resulted in a significant increase in SP-B expression that was unaffected by PPAR-γ agonist ($PGJ_2$) or antagonist (GW-9662) treatment (FIG. 21, panel B).

Effect of In Utero Nicotine Exposure on ATII Cell Metabolism

Along with the nicotine-induced increase in ATII cell proliferation and differentiation, there were metabolic changes that indicated significant effects of in utero nicotine exposure on the metabolic profile of the ATII cells. Most significantly, there were changes in the pentose cycle metabolism affecting ribonucleic acid synthesis and lipid metabolism that may have implications for surfactant synthesis.

Ribose Synthesis.

In vivo nicotine exposure significantly altered the pentose cycle metabolism in such a way that there was a significant increase in ribose synthesis via the oxidative glucose-6-phosphate dehydrogenase pathway, while there was a significant decrease in ribose synthesis via the nonoxidative transketolase pathway (FIG. 22, panels A and B). These metabolic alterations were completely blocked by concomitant administration of the PPAR-γ agonist $PGJ_2$. In contrast, direct in vitro treatment of cultured ATII cells with nicotine did not alter ribose synthesis via the oxidative or the nonoxidative pathway with or without the PPAR-γ agonist $PGJ_2$ (FIG. 22, panels C and D).

De Novopalmitate Synthesis.

De novo palmitate synthesis, as a function of the total palmitate in the ATII cells, almost doubled on in utero exposure to nicotine (FIG. 23, panel A). This was accompanied by a modest increase in the [$^{13}$C]glucose labeling of the acetyl-CoA pool (FIG. 23, panel B). Both of these changes were also completely prevented by the concomitant administration of the PPAR-γ agonist $PGJ_2$. Again, in contrast to the in vivo data, in vitro stimulation of ATII cells with nicotine for up to 72 h did not result in a significant change in de novo palmitate synthesis or [$^{13}$C] glucose labeling of the acetyl-CoA with or without the PPAR-γ agonist $PGJ_2$ (FIG. 23, panels C and D).

Discussion

The pulmonary effects of in utero nicotine exposure on the fetus are extremely complex. On the one hand, there is evidence of enhanced functional pulmonary maturity at birth, possibly contributing to a decrease in the incidence of respiratory distress syndrome (Curet et al. (1983) *Am. J. Obstet. Gynecol.* 147: 446-450; Gluck and Kulovich (1973) *Am. J. Obstet. Gynecol.* 115: 539-546; Lieberman et al. (1992) *Obstet. Gynecol.* 79: 564-570; Wuenschell et al. (1998) *Am. J. Physiol Lung Cell Mol Physiol* 274: L165-L170). On the other hand, significant reduction in prenatal and postnatal lung growth has been reported in children of women who smoke (Collins et al. 91985) *Pediatr. Res.* 19: 408-412; Cunningham et al. 91994) *Am. J. Epidemiol.* 139: 1139-1152, 1994; Hanrahan et al. (1992) *Am. Rev. Respir. Dis.* 145: 1129-1135). Significant suppression of alveolarization, functional residual capacity, and tidal flow volumes has been demonstrated in the offspring of nicotine-exposed pregnancies. Although the mechanisms underlying the general effects of maternal smoking on fetal viability and growth are generally thought to be due to fetal hypoxia, the mechanisms underlying the seemingly paradoxical acute and chronic pulmonary effects are far more complex and are just beginning to be elucidated (Pierce and Nguyen (2002) *Am. J. Respir. Cell Mol. Biol.* 26: 1013; Proskocil et al. (2005) *Am. J. Respir. Crit. Care Med* 171: 1032-1039; Rehan et al. (2005) *Am. J. Physiol. Lung Cell Mol. Physiol.* 289: L667-L676; Sekhon et al. (2992) *Am. J. Respir. Cell Mol. Biol.* 26: 31-41).

The direct effects of maternal smoke on prenatal lung growth are restricted to only those components of maternal smoke that are transferred across the placenta. Nicotine is the major smoke constituent that crosses the placenta and is concentrated in the fetus and, in animal studies, has been shown to adversely affect fetal lung growth and development (Bassi et al. (1984) *Pediatr. Res.* 18: 127-130; Collins et al. 91985) *Pediatr. Res.* 19: 408-412; Luck et al. (1985) *Dev. Pharmacol. Ther.* 8: 384-395; Maritz and Dennis (1998) *Reprod. Fertil. Dev.* 10: 255-261; Maritz and Thomas (1995) *Cell. Biol. Int.* 19: 323-331; Maritz and Woolward (1992) *S. Afr. Med. J.* 81: 517-519; Pastrakuljic et al. (1998) *Life Sci.* 63: 2333-2342; Sandberg et al. (2004) *Pediatr. Res.* 56: 432-439; Sekhon et al. (2992) *Am. J. Respir. Cell Mol. Biol.* 26: 31-41). Therefore, in the human fetus as well, nicotine is likely to be the major constituent causing pulmonary effects. We recently demonstrated that in vitro nicotine exposure specifically disrupts parathyroid hormone-related protein-driven alveolar epithelial-mesenchymal signaling, resulting in AIF-to-MYF trans-differentiation (Rehan et al. (2005) *Am. J. Physiol. Lung Cell Mol. Physiol.* 289: L667-L676). We have also suggested that augmentation of PPAR-γ signaling, the key downstream mesenchymal target of parathyroid hormone-related protein signaling, might be a plausible intervention for prevention of nicotine-induced in utero lung damage.

Because in vitro nicotine exposure disrupts specific alveolar epithelial-mesenchymal interactions, we hypothesized that exposure to nicotine in utero, in addition to affecting ATII cell function through its direct effects on ATII cells, would also affect it indirectly via its effects on the AIFs. Therefore, in this study, we have specifically examined the effects of nicotine exposure on ATII cell proliferation, differentiation, and metabolism in vivo as well as in vitro; furthermore, the effect of concomitant administration of the PPAR-γ agonist $PGJ_2$ was also examined.

We found that in utero fetal exposure to nicotine through parenteral administration to the mother significantly increased ATII cell proliferation and surfactant synthesis and altered glucose and lipid metabolism. In vivo and in vitro data suggest that surfactant synthesis is stimulated via nicotine's direct effects on ATII cells, whereas cell proliferation and metabolism are affected via the paracrine mechanism secondary to its effects on the adepithelial fibroblasts, suggesting direct and indirect effects of in utero nicotine exposure on fetal pulmonary ATII cells. These paracrine effects were almost completely prevented by the concomitant administration of the PPAR-γ agonist $PGJ_2$.

Our observation of increased ATII cell proliferation in response to in utero nicotine exposure is consistent with the observations of Maritz and Thomas (Maritz and Thomas (1995) *Cell. Biol. Int.* 19: 323-331). We have extended their observations by demonstrating that ATII cell proliferation increased with in vivo nicotine exposure, but not with direct in vitro nicotine stimulation of ATII cells, suggesting a likely paracrine mechanism underlying this response. Furthermore, the in vivo nicotine-induced ATII cell proliferation was, to a large extent, prevented by the concomitant administration of the PPAR-γ agonist $PGJ_2$. The possibility that the nuclear transcription factor PPAR-γ is playing a role in this response is further demonstrated by the observation that the PPAR-γ agonist-mediated prevention of the increase in ATII cell proliferation was completely blocked by the PPAR-γ-specific antagonist GW-9662. This finding is consistent with the antimitogenic role of PPAR-γ in other systems, where it has been shown that PPAR-γ can inhibit cell proliferation by regulating the activation of cyclins and cycin-dependent kinases (Dubey et al. (1993) *Am. J. Physiol. Regul. Integr. Comp. Physiol.* 265: R726-R732; Law et al. (2000) *Circulation* 101: 1311-1318; Wakino et al. (2000) *J. Biol. Chem.* 275: 22435-22441). Our recent work has clearly demonstrated that AIFs that are located adjacent to ATII cells express PPAR-γ (Rehan et al. (2006) *Exp. Lung Res.* 32: 379-393) and nicotine treatment down-regulates PPAR-γ expression by these fibroblasts (Rehan et al. (2005) *Am. J. Physiol. Lung Cell Mol. Physiol.* 289: L667-L676), which, in turn, may disturb the balance of fibroblast-derived epithelial cell growth-stimulatory and -inhibitory paracrine mediators, resulting in ATII cell proliferation.

With regard to nicotine's effect on surfactant synthesis, although a large body of work has been generated on the effects of cigarette smoke on the surfactant system in the adult, there is very limited information on the effects of nicotine exposure in the developing lung in utero. Lieberman et al. Lieberman et al. (1992) *Obstet. Gynecol.* 79: 564-570, reported higher amniotic fluid-saturated phosphatidylcholine contents in human fetuses exposed to intrauterine smoke. A related study reported an increase (Maritz and Thomas (1995) *Cell. Biol. Int.* 19: 323-331) in the lamellar body content of pulmonary ATII cells after intrauterine nicotine exposure. Recently, however, Chen et al. (2005) *Pediatr. Pulmonol.* 39: 97-102, did not find a significant difference in the saturated phosphatidylcholine contents in the lung tissue of nicotine-exposed vs. nonexposed rat pups on postnatal day 1. In contrast, after in utero nicotine exposure, we found an increase in saturated phosphatidylcholine synthesis, as measured by choline incorporation ex vivo by the fetal rat lung explants. Similarly, there is conflicting information on the effects of nicotine on SP expression by the developing lung. Chen et al. (Id.) did not find any effect of in utero nicotine exposure (from day 3 to day 21 of gestation) on the lung mRNA expression of SP-A, -B, -C, and -D in the newborn rat. However, Wuenschell et al. (1998) *Am. J. Physiol Lung Cell Mol Physiol* 274: L165-L170, reported significant increases in the expression of SP-A and -C mRNAs in a murine developing lung explant model. Hermans et al. (2001) *Pediatr. Res.* 50: 487-494, did not find any significant differences in amniotic fluid SP-A levels at full term in smoke-exposed vs. non-smoke-exposed pregnancies. The conflicting results in these studies are likely to be related to differences in the models used (species and stage of lung development), duration of nicotine exposure (acute vs. chronic), whether smoke or nicotine was used as a challenge, and the end points, for example, whether phospholipid synthesis, secretion, or total pool size was examined.

The effects of in utero nicotine exposure on glucose metabolism in fetal rat ATII cells have been only sparingly studied. In the whole lung of 14-day-old suckling pups, after nicotine exposure during pregnancy and lactation, glucose turnover was increased, and glycolysis and glycogenolysis were decreased (Kordom et al. (2003) *Exp. Lung Res.* 29: 79-89). This was attributed to an inhibition of the activity of phosphofructokinase. We found that although in vivo nicotine exposure significantly increased ribose synthesis via the oxidative glucose-6-phosphate dehydrogenase pathway and decreased it via the nonoxidative transketolase pathway, direct in vitro treatment of cultured ATII cells with nicotine did not alter ribose synthesis via the oxidative or the nonoxidative pathway. This discrepancy between in vitro and in vivo effects of nicotine on ATII cell glucose metabolism is similar to the previously reported discrepancy in the effect of nicotine exposure on phosphofructokinase activity in adult lung tissue under in vivo and in vitro conditions (Id). Since this effect was observed only under in vivo nicotine exposure conditions and not on direct in vitro nicotine stimulation of ATII cells, it is also likely to be mediated via a paracrine mechanism. Since ATII cells normally depend on the adjoining lipid-laden AIFs for their supply of neutral lipids for surfactant phospholipidsynthesis (Torday et al. (2002) *Am. J. Physiol. Lung Cell Mol. Physiol.* 283: L130-L135), the loss of lipogenic potential of these AIFs in response to in vivo nicotine exposure might be a trigger for the increase in de novo palmitate synthesis by the ATII cells under in vivo conditions. Since the nicotine-induced in vivo alterations in ATII cell glucose and lipid metabolisms were blocked by the concomitant administration of the PPAR-γ agonist $PGJ_2$, downregulation of PPAR-γ in AIFs is very likely the key modulator for these metabolic changes.

Taken together, these data indicate that in utero nicotine exposure significantly affects ATII cell proliferation, differentiation, and metabolism via direct and indirect effects of nicotine on ATII cells. The stimulation of ATII cell proliferation and surfactant synthesis after in utero nicotine exposure likely explains the decrease in the incidence of respiratory distress syndrome in infants of mothers who smoke during pregnancy (Curet et al. (1983) *Am. J: Obstet. Gynecol.* 147: 446-450; Gluck and Kulovich (1973) *Am. J. Obstet. Gynecol.* 115: 539-546; Lieberman et al. (1992) *Obstet. Gynecol.* 79: 564-570; Wuenschell et al. (1998) *Am. J. Physiol Lung Cell Mol Physiol* 274: L165-L170). However, since nicotine also disrupts the homeostatic alveolar epithelialmesenchymal interactions, resulting in AIF-to-MYF trans-differentiation (Rehan et al. (2005) *Am. J. Physiol. Lung Cell Mol. Physiol.* 289: L667-L676), the stimulatory effect of in utero nicotine exposure on ATII surfactant synthesis ultimately fails. This probably also explains why Chen et al. (supra) observed a significant decrease in the saturated phosphatidylcholine content of the lung tissue in nicotine-exposed vs. nonexposed rat pups on postnatal days 35 and 42, even when they found no differences between the two groups on postnatal day 1. Therefore, it is likely that, after in utero nicotine exposure, the combination of a nicotine-induced AIF-to-MYF transdifferentiation and a decrease in surfactant synthesis, in the long run, impacts lung function adversely.

Although the mechanisms underlying the effects of in utero nicotine exposure on ATII cell proliferation and differentiation remain to be fully elucidated, it seems that surfactant synthesis is stimulated via nicotine's direct effects on ATII cells, whereas cell proliferation and metabolism are affected via a paracrine mechanism secondary to its effects on the adepithelial fibroblasts.

However, the key finding that PPAR-γ agonist administration almost completely blocked the nicotine-induced effects on ATII cell proliferation and differentiation indicates that manipulation of PPAR-Y expression can at least partially prevent or even reverse the nicotine-induced ATII cell effects. Our previous finding that direct treatment of AIFs with nicotine downregulates PPAR-γ expression (Rehan et al. (2005) *Am. J. Physiol. Lung Cell Mol. Physiol.* 289: L667-L676) is consistent with our present findings and the proposed paracrine mechanism for the observed effects on ATII cell proliferation and differentiation. It is also important to note that ATII cells and AIFs express nicotinic acetylcholine receptors, which have been shown to be upregulated upon nicotine stimulation.

In summary, in addition to previously proposed mechanisms for in utero nicotine-induced lung effects, our data, for the first time, provide evidence for direct and indirect effects of in utero nicotine exposure on fetal pulmonary ATII cells that could permanently alter the "developmental program" of the developing lung. The use of PPAR-γ agonists can, at least partially, ameliorate the complex nicotine-induced lung injury in utero. In this regard, it is important to note that to more effectively prevent the maternal nicotine exposure-induced effects on the offspring's ATII cell proliferation, differentiation, and metabolism, PPAR-γ agonist intervention might be needed not only during gestation but also during lactation.

Example 3

Nicotine-Induced Lung Injury can be Reversed

The data presented below indicate that using the approach outlined above, the nicotine-induced lung injury can not only be prevented but also reversed. It is believed this is first demonstration of the possibility of a reversal of the nicotine-induced lung injury by using any approach. As illustrated below, in cultured human lung fibroblasts, we first documented the nicotine-induced changes in fibroblast phenotype to a muscle like phenotype and then by molecularly manipulating these nicotine treated fibroblasts, we were able the reverse the nicotine-induced fibroblast phenotype to its original non-nicotine exposed phenotype.

Embryonic human lung fibroblasts initially exposed to nicotine ($10^{-9}$M) for 7 days and then treated with PPARγ agonists (RGZ, PTHrP, or cAMP) for the following 7 days. Even after nicotine treatment was stopped, PTHrP receptor expression continued to be significantly lower in nicotine treated controls compared to untreated controls. In contrast, treatment with RGZ, PTHrP, or cAMP not only reversed nicotine-induced decrease in PTHrP receptor expression, in fact, even markedly increased in comparison to untreated controls.

Similar to the reversal of PTHrP receptor expression, nicotine-induced decrease in PPARγ expression was also reversed with treatments with RGZ and PTHrP. Although with cAMP there was a trend towards an increase in PPARγ expression, it did not reach statistical significance.

αSMA expression was significantly higher in nicotine treated controls vs. untreated controls even after 7 days after stopping nicotine treatment. However, treatment with RGZ, PTHrP, or cAMP reversed the nicotine-induced increase in αSMA expression.

To assess the functional relevance of the reversal of the nicotine-induced fibroblast phenotype, we examined the triolein uptake (a functional marker of normal lung fibroblast phenotype) following different experimental conditions. As predicted, nicotine treatment resulted in a significant decrease in triolein uptake, which was at least partially blocked by treatments with all 3 (RGZ, PTHrP, and cAMP) agonists of the normal fibroblast phenotype. PTHrP signaling pathway.

Example 4

Reversal of Nicotine-Induced Alveolar Lipofibroblast-to-Myofibroblast Transdifferentiation by Stimulants of Parathyroid Hormone-Related Protein Signaling Nicotine exposure disrupts the parathyroid hormone-related protein (PTHrP)-driven alveolar epithelial-mesenchymal paracrine-signaling pathway, resulting in the transdifferentiation of pulmonary lipofibroblasts (LIFs) to myofibroblasts (MYFs), which seems to be central to altered pulmonary development and function in infants born to mothers who smoke during pregnancy. Modulation of PTHrP-driven signaling can almost completely prevent nicotine-induced LIF-to-MYF transdifferentiation. However, once this process has occurred, whether it can be reversed is not known. Our objective was to determine if nicotine-induced LIF-to-MYF transdifferentiation could be reversed by specifically targeting the PTHrP-mediated alveolar epithelial-mesenchymal paracrine signaling. WI38 cells, a human embryonic pulmonary fibroblast cell line, were initially treated with nicotine for 7 days and LIF-to-MYF transdifferentiation was confirmed by determining the downregulation of the key lipogenic marker, peroxisome proliferator-activated receptor γ (PPARγ) and upregulation of the key myogenic marker, α-smooth muscle actin (αSMA). Because downregulation of the PPARγ signaling pathway is the key determinant of LIF-to-MYF transdifferentiation, cells were treated with three agonists of this pathway, PTHrP, dibutryl cAM3 (DBcAMP), or rosiglitazone (RGZ) for 7 days, and the expression of the PTHrP receptor, PPARγ, αSMA, and calponin was determined by Western analysis and immunohistochemistry. Simultaneously, fibroblast function was characterized by measuring their capacity to take up triglycerides. Nicotine-induced LIF-to-MYF transdifferentiation was almost completely reversed by treatment with RGZ, PTHrP, or DBcAMP, as determined by protein and functional assays. Using a specific molecular approach and targeting specific molecular intermediates in the PTHrP signaling pathway, to our knowledge, this for the first time, demonstrates the reversibility of nicotine-induced LIF-to-MYF transdifferentiation, suggesting not only the possibility of prevention but also the potential for reversal of nicotine-induced lung injury.

Introduction

There is strong epidemiologic and experimental evidence that fetal exposure to maternal smoking during gestation results in detrimental long-term effects on lung growth and function (Maritz (1988) *Biol. Neonate* 53: 163-170; Walsh (1994) *Hum. Biol.* 66: 1059-1092; Chen et al. (1987) *Pediair. Pulmonol.* 3: 51-58; Collins et al. (1985) *Pediatr. Res.* 19: 408-412; Cunningham et al. (1994) *Am. J. Epidemiol.* 139: 1139-1152). Significant suppression of alveolarization, functional residual capacity, and tidal volume has been demonstrated in the offspring of nicotine-exposed pregnancies (Maritz (1988) *Biol. Neonate* 53: 163-170; Walsh (1994) *Hum. Biol.* 66: 1059-1092; Chen et al. (1987) *Pediatr. Pulmonol.* 3: 51-58; Collins et al. (1985) *Pediatr. Res.* 19: 408-412; Cunningham et al. (1994) *Am. J. Epidemiol.* 139: 1139-1152; Hanrahan et al. (1992) *Am. Rev. Respir. Dis.* 145: 1129-1135; Sekhon et al. (2002) *Am. J. Respir. Cell. Mol. Biol.* 26: 3141). Although the molecular mechanisms underlying the long-term pulmonary effects following in utero nicotine exposure remain poorly understood (Pierce and Nguyen (2002) *Am. J. Respir. Cell. Mol. Biol.* 26: 10-13; Rehan et al. (2005) *Am. J. Physiol. Lung Cell Mol. Physiol.* 289: L667-L676), our recent work has clearly implicated the disruption of the homeostatic alveolar epithelial-mesenchymal parathyroid hormone-related protein (PTHrP) paracrine-signaling pathway following in utero nicotine exposure that results in the transdifferentiation of pulmonary lipofibroblasts (LIFs) to myofibroblasts (MYFS) (Rehan et al. (2005) *Am. J. Physiol. Lung Cell Mol. Physiol.* 289: L667-L676). Normally, under the influence of cyclic stretch, e.g., during normal breathing, PTHrP is secreted by the alveolar type II cell, which binds to its cognate receptor on the lipofibroblast, activating the cAMP-dependent PKA-mediated lipogenic pathway (FIG. 24) and upregulating PPARc and its downstream targets, ADRP, which facilitates triglyceride uptake by the lipofibroblast (Schultz et al. (2002) *Am. J. Physiol. Lung Cell Mol. Physiol.* 283: L288-L296) and leptin, which stimulates surfactant phospholipid and protein synthesis by the alveolar type II cell (Torday et al. (2002) *Am. J. Physiol. Lung Cell Mol. Physiol.* 282: L405-L410, erratum in *Am. J. Physiol. Lung Cell Mol. Physiol.* (2002) 282(4) Section L). The triglycerides taken up by the lipofibroblast are then trafficked to the ATII cell as substrate for surfactant phospholipid synthesis (Torday et al. (1995) *Biochem. Biophys. Acta* 1254: 198-206). In fact, for surfactant phospholipid synthesis, ATII cells are essentially dependent on lipofibroblasts to recruit neutral lipids from the circulation to be trafficked to the ATII cells and incorporated into surfactant phospholipids. Nicotine exposure downregulates the PTHrP signaling pathway resulting in LIF-to-MYF transdifferentiation, which seems to be central to altered pulmonary development and function in infants born to mothers who smoke during pregnancy. Even more important, we have shown that PTHrP signaling pathway agonists can almost completely prevent nicotine-induced LIF-to-MYF transdifferentiation (FIG. 24).

The present series of experiments was designed to determine whether, by specifically targeting the PTHrP-mediated alveolar epithelial-mesenchymal paracrine-signaling pathway, nicotine-induced LIF-to-MYF transdifferentiation can be reversed after it has occurred. The data presented herein clearly suggest that using a specific molecular approach that targets the intermediates in the PTHrP signaling pathway, nicotine-induced LIF-to-MYF transdifferentiation can be reversed, suggesting not only the possibility of prevention but also the potential for reversal of nicotine-induced lung injury. This clearly has significant potential therapeutic implications for both in utero and postnatal nicotine-induced lung injury.

Materials and Methods

Reagents

PTHrP-(1-34) was obtained from Bachem (Torrance, Calif.) and rosiglitazone from Cayman Chemical (Ann Arbor, Mich.). DBcAMP and alpha smooth muscle actin (αSMA) antibody were obtained from Sigma Biochemicals (St. Louis, Mo.). Calponin antibody was obtained from Santa Cruz Biotechnology, Inc. (Santa Cruz, Calif.), peroxisome proliferator-activated receptor γ (PPARγ) antibody from Alexis Biochemicals (San Diego, Calif.), and adipocyte differentiation related protein (ADRP) antibody was a kind gift from Dr. Constantine Londos, NIDDK.

Cell Culture

The human embryonic cell line WI38 was obtained from the American Type Culture Collection (Rockville, Md.). Cells were grown in minimum essential medium (MEM) +10% fetal bovine serum at 37° C. in six-well plates, two well slides, and 60-mm and 100-mm culture dishes, as needed. At 70%-80% confluence, cells were initially treated with nicotine ($1 \times 10^{-9}$ M) for 7 days and LIF-to MYF transdifferentiation was confirmed by determining the downregulation of the key lipogenic marker, PPARγ, and upregulation of the key myogenic marker, αSMA, by Western analysis. Subsequently, the cells were treated with rosiglitazone (RGZ) ($1 \times 10^{-5}$ M) (a PPARγ agonist), PTHrP ($5 \times 10^{-7}$ M), or DBcAMP ($1 \times 10^{-5}$ M) for 7 days, and the expression of PTHrP receptor, PPARγ, ADRP, calponin, and cSMA was determined by Western analysis and immunohistochemistry. Simultaneously, fibroblast function was characterized by measuring their capacity to take up triglycerides. Some experiments were performed in the presence of a specific PPARγ antagonist, GW9662. Medium containing fresh chemicals was added daily, and at the end of the experimental period the cells were processed as needed.

Triglyceride Uptake Assay

The method used to quantitate triglyceride uptake by fetal rat lung fibroblasts has been described previously (Torday et al (1995) *Biochem. Biophys. Acta* 1254: 198-206). Briefly, culture medium was replaced with DMEM containing 20% adult rat serum mixed with [$^3$H]triolein (5 μCi/ml). The cells were incubated at 37° C. in 5% $CO_2$-air balance for 4 h. At the termination of the incubation, the medium was decanted, the cells were rinsed twice with 1 ml of ice-cold phosphate buffered saline (PBS), and the cells were removed from the culture plate after a 5-10 min incubation with 2 ml of a 0.05% trypsin solution. An aliquot of the cell suspension was taken for protein assay, and the remaining cell suspension was extracted for neutral lipid content.

Protein Determination and Western Blot Analysis

Protein determination was made using the Bradford dye-binding method (Bradford (1976) *Anal. Biochem.* 72: 248-254). For Western blotting, cells were lysed using an extraction buffer [10 mM tris (hydroxymethyl) aminomethane (Tris, pH 7.5), 0.25 M sucrose, 1 mM EDTA, 5 mM benzamidine, 2 mM phenylmethylsulfonyl fluoride, and 10 (j.tg/ml each of pepstatin A, aprotinin, and leupeptin], and centrifuged at 140 g for 10 min (4° C.). Equal amounts of the protein (25 μg) from the supernatant were dissolved in electrophoresis sample buffer and were subjected to sodium dodecyl sulfate-polyacrylamide (4%-12% gradient) gel electrophoresis (SDS-PAGE) followed by electrophoretic transfer to a nitrocellulose memane. The nonspecific binding of antibody was blocked by washing with Tris-buffered saline (TBS) containing 0.1% Tween 20 (TBST) and 5% milk for 1 h. The blot was then subjected to two brief washes with TBST plus 0.5% Tween 20, incubated in TBST plus 0.1% Tween 20 and the specific primary antibodies (PPARγ 1:2000, Alexis Biochemicals, San Diego, Calif.; cSMA 1:50,000, Sigma, St. Louis, Mo.: ADRP 1:3000) overnight at 4° C. Blots were then washed in TBST plus 0.1% Tween 20 and then incubated for 1 h in secondary antibody, washed, and developed with a chemiluminescent substrate [enhanced chemiluminescence (ECL); Amersham, Arlington Heights, Ill.] following the manufacturer's protocol. The densities of the specific protein bands were quantified using a scanning densitometer (Eagle Eye II still video system, Stratagene, La Jolla, Calif.). The blots were subsequently stripped and reprobed with anti-GAPDH (1:5000, Chemicon, Inc., Temecula, Calif.) antibody to confirm equal loading of samples.

Immunofluorescence Double Staining

The lipogenic and myogenic status of cultured WI38 cells was assessed by simultaneous staining for either lipid droplets or ADRP and αSMA. Lipids were detected by using either oil red 0 staining or ADRP expression (polyclonal anti-ADRP 1:500), and αSMA expression was assessed by using anti-αSMA (1:1000, mouse monoclonal IgG$_{2a}$, Sigma, catalog No. A2547) primary antibody. In brief, cells were cultured on Lab-Tek® 2-chamber slides under control and experimental conditions (nicotine treatment, $1 \times 10^9$ M for 7 days). At the end of the experimental period, slides were fixed in freshly prepared 4% paraformaldehyde. Fixed slides were washed in PBS, blocked with 3% normal goat serum (Jackson Immunoresearch Lab) in PBS for 30 min at room temperature to block nonspecific binding, and then incubated for 1 h at room temperature with primary antibodies αSMA and ADRP. Thereafter, slides were washed in PBS for 5 min, then incubated in the dark for 30 min using a mixture of secondary goat anti-mouse IgG$_{2a}$-conjugated FITC and goat anti-rabbit IgG conjugated Texas red. The slides were then washed in PBS for 5 min and mounted using Vesta shield mounting medium with DAPI (Vector Laboratories, Burlingame, Calif.). For αSMA and oil red O double staining, the slides were incubated with cSMA for 1 h at room temperature, followed by secondary goat anti-mouse IgG$_{2a}$ with FITC for 30 min. The slides were washed in distilled water and then incubated with oil red O (Sigma, St. Louis, Mo.) for 15 min. Slides were rinsed three times for 5 min and then mounted and visualized under a fluorescence microscope.

Statistical Analysis

Analysis of variance for multiple comparisons using the Newman-Keuls post hoc test was used to analyze the experimental data. A p value less than 0.05 was considered to indicate significant differences among various experimental groups.

Results

Nicotine Induces Alveolar Interstitial Lipo-to Myofibroblast Transdifferentiation In accord with our previous observations [9], by Western analysis we first confirmed that nicotine treatment of cultured embryonic human lung fibroblasts (WI38 cells) for 7 days resulted in significant decreases in the expression of PTHrP receptor (*p<0.001 vs. control; n=3), PPARγ (*p<0.001 vs. control; n=3), and ADRP (*p<0.05 vs. control; n=3), and significant increases in the expression of αSMA (*p<0.001 vs. control; n=3) and calponin (*p<0.001 vs. control; n=3) (FIG. 25).

Figure 26A:
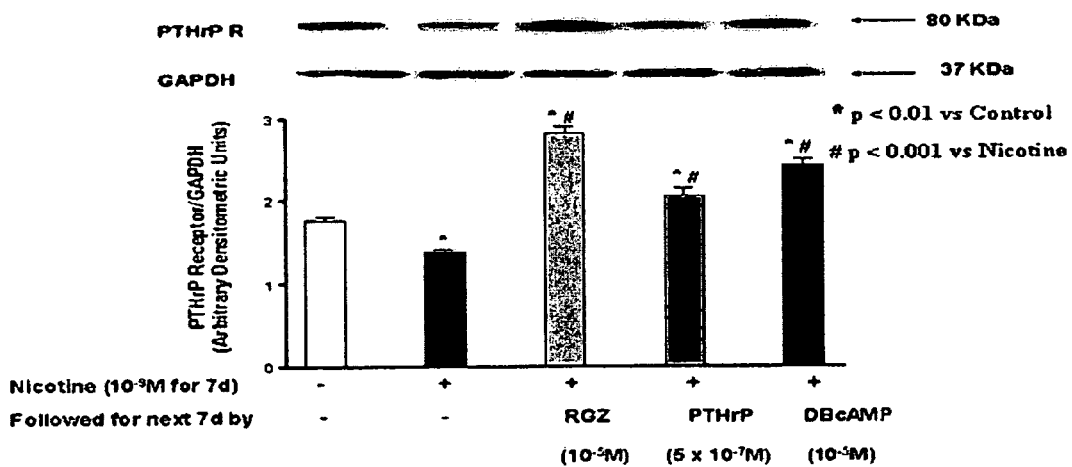
Figure 26B:
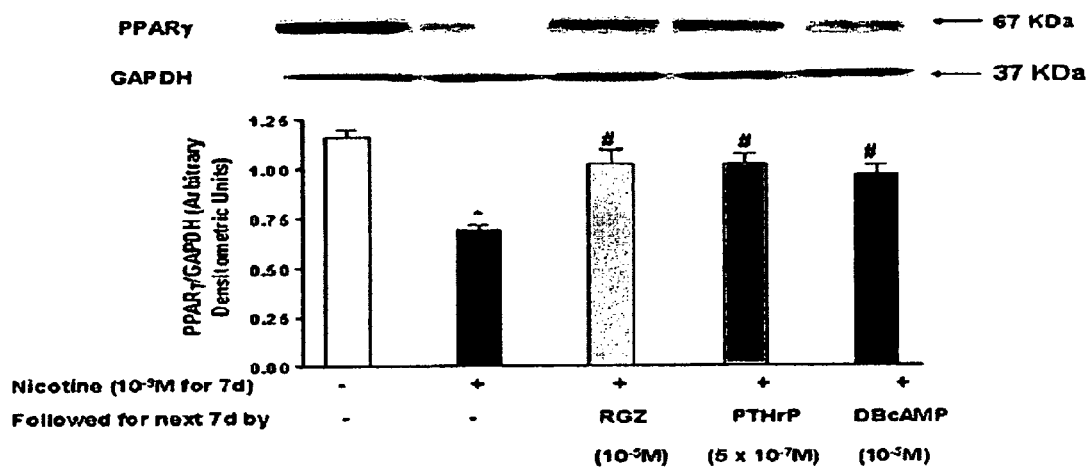
Figure 26C:
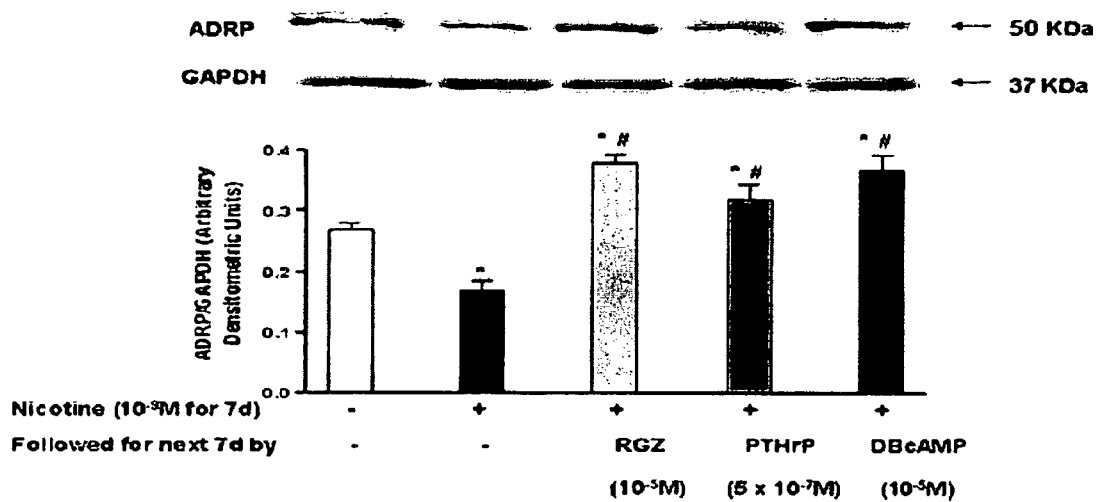
Figure 27A:
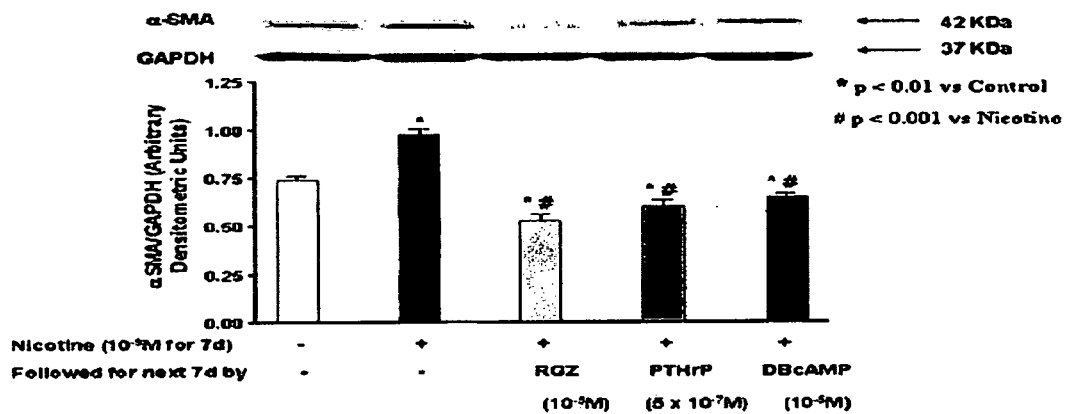
Figure 27B:
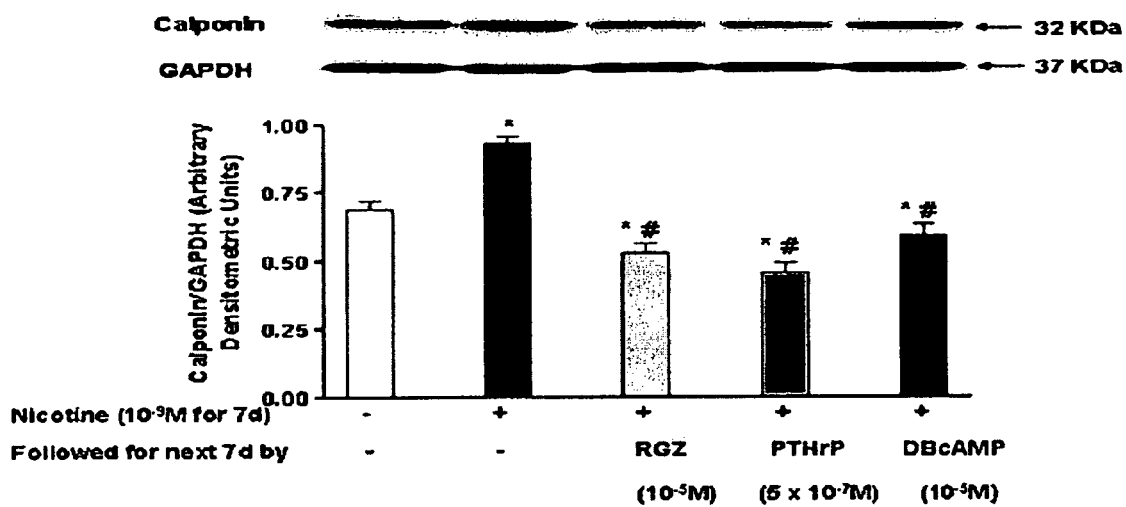

Reversal of Nicotine-Induced Alveolar Interstitial Lipoto-Myofibroblast Transdifferentiation by PTHrP Signaling Pathway Agonists Following 7 days exposure to nicotine ($10^{-9}$ M), embryonic human lung fibroblasts were kept in culture either without (7d nicotine-only treatment group) or with PTHrP signaling agonists [RGZ($1\times10^{-5}$ M), PTHrP($5\times10^{-7}$M), or DBcAMP($1\times100$-5 M)] for the following 7 days. Subsequently, expression of the various markers for the fibroblast phenotypes (PTHrP receptor, PPARγ, ADRP, αSMA, and calponin) was evaluated by Western analysis. In the 7d nicotine-only treatment group, despite the absence of continued nicotine exposure, the expression of PTHrP receptor, PPARγ, and ADRP continued to be significantly lower and the expression of αSMA and calponin significantly higher compared to untreated controls. In contrast, however, treatment with PTHrP pathway agonists almost completely reversed the nicotine-induced changes in the expression of PTHrP receptor (*p<0.05 vs. control and #p<0.001 vs. nicotine; n=3; FIG. 26A), PPARγ (*p<0.01 vs. control and #p<0.05 vs. nicotine; n=3; FIG. 26B), ADRP (*p<0.01 vs. control and #p<0.001 vs. nicotine; n=3; FIG. 26C), cSMA (*p<0.01 vs. control and #p<0.001 vs. nicotine; n=3; FIG. 27A) and calponin (p<0.001 vs. control and #p<0.001 vs. nicotine; n=3; FIG. 27B). This reversal of nicotine-induced LIF-to-MYF transdifferentiation was corroborated by immunochemistry (FIG. 28).

Immunofluorescence costaining for ADRP and αSMA or lipid droplets (oil red O) and cSMA following nicotine treatment resulted in marked decreases in ADRP and lipid droplet staining and a marked increase in αSMA staining. Both RGZ and cAMP treatments reversed the nicotine-induced decreases in ADRP and lipid droplet staining and the increase in αSMA staining.

Time Frame for PTHrP Signaling Pathway Agonist-Mediated Reversal of Nicotine-Induced Lipo-to-Myofibroblast Transdifferentiation In the above experiments reversal of nicotine-induced molecular changes was assessed following 7 days of treatment with PTHrP signaling pathway agonists. To assess how soon this reversal might occur, we next examined the evidence for the reversal of the nicotine-induced LIF-to-MYF transdifferentiation following only 24 h of treatment with PTHrP signaling pathway agonists (FIG. 29). Similar to the 7-day data, there was clear evidence of reversal of nicotine-induced LIF-to-MYF transdifferentiation even after only 24 h of treatment with PTHrP signaling agonists.

Functional Relevance of Reversal of Nicotine-Mediated Lipo-to-Myofibroblast Transdifferentiation To determine whether reversal of nicotine-induced LIF-to-MYF transdifferentiation by stimulants of PTHrP signaling was functionally relevant, we next examined triglyceride uptake by fibroblasts following various treatment conditions. Robust triglyceride uptake is a functional characteristic of LIFs and is not a prominent feature of MYFs. As predicted, nicotine treatment resulted in a significant decrease in triolein uptake, which was at least partially blocked by treatment with all three agonists of the PTHrP signaling pathway (*p<0.001 vs. control and #p<0.001 vs. nicotine groups, n=3; FIG. 30).

PPARy Expression is Central to the Reversal of Nicotine-Induced Lipo-to-Myofibroblast Transdifferentiation by Stimulants of the PTHrP Signaling Pathway Because our work has demonstrated that PPARγ expression is central to the maintenance of the alveolar interstitial fibroblast lipogenic phenotype, we next examined the centrality of PPARγ expression in the reversal of nicotine-induced LIF-to-MYF transdifferentiation by PTHrP signaling agonists. As expected, pretreatment with a specific PPARγ antagonist, GW9662, completely blocked the molecular protection against nicotine-induced LIF-to-MYF transdifferentiation by all three PTHrP signaling pathway agonists (PTHrP, DBcAMP, and RGZ) studied, suggesting the specificity of PPARγ activation in the protection provided by PPARγ against nicotine-induced LIF-to-MYF transdifferentiation (*p<0.001 vs. control; #p<0.01 vs. nicotine; ^p<0.001 vs. nicotine+RGZ; @p<0.001 vs. nicotine+PTHrP; and $p<0.001 vs. nicotine+cAMP groups; n=3; FIG. 31).

Discussion

Nicotine disrupts specific PTHrP-driven alveolar epithelial-mesenchymal paracrine signaling, resulting in the transdifferentiation of pulmonary LIFs to MYFs. We have suggested that LIF-to-MYF transdifferentiation is a central mechanism that contributes to the altered pulmonary development and function in infants born to mothers who smoke during pregnancy (Rehan et al. (2005) *Am. J. Physiol. Lung Cell Mol. Physiol.* 289: L667-L676). Nicotine exposure downregulates the PTHrP-driven cAMP-dependent protein kinase A pathway, which normally induces the alveolar interstitial fibroblast lipogenic phenotype that is essential for normal pulmonary development and homeostasis (Rubin et al. (2004) *Dev. Dyn.* 230: 278-289; Torday et al (2003) *Pediatr. Pathol. Mol. Med.* 22: 189-207). LIF-to-MYF transdifferentiation results in failed alveolarization in the developing lung, which leads to an arrest in pulmonary growth and development, the hallmarks of in utero nicotine-induced lung damage (Collins et al. (1985) *Pediair. Res.* 19: 408-412; Maritzand Dennis (1998) *Reprod. Feril. Dev.* 10: 255-261). Furthermore, modulation of the fibroblast PTHrP-driven signaling pathway can almost completely "prevent" nicotine-induced LIF-to-MYF transdifferentiation (Rehan et al. (2005) *Am. J. Physiol. Lung Cell Mol. Physiol.* 289: L667-L676). However, once this process (LIF-to-MYF transdifferentiation) has occurred, whether it could be reversed was not known before this study. In this experiment, consistent with our previous observations, we initially confirmed that 7-day treatment of WI38 cells with nicotine ($1\times10^{-9}$) resulted in significant decreases in PTHrP receptor, PPARy, and ADRP protein expression and significant increases in SMA and calponin protein expression, thereby confirming either 24 h or 7 days reversed nicotine-induced LIF-to-MYF transdifferentiation, as demonstrated by Western analysis, immunohistochemistry, and triglyceride uptake.

Smoking is the most common addiction among pregnant women in the U.S. An estimated 12% of pregnant women are reported to smoke during pregnancy, and despite all the publicity on the harmful effects of smoking on the pregnant woman and her fetus, only 20% of women quit smoking during pregnancy (Hamilton et al. (2004) *Natl. Vital Stat. Rep.* 53: 1-17). To stop smoking altogether before or during pregnancy, although ideal, is not a realistic goal, and therefore any intervention that can safely prevent or reverse the smoke-induced effects could be an effective, practical strategy to prevent the harmful effects of in utero smoke exposure.

Although there are many agents in smoke that may be detrimental to the developing lung, there is clear evidence showing that nicotine directly affects fetal lung development. Nicotine crosses the human placenta with minimal biotransformation to its metabolite cotinine (Pastrkuljic et al. (1998) *Life Sci.* 63: 2333-2342). In fact, nicotine accumulates in fetal blood and amniotic fluid, resulting in the fetus being exposed to even higher nicotine levels compared to the smoking mother, and it accumulates in several fetal tissues, including the respiratory tract, suggesting that nicotine is the likely agent that alters lung developmental programming in the fetus of the pregnant smoker (Luck et al. (1985) *Dev. Pharmacol. Ther.* 8: 384-395; Szuts et al. (1978) *Toxicology* 10: 207-220). The data presented herein suggest that improvement in lung development following in utero nicotine exposure can be accomplished.

Although in utero smoke exposure-induced lung injury is a complex process (Pierce and Nguyen (2002) *Am. J. Respir. Cell. Mol. Biol.* 26: 10-13; Rehan et al. (2005) *Am. J. Physiol. Lung Cell Mol. Physiol.* 289: L667-L676; Proskocil et al. (2005) *Am. J. Respir. Crit. Care Med.* 171: 1032-1039), nicotine-induced LIF-to-MYF transdifferentiation is a mechanism that explains many of the pulmonary structural and functional findings seen following in utero nicotine exposure. Understanding the precise molecular mechanism involved in LIF-to-MYF transdifferentiation and its prevention provides a fundamental approach to preventing smoke-induced lung injury. The hypothesis that PPARγ is a critical downstream target for PTHrP/PTHrP receptor signaling and is central to the lipogenic phenotype of alveolar interstitial fibroblasts (. Rehan et al. (2005) *Am. J. Physiol. Lung Cell Mol. Physiol.* 289: L667-L676; Torday et al. (2003) *Pediatr. Pathol. Mol. Med.* 22: 189-207) is yet again suggested by the data presented in this report: (1) LIF-to-MYF transdifferentiation was accompanied by PPARγ downregulation, (2) reversal of LIF-to-MYF transdifferentiation was accompanied by upregulation of PPARγ, and, most tellingly, (3) the specific PPARγ antagonist, GW9662, blocked the reversal of LIF-to-MYF transdifferentiation by all three upstream stimulators of PPARγ, RGZ, PTHrP, and DBcAMP.

In summary, nicotine-induced LIF-to-MYF transdifferentiation was almost completely reversed by treatment with PTHrP, RGZ, or DBcAMP, as determined by the expression of the various markers of the LIF and MYF phenotypes. By targeting specific molecular intermediates in the PTHrP signaling pathway, nicotine-induced LIF-to-MYF transdifferentiation is almost completely reversible, suggesting not only the possibility of prevention but also the potential for reversal of nicotine-induced lung injury.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing, eliminating, and/or reversing pulmonary tissue damage characterized by smoke-induced pulmonary alveolar trans-differentiation of lipofibroblasts to myofibroblasts in utero in a developing fetus carried by a pregnant mammal, said method comprising administering a PPAR gamma (PPARγ) agonist to said pregnant mammal in an amount sufficient to reduce, eliminate, or reverse said transdifferentiation.

2. The method of claim 1, wherein said pregnant mammal is a human smoker.

3. The method of claim 1, wherein said pregnant mammal is a human exposed to second-hand smoke.

4. The method of claim 1, wherein said pregnant mammal is a non-human mammal exposed to second-hand smoke.

5. The method of claim 1, wherein said pregnant mammal is a human that is formerly a smoker.

6. The method of claim 1, wherein said pregnant mammal is not being treated for diabetes and/or obesity or anorexia, and/or an eating or appetite disorder.

7. The method of claim 1, wherein said PPAR gamma agonist is a thiozolidinedione.

8. The method of claim 1, wherein said PPAR gamma agonist is selected from the group consisting of rosiglitazone, troglitazone (Resulin), farglitazar, phenylacetic acid, GW590735, GW677954, Avandia, Avandamet (avandia+metformin), ciglitazone, 15 deoxy prostaglandin J2 (15PGJ2), pioglitazone (Actos), 15-deoxy-delta12,14 PGJ2, MCC-555, and triterpenoids.

9. The method of claim 1, wherein said PPAR gamma agonist is administered to said pregnant mammal via an inhalation route.

10. The method of claim 9, wherein said PPAR gamma agonist is administered via a nasal spray.

11. The method of claim 9, wherein said PPAR gamma agonist is administered via an oral inhaler.

12. The method of claim 1, wherein said PPAR gamma agonist is administered to said pregnant mammal orally.

13. The method of claim 1, wherein said PPAR gamma agonist is administered to said pregnant mammal systemically.

14. The method of claim 1, wherein said human is a human that has been exposed to second hand smoke.

15. The method of claim 1, wherein said method reverses said transdifferentiation.

\* \* \* \* \*